(12) United States Patent
Suzuki et al.

(10) Patent No.: US 8,202,687 B2
(45) Date of Patent: Jun. 19, 2012

(54) METHOD FOR TRANSPORTING POTASSIUM IONS FROM FRONT SIDE TO BACK SIDE OF LIPID BILAYER MEMBRANE

(75) Inventors: Masato Suzuki, Kyoto (JP); Hiroaki Oka, Osaka (JP); Shigeki Kiyonaka, Kyoto (JP); Yasuo Mori, Kyoto (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/248,880

(22) Filed: Sep. 29, 2011

(65) Prior Publication Data

US 2012/0083001 A1 Apr. 5, 2012

Related U.S. Application Data

(63) Continuation of application No. PCT/JP2011/000375, filed on Jan. 25, 2011.

(30) Foreign Application Priority Data

Oct. 1, 2010 (JP) ................................. 2010-223737

(51) Int. Cl.
*C12Q 1/00* (2006.01)
*G01N 33/53* (2006.01)

(52) U.S. Cl. ............................................ 435/4; 435/7.2

(58) Field of Classification Search ........................ None
See application file for complete search history.

(56) References Cited

U.S. PATENT DOCUMENTS

| 6,046,321 | A  | 4/2000 | Cowsert |
| 2004/0072157 | A1 | 4/2004 | Graber |
| 2005/0181452 | A1 | 8/2005 | Westwick et al. |

FOREIGN PATENT DOCUMENTS

JP 2008-514185 5/2008

OTHER PUBLICATIONS

D.E. Gloriam et al., "The G protein-coupled receptor subset of the rat genome," BMC Genomics 8, 338-405 (2007).
W.M. Oldham et al., "Heterotrimeric G protein activation by G-protein-coupled receptors," Nat. Rev Mol. Cell Biol. 9, 60-71 (2008).
K.W. Chan et al., "Control of channel activity through a unique amino acid residue of a G protein-gated inward rectifying $K^+$ channel subunit," Proc. Natl. Acad. Sci., 93, 14193-14198 (1996).
G.J. Digby et al., "Differential dissociation of G protein heterotrimers," The Journal of Physiology, 586, 3325-3335 (2008).
W. Thomsen et al., "Functional assays for screening GPCR targets," Current Opinion in Biotechnology, 16, 655-665 (2005).
J.L. Leaney et al., "The G Protein α Subunit Has a Key Role in Determining the Specificity of Coupling to, but Not the Activation of, G-Protein-Inwardly Rectifying $K^+$ Channels," J. Biol. Chem., 275, 921-929, (2000).
J.L. Leaney et al., "The role of members of the pertussis toxin-sensitive family of G proteins in coupling receptors to the activation of the G protein-gated inwardly rectifying potassium channel," Proc. Natl. Acad. Sci. USA, 2000, vol. 97, No. 10, pp. 5651-5656.
I. Rishal et al., "Gβγ-dependent and Gβγ-independent Basal Activity of G Protein-activated $K^+$ Channels," J. Chem., 2005, vol. 280, No. 17, pp. 16685-16694.

*Primary Examiner* — Ruixiang Li
(74) *Attorney, Agent, or Firm* — McDermott Will & Emery LLP

(57) ABSTRACT

An object of the present invention is to detect a specific chemical substance with high sensitivity and high precision. By using a specific lipid bilayer membrane, a chemical substance is detected with high sensitivity and high precision. Here, the specific lipid bilayer membrane comprises a chemical substance receptor, a chimeric G protein, and a potassium ion channel. The chimeric G protein comprises a chimeric $G_\alpha$ subunit and a $G_{\beta\gamma}$ subunit complex. The chimeric $G_\alpha$ subunit is selected from the group consisting of $G_{i/olf13}$ (SEQ ID NO: 04), $G_{i/olf28}$ (SEQ ID NO: 05), $G_{i/olf94}$ (SEQ ID NO: 07), $G_{i/olf113}$ (SEQ ID NO: 08), $G_{i/olf\alpha3-\beta5,C}$ (SEQ ID NO: 12), and $G_{i/olf\alpha4-\beta6,C}$ (SEQ ID NO: 15).

6 Claims, 30 Drawing Sheets

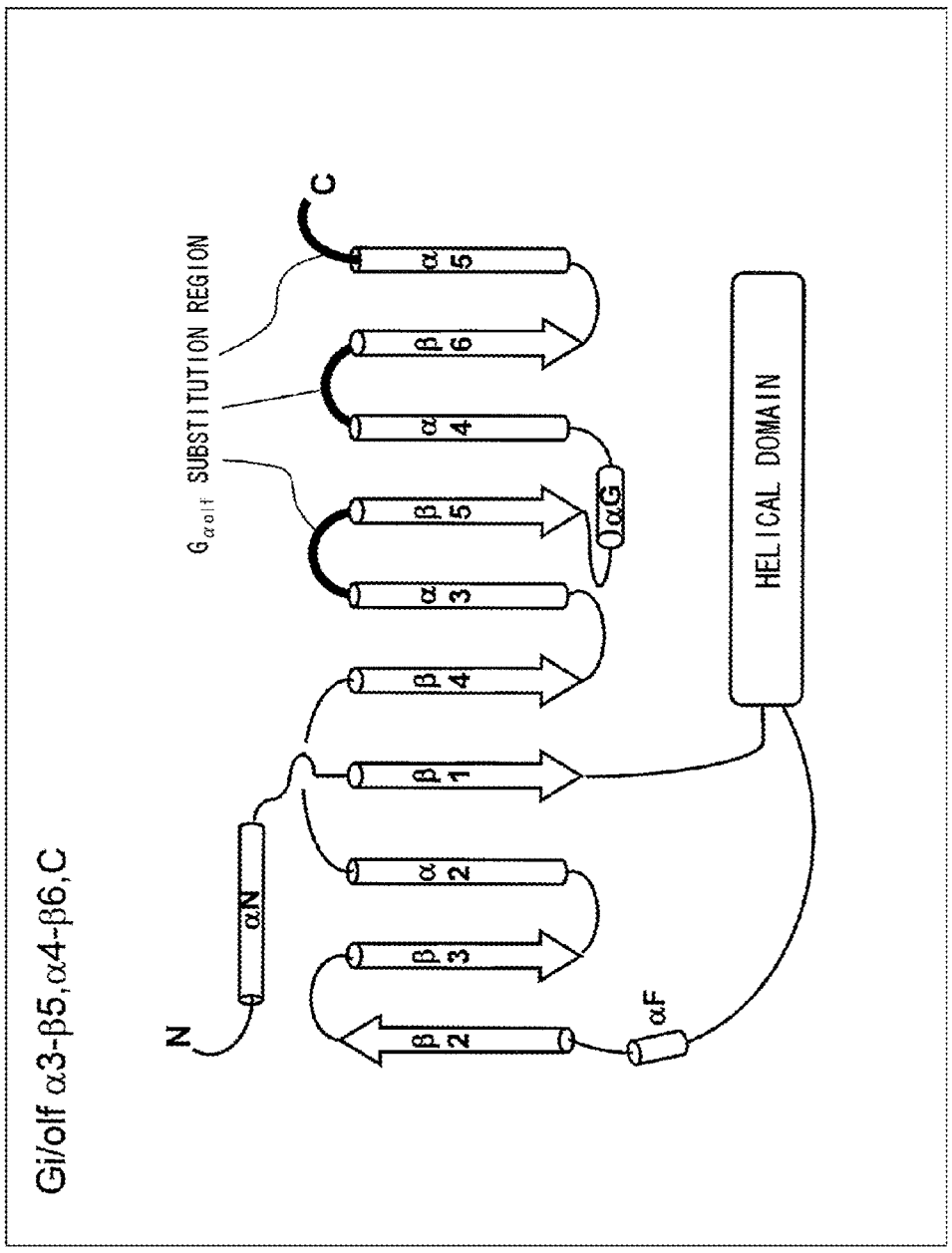

F I G. 2 0
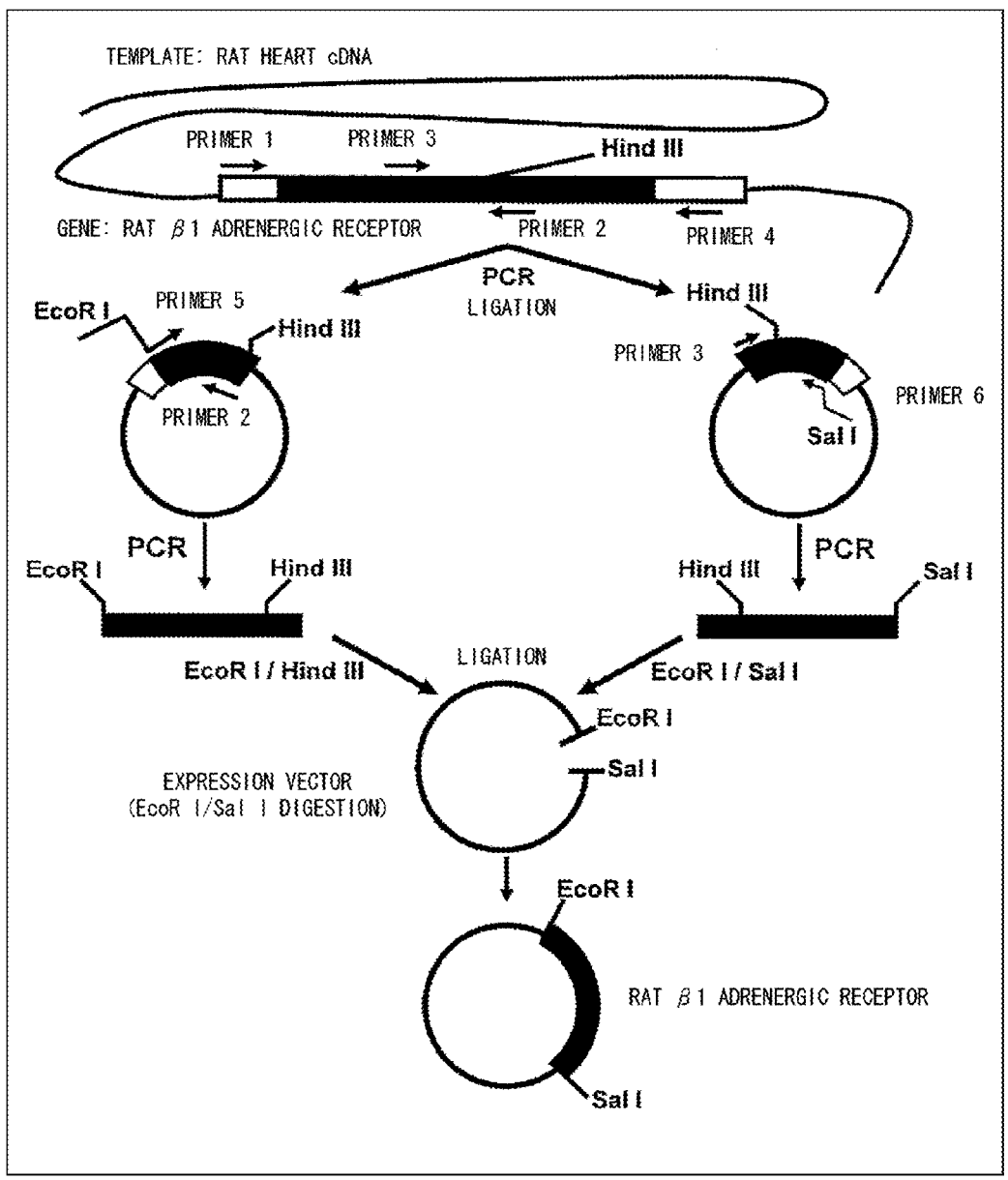

F I G. 2 4
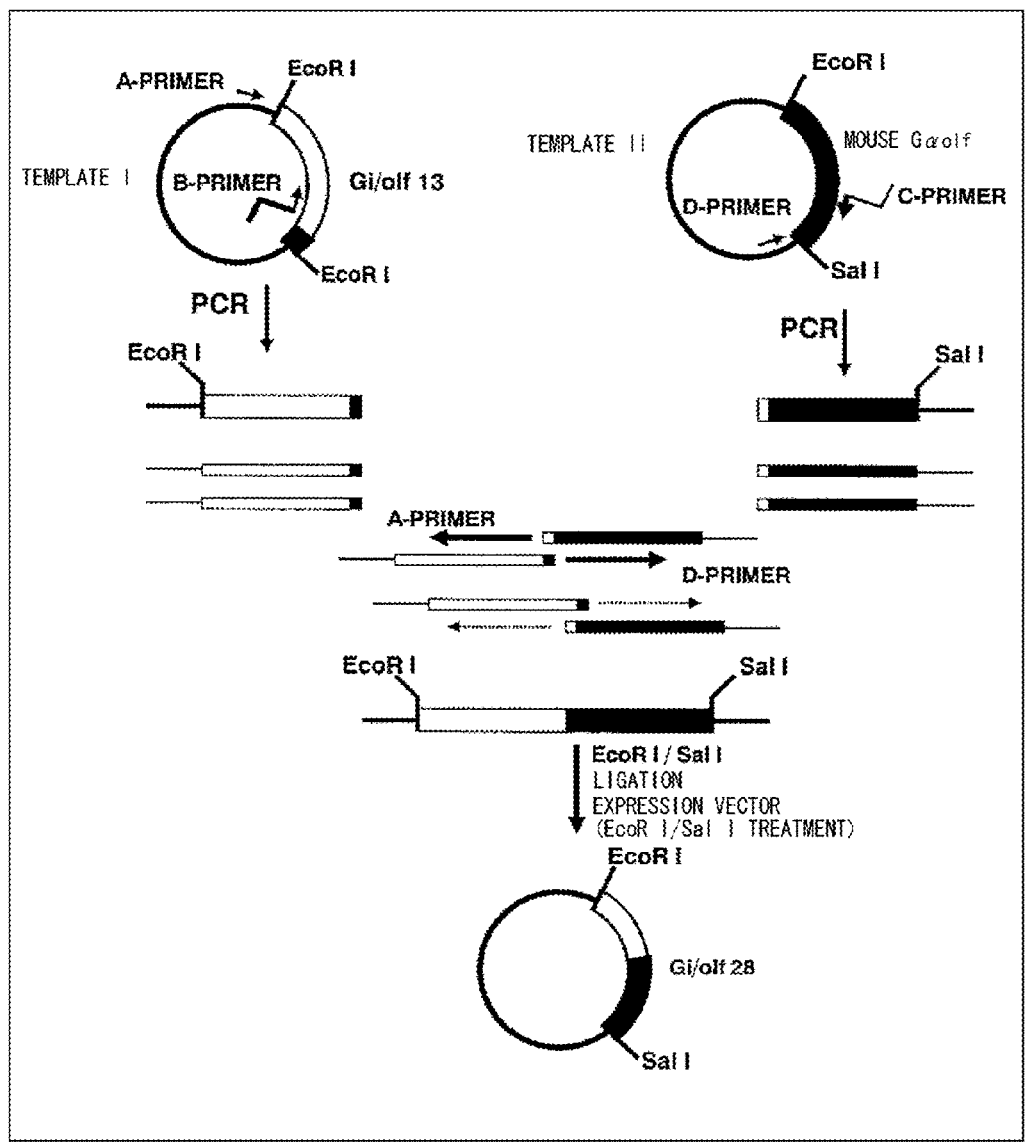

METHOD FOR TRANSPORTING POTASSIUM IONS FROM FRONT SIDE TO BACK SIDE OF LIPID BILAYER MEMBRANE

RELATED APPLICATIONS

This application is a continuation of PCT International Application PCT/JP2011/000375 filed on Jan. 25, 2011, which claims priority to Japanese Patent Application No. 2010-223737 filed on Oct. 1, 2010. The disclosures of these applications including the specifications, the drawings, and the claims are hereby incorporated by reference in their entirety.

BACKGROUND OF THE INVENTION

The Sequence listing in "SEQUENCE LISTING.TXT" created on Oct. 19, 2011, being 64.0 KB in size is incorporated by reference.

FIELD OF THE INVENTION

The present invention relates to a method for transporting potassium ions from a front side of a lipid bilayer membrane to a back side thereof.

DESCRIPTION OF THE BACKGROUND ART

G protein-coupled receptors (hereinafter, abbreviated as "GPCR") existing in lipid bilayer membranes of cells functions in association with G proteins existing in the lipid bilayer membranes of cells. As shown in FIG. 1, when a chemical substance such as a neurotransmitter binds to a GPCR, a trimeric G protein coupled to the GPCR in a cell becomes activated to dissociate into a $G_\alpha$ subunit and a dimer (hereinafter, referred to as a "$G_{\beta\gamma}$ subunit complex") consisting of $G_\beta$ and $G_\gamma$ subunits. Then, each of those transmits various signals.

As shown in FIG. 2, binding of the $G_{\beta\gamma}$ subunit complex to a G protein-coupled inwardly rectifying potassium channel (hereinafter, referred to as "GIRK") causes the GIRK gate to be open. When the GIRK gate is opened, potassium ions existing on a front side of the lipid bilayer membrane move through the gate to a back side of the lipid bilayer membrane. The movement of the potassium ions can be detected or quantified with an ionic current measuring technique.

If the $G_\alpha$ subunit is a chimeric $G_\alpha$ subunit, the potassium ions move from the front side to the back side more efficiently in some cases. It is suggested to use, as a chemical substance sensor, a lipid bilayer membrane where a G protein comprising a chimeric $G_\alpha$ subunit has been expressed.

The following Non-patent Literatures 1 to 6 are relevant to the present invention.

CITATION LIST

Non-Patent Literature

[NPL 1] Gloriam D., Fredriksson R., Schioth H., (2007) "The G protein-coupled receptor subset of the rat genome" BMC Genomics 8, 338-405
[NPL 2] Oldham, W. M. and H. E. Hamm (2008). "Heterotrimeric G protein activation by G-protein-coupled receptors." Nat. Rev. Mol. Cell. Biol. 9, 60-71.
[NPL 3] Kim W. Chan, Jin-Liang Sui, Michel Vivaudou, and Diomedes E. Logothetis, (1996) "Control of channel activity through a unique amino acid residue of a G protein-gated inwardly rectifying K+ channel subunit" Proc. Natl. Acad. Sci., 93, 14193-14198
[NPL 4] Gregory J. Digby, Pooja R. Sethi, and Nevin A. Lambert, (2008), "Differential dissociation of G protein heterotrimers" J. Physiol, 586, 3325-3335
[NPL 5] Thomsen W., Frazer J., Unett D., (2005), "Functional assays for screening GPCR targets" Curr. Opin. Biotech., 16, 655-665
[NPL 6] Leaney J. L., Milligan G., Tinker A., (2000) "The G Protein a Subunit Has a Key Role in Determining the Specificity of Coupling to, but Not the Activation of, G Protein-gated Inwardly Rectifying K1 Channels" J. Biol. Chem., 275, 921-929

Problems to be Solved by the Invention

An object of the present invention is to provide a method for transporting potassium ions from a front side of a lipid bilayer membrane to a back side thereof in a further highly sensitive manner in response to a chemical substance.

Solution to the Problems

The present inventors have discovered that a chimeric G protein comprising a specific chimeric $G_\alpha$ subunit solves the above described problem, and have established the present invention.

Thus, the present invention provides the following items 1 to 9.

Item 1:
A method for transporting potassium ions from a front side of a lipid bilayer membrane to a back side thereof, the method comprising the following steps (a) and (b):
 step (a) of preparing the lipid bilayer membrane, wherein
  the lipid bilayer membrane comprises a receptor of a chemical substance, a G protein, and a potassium ion channel,
  the G protein comprises a chimeric $G_\alpha$ subunit and a $G_{\beta\gamma}$ subunit complex, and
  the chimeric $G_\alpha$ subunit consists of any one of $G_{i/olfi3}$ (SEQ ID NO: 04), $G_{i/olfi28}$ (SEQ ID NO: 05), $G_{i/olf94}$ (SEQ ID NO: 07), $G_{i/olfi13}$ (SEQ ID NO: 08), $G_{i/olf\alpha3-\beta5,C}$ (SEQ ID NO: 12), or $G_{i/olf\alpha4-\beta6,C}$ (SEQ ID NO: 15); and
 step (b) of supplying the chemical substance and the potassium ions to the front side to release the chimeric $G_\alpha$ subunit and $G_{\beta\gamma}$ subunit complex, and to allow the $G_{\beta\gamma}$ subunit complex to bind to the potassium ion channel, and transporting the potassium ions from the front side to the back side.

Item 2:
The method according to item 1, wherein the chemical substance is an adrenergic receptor agonist.

Item 3:
The method according to item 1, wherein the potassium ion channel is a G protein-coupled inwardly rectifying potassium ion channel.

Item 4:
A method for detecting or quantifying a chemical substance, the method comprising the following steps (c), (d), and (e):
 step (c) of preparing a lipid bilayer membrane, a first liquid located on a front side of the lipid bilayer membrane, and a second liquid located on a back side of the lipid bilayer membrane, wherein
  the lipid bilayer membrane comprises a chemical substance receptor, a G protein, and a potassium ion channel, the G protein comprises a chimeric $G_\alpha$ subunit and a $G_{\beta\gamma}$ subunit complex, the chimeric $G_\alpha$ subunit consists of any one of $G_{i/olf13}$ (SEQ ID NO: 04), $G_{i/olf28}$ (SEQ ID NO: 05), $G_{i/olf94}$ (SEQ ID NO: 07), $G_{i/olf113}$ (SEQ ID NO: 08), $G_{i/olf\alpha3\text{-}\beta5,C}$ (SEQ ID NO: 12), or $G_{i/olf\alpha4\text{-}\beta6,C}$ (SEQ ID NO: 15), and the first liquid contains potassium ions;

step (d) of supplying the chemical substance to the first liquid; and step (e) of measuring an amount of potassium ions in at least one of the first and second liquids to detect or quantify the chemical substance based on the amount of the potassium ions.

Item 5:

The method according to item 4, wherein the chemical substance is an adrenergic receptor agonist.

Item 6:

The method according to item 4, wherein the potassium ion channel is a G protein-coupled inwardly rectifying potassium ion channel.

Item 7:

A method for detecting or quantifying a chemical substance, the method comprising the following steps (f), (g), and (h):

step (f) of preparing a lipid bilayer membrane, wherein the lipid bilayer membrane comprises a chemical substance receptor, a G protein, and a potassium ion channel, the G protein comprises a chimeric $G_\alpha$ subunit and a $G_{\beta\gamma}$ subunit complex, and the chimeric $G_\alpha$ subunit consists of any one of $G_{i/olf13}$ (SEQ ID NO: 04), $G_{i/olf28}$ (SEQ ID NO: 05), $G_{i/olf94}$ (SEQ ID NO: 07), $G_{i/olf113}$ (SEQ ID NO: 08), $G_{i/olf\alpha3\text{-}\beta5,C}$ (SEQ ID NO: 12), or $G_{i/olf\alpha4\text{-}\beta6,C}$ (SEQ ID NO: 15);

step (g) of supplying a first liquid and a second liquid located respectively on a front side and a back side of the lipid bilayer membrane such that the lipid bilayer membrane is interposed between the first liquid and second liquid, wherein the first liquid contains potassium ions and the chemical substance; and step (h) of measuring an amount of potassium ions in at least one of the first and second liquids to detect or quantify the chemical substance based on the amount of the potassium ions.

Item 8:

The method according to item 7, wherein the chemical substance is an adrenergic receptor agonist.

Item 9:

The method according to item 7, wherein the potassium ion channel is a G protein-coupled inwardly-rectifying ion channel.

Advantageous Effects of the Invention

The present invention increases an amount of potassium ions transported from a front side of a lipid bilayer membrane to a back side thereof. Thus, a target chemical substance is detected with higher sensitivity.

BRIEF DESCRIPTION OF THE DRAWINGS

FIG. 19 schematically shows a secondary structure of $G_{i/olf\alpha3\text{-}\beta5,\alpha4\text{-}\beta6,C}$.

FIG. 20 illustrates a concept of a method for constructing a β1 adrenergic receptor expression plasmid.

FIG. 24 illustrates a concept of a method for constructing a chimeric G protein expression plasmid.

DESCRIPTION OF THE PREFERRED EMBODIMENTS

Definition of Terms

Figure 1:
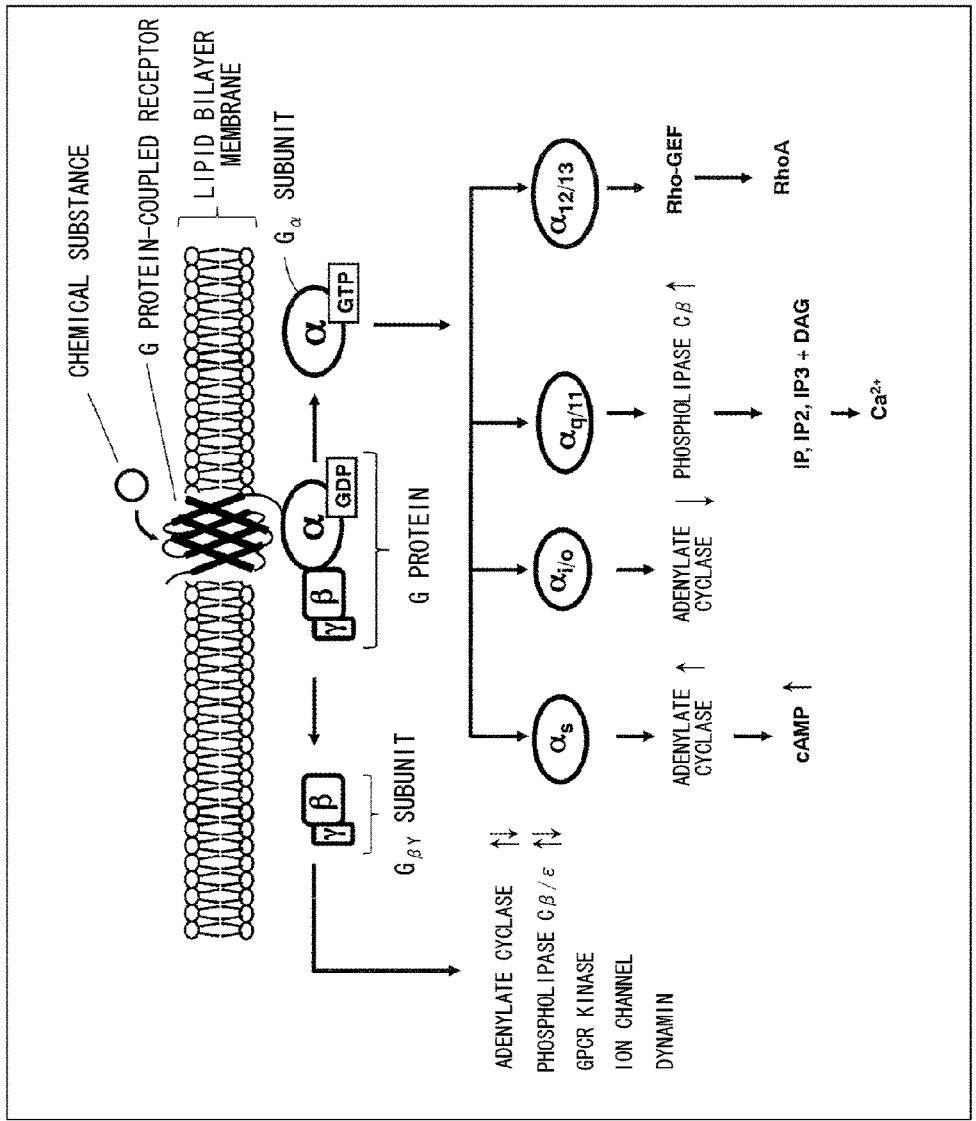
FIG. 1 is a schematic diagram showing signal transduction conducted by a trimeric G protein.
Figure 2:
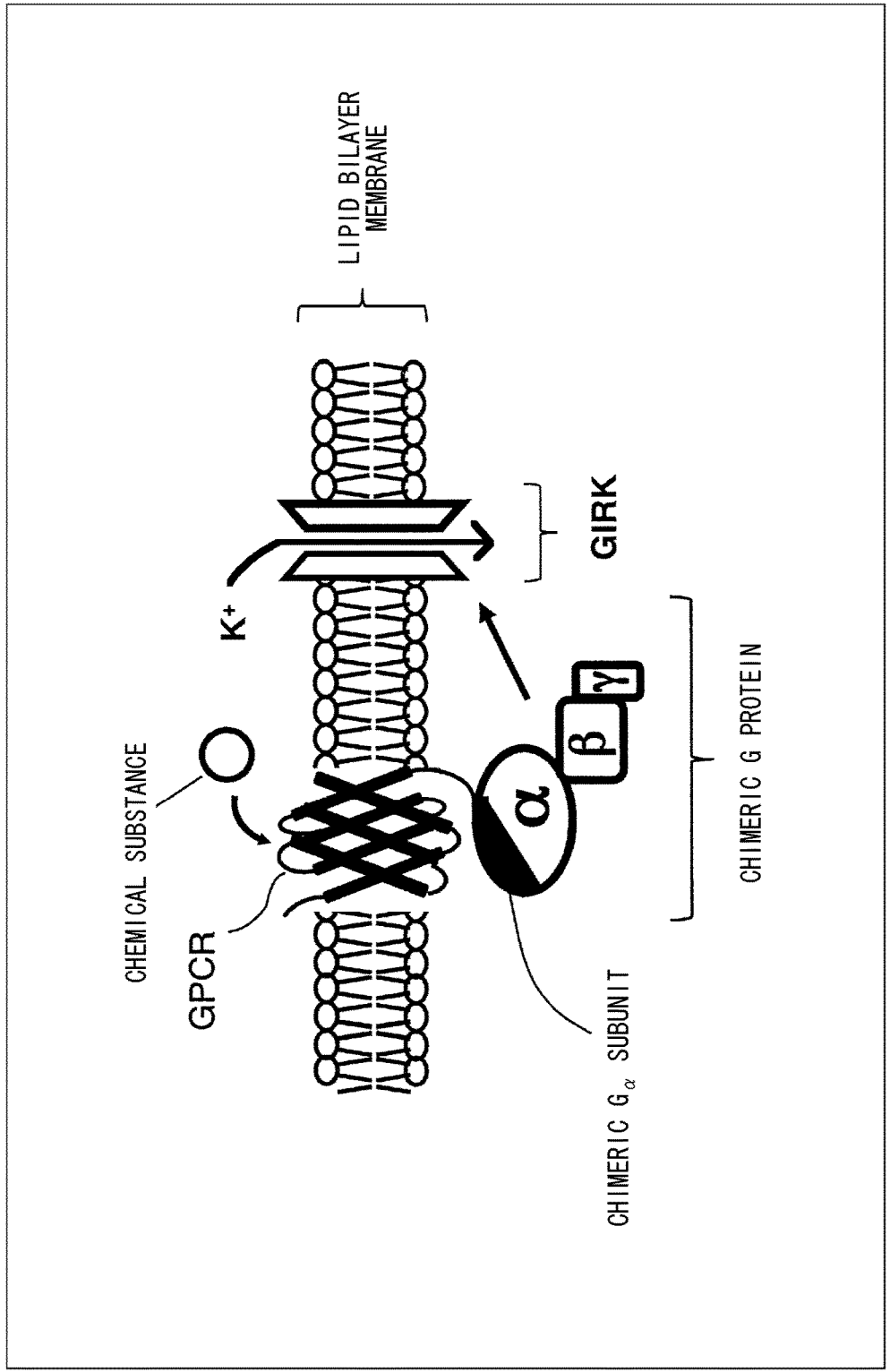
FIG. 2 is a schematic diagram showing a chemical substance sensor utilizing the function of a GIRK.

The terms used in the present specification are defined as follows:

The term "lipid bilayer membrane" refers to a membrane forming a surface of a cell, i.e., a cell membrane.

The term "chimeric $G_\alpha$ subunit" refers to a $G_\alpha$ subunit in which a region of the original $G_\alpha$ subunit (e.g., $G_{\alpha i}$) is substituted with a corresponding region of a different $G_\alpha$ protein (e.g., $G_{\alpha olf}$).

The term "chimeric G protein" refers to a G protein in which the α subunit thereof is a chimeric $G_\alpha$ subunit.

The lipid bilayer membrane used in the present invention comprises a chemical substance receptor, a chimeric G protein, and a potassium ion channel.

An example of cells having the lipid bilayer membrane is an established cell line derived from a human cell.

(Chemical Substance Receptor)

A G protein-coupled receptor is employed as a chemical substance receptor. G protein-coupled receptors include hormone receptors, neurotransmitter receptors, pheromone receptors, olfactory receptors and gustatory receptors, as well as various orphan G protein-coupled receptors. Examples of the hormone receptors are adrenergic receptors.

(Chimeric G Protein)

A chimeric G protein comprises a chimeric $G_\alpha$ subunit and a $G_{\beta\gamma}$ subunit complex.

In the present invention, the chimeric $G_\alpha$ subunit is selected from the group consisting of $G_{i/olfi3}$, $G_{i/olfi28}$, $G_{i/olfi94}$, $G_{i/olfi113}$, $G_{i/olf\alpha3-\beta5,C}$, and $G_{i/olf\alpha4-\beta6,C}$. Subscripts included in the names of the chimeric $G_\alpha$ subunits indicate $G_{\alpha i}$ protein domains in which amino acid sequences thereof are substituted with corresponding amino acid sequences of $G_{\alpha olf}$. When these chimeric $G_\alpha$ subunits are used, a larger amount of potassium ions are transported from a front side of the lipid bilayer membrane to a back side thereof in response to contact with the chemical substance. The amino acid sequences of each of the chimeric $G_\alpha$ subunits are shown below.

($G_{i/olfi3}$)

(SEQ ID NO: 04)

MGCTLSAEDKAAVERSKMIDRNLREDGEKAAREVKLLLLGAGESGKSTIVKQMKIIHEA

GYSEEECKQYKAVVYSNTIQSIIAIIRAMGRLKIDFGDSARADDARQLFVLAGAAEEGFM

TAELAGVIKRLWKDSGVQACFNRSREYQLNDSAAYYLNDLDRIAQPNYIPTQQDVLRT

RVKTTGIVETHFTFKDLHFKMFDVGGQRSERKKWIHCFEGVTAIIFCVALSDYDLVLAE

DEEMNRMHESMKLFDSICNNKWFTDTSIILFLNKKDLFEEKIKKSPLTICYPEYAGSNTY

EEAAAYIQCQFEDLNKRKDTKEIYTHFTCATDTKNVQFVFDAVTDIIQRMHLKQYELL ($G_{i/olfi28}$)

(SEQ ID NO: 05)

MGCTLSAEDKAAVERSKMIDRNLREDGEKAAREVKLLLLGAGESGKSTIVKQMKIIHEA

GYSEEECKQYKAVVYSNTIQSIIAIIRAMGRLKIDFGDSARADDARQLFVLAGAAEEGFM

TAELAGVIKRLWKDSGVQACFNRSREYQLNDSAAYYLNDLDRIAQPNYIPTQQDVLRT

RVKTTGIVETHFTFKDLHFKMFDVGGQRSERKKWIHCFEGVTAIIFCVALSDYDLVLAE

DEEMNRMHESMKLFDSICNNKWFTDTSIILFLNKKDLFEEKIKKSPLTICYPEYAGSNTY

EEAAAYIQCQFEDLNKRKDTKEIYTHFTCAVDTENIRRVFNDCRDIIQRMHLKQYELL ($G_{i/olfi94}$)

(SEQ ID NO: 07)

MGCTLSAEDKAAVERSKMIDRNLREDGEKAAREVKLLLLGAGESGKSTIVKQMKIIHEA

GYSEEECKQYKAVVYSNTIQSIIAIIRAMGRLKIDFGDSARADDARQLFVLAGAAEEGFM

TAELAGVIKRLWKDSGVQACFNRSREYQLNDSAAYYLNDLDRIAQPNYIPTQQDVLRT

RVKTTGIVETHFTFKDLHFKMFDVGGQRSERKKWIHCFEGVTAIIFCVALSDYDLVLAE

DEEMNRMHESMKLFDSICNNKWFTDTSIILFLNKKDLFEEKVLAGKSKIEDYFPEYANY

TVPEDATPDAGEDPKVTRAKFFIRDLFLRISTATGDGKHYCYPHFTCAVDTENIRRVFND

CRDIIQRMHLKQYELL ($G_{i/olfi113}$)

(SEQ ID NO: 08)

MGCTLSAEDKAAVERSKMIDRNLREDGEKAAREVKLLLLGAGESGKSTIVKQMKIIHEA

GYSEEECKQYKAVVYSNTIQSIIAIIRAMGRLKIDFGDSARADDARQLFVLAGAAEEGFM

TAELAGVIKRLWKDSGVQACFNRSREYQLNDSAAYYLNDLDRIAQPNYIPTQQDVLRT

RVKTTGIVETHFTFKDLHFKMFDVGGQRSERKKWIHCFEGVTAIIFCVALSDYDLVLAE

DEEMNRMHESMKLFDSICNNKWLRTISIILFLNKQDMLAEKVLAGKSKIEDYFPEYANY

TVPEDATPDAGEDPKVTRAKFFIRDLFLRISTATGDGKHYCYPHFTCAVDTENIRRVFND

CRDIIQRMHLKQYELL

-continued ($G_{i/olfα3-β5,C}$)
(SEQ ID NO: 12)
MGCTLSAEDKAAVERSKMIDRNLREDGEKAAREVKLLLLGAGESGKSTIVKQMKIIHEA

GYSEEECKQYKAVVYSNTIQSIIAIIRAMGRLKIDFGDSARADDARQLFVLAGAAEEGFM

TAELAGVIKRLWKDSGVQACFNRSREYQLNDSAAYYLNDLDRIAQPNYIPTQQDVLRT

RVKTTGIVETHFTFKDLHFKMFDVGGQRSERKKWIHCFEGVTAIIFCVALSDYDLVLAE

DEEMNRMHESMKLFDSICNNKWLRTISIILFLNKKDLFEEKIKKSPLTICYPEYAGSNTYE

EAAAYIQCQFEDLNKRKDTKEIYTHFTCATDTKNVQFVFDAVTDIIQRMHLKQYELL ($G_{i/olfα4-β6,C}$)
(SEQ ID NO: 15)
MGCTLSAEDKAAVERSKMIDRNLREDGEKAAREVKLLLLGAGESGKSTIVKQMKIIHEA

GYSEEECKQYKAVVYSNTIQSIIAIIRAMGRLKIDFGDSARADDARQLFVLAGAAEEGFM

TAELAGVIKRLWKDSGVQACFNRSREYQLNDSAAYYLNDLDRIAQPNYIPTQQDVLRT

RVKTTGIVETHFTFKDLHFKMFDVGGQRSERKKWIHCFEGVTAIIFCVALSDYDLVLAE

DEEMNRMHESMKLFDSICNNKWFTDTSIILFLNKKDLFEEKIKKSPLTICYPEYAGSNTY

EEAAAYIQCQFEDLNTATGDGKHYCYTHFTCATDTKNVQFVFDAVTDIIQRMHLKQYE

LL

Figure 3:
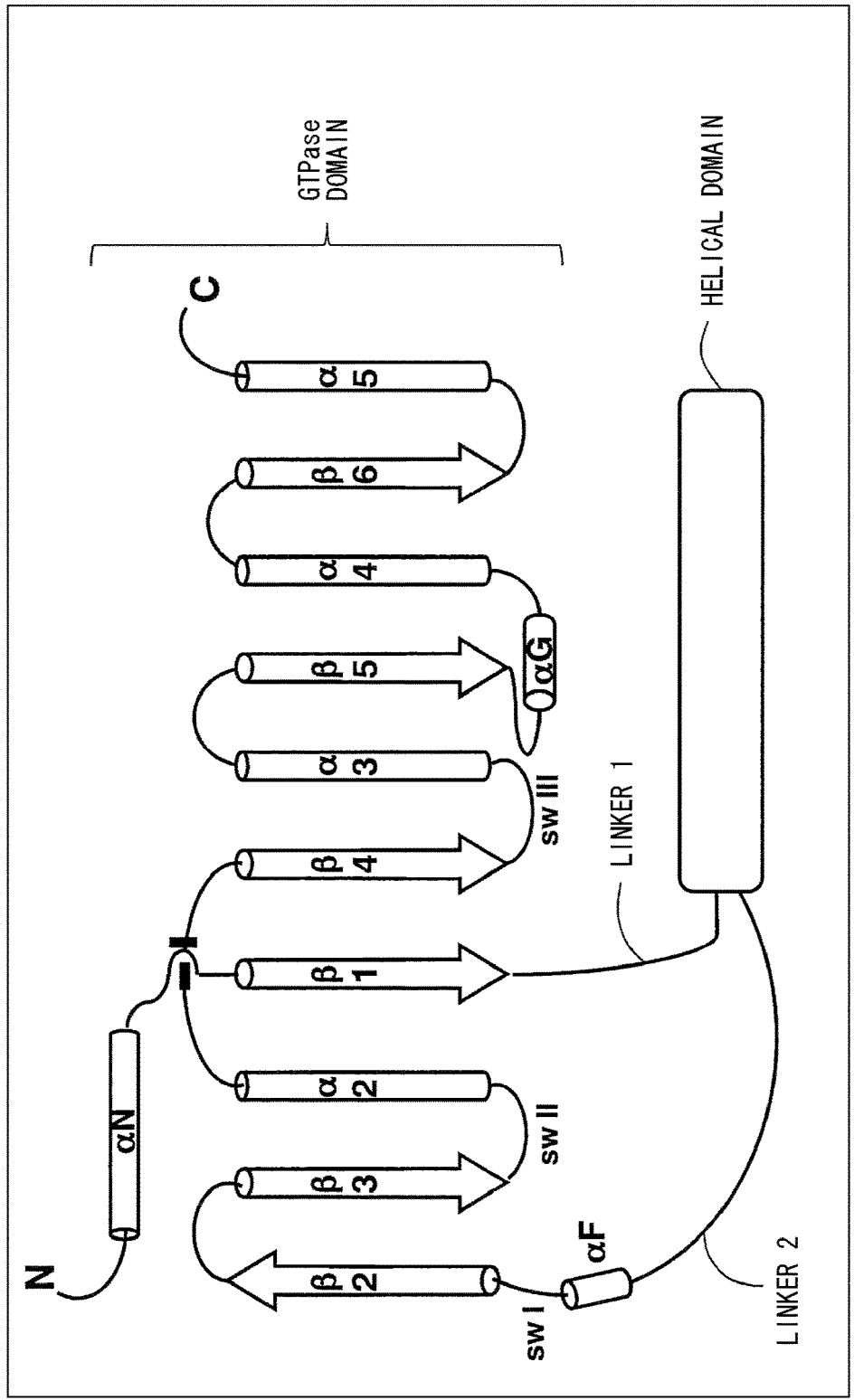
FIG. 3 is a schematic diagram showing a secondary structure of a G protein.

As shown in FIG. 3, a protein forming a $G_α$ subunit comprises a domain referred to as a GTPase domain and a domain referred to as a helical domain. Both domains are linked to each other via two α-helixes referred to as linker 1 and linker 2. The GTPase domain includes five α-helixes, six β-sheets, and loops connecting those.

Figure 7:
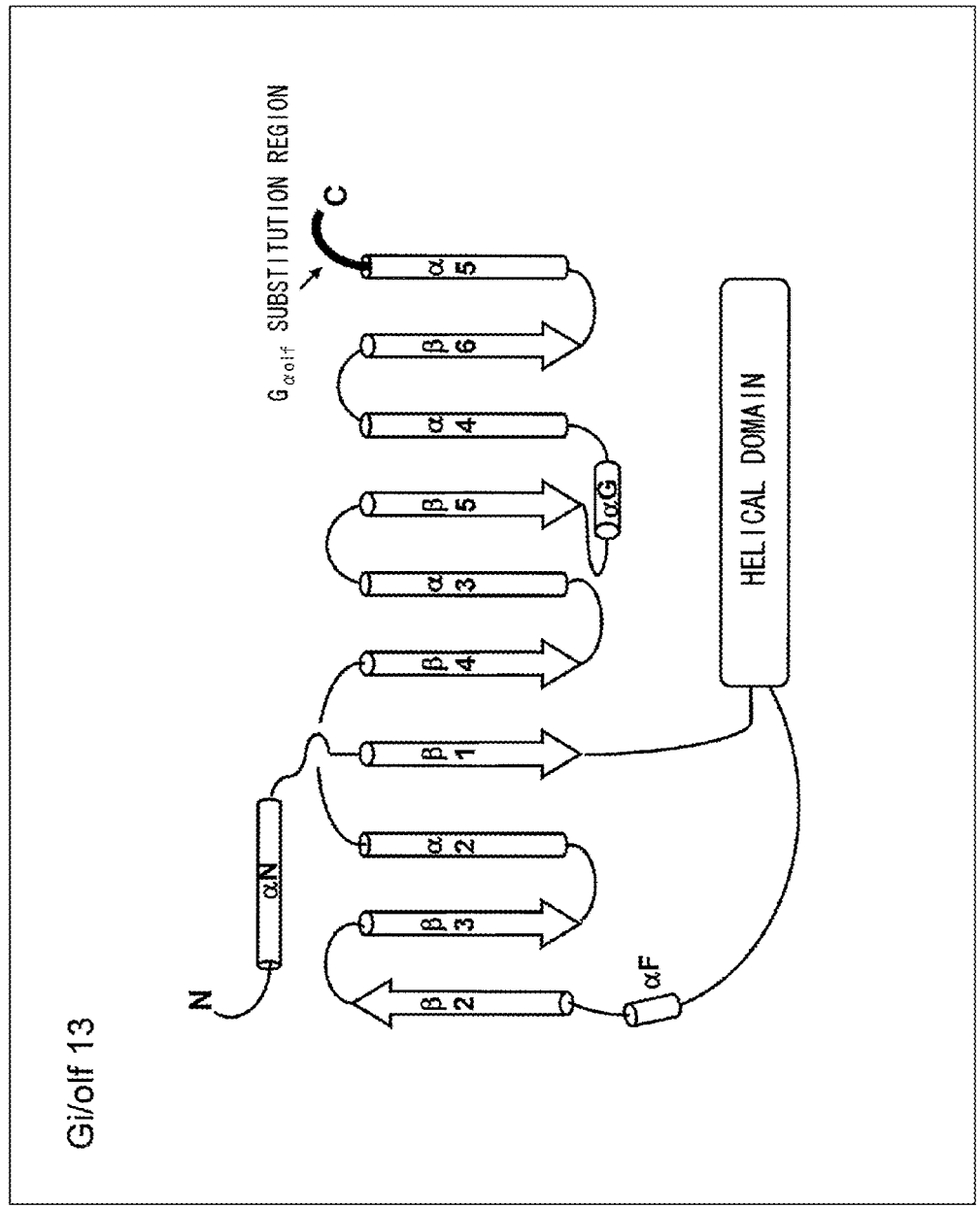
FIG. 7 schematically shows a secondary structure of $G_{i/olf13}$.

As shown in FIG. 7, the secondary structure of $G_{i/olfl3}$ is a structure in which 13 amino acids of the C-terminal of $G_{αi}$ (C351G) are substituted with corresponding amino acids of $G_{αolf}$.

Figure 8:
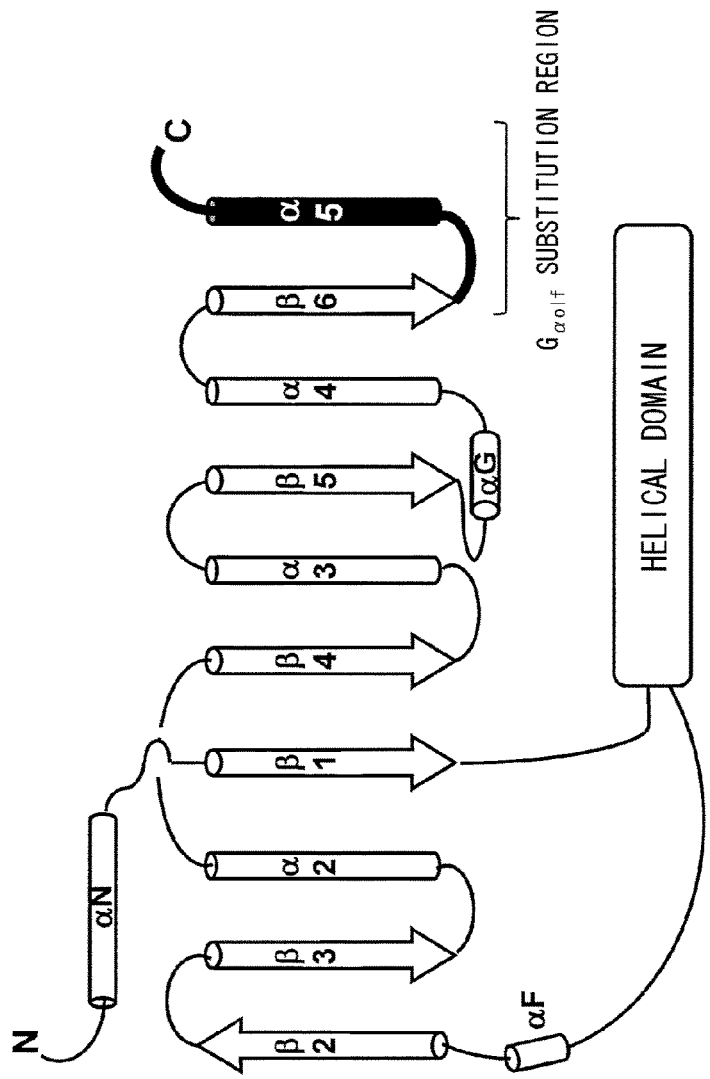
FIG. 8 schematically shows a secondary structure of $G_{i/olf28}$.

As shown in FIG. 8, the secondary structure of $G_{i/olfβ28}$ is a structure in which the region located at the C-terminal side including β6-α5 loop of $G_{αi}$ (C351G) is substituted with a corresponding region of $G_{αolf}$.

Figure 10:
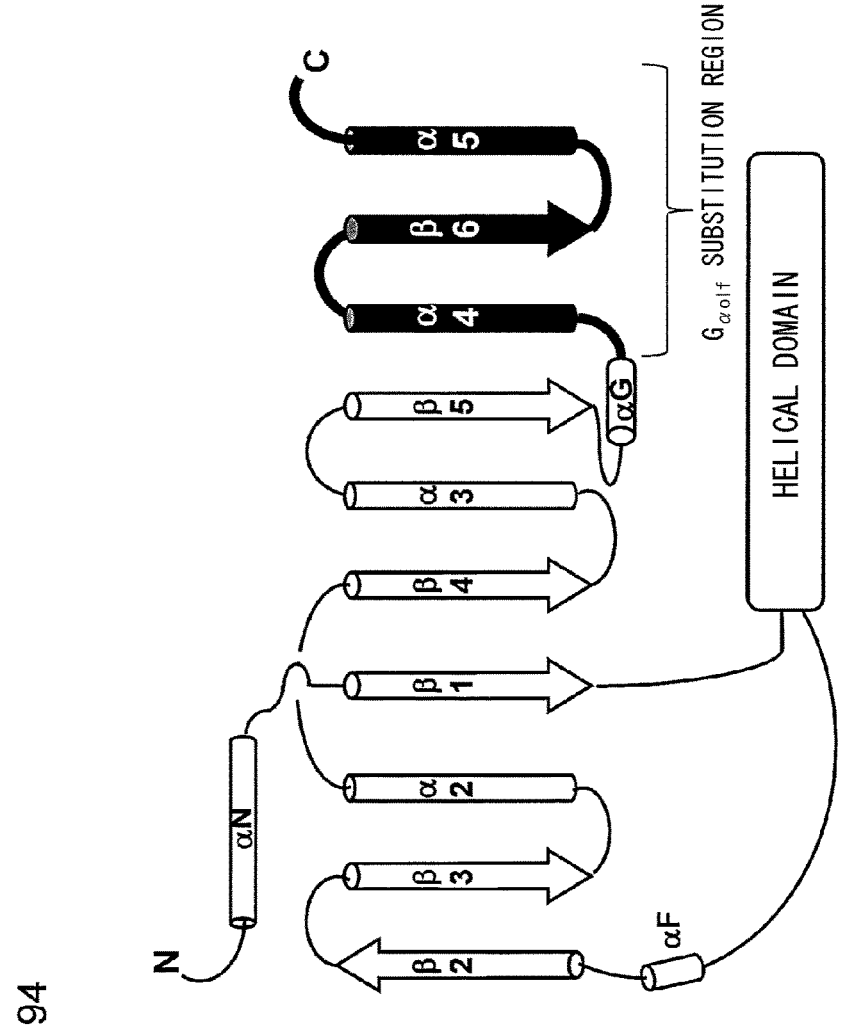
FIG. 10 schematically shows a secondary structure of $G_{i/olf94}$.

As shown in FIG. 10, the secondary structure of $G_{i/olfβ4}$ is a structure in which the region located at the C-terminal side including αG-α4 loop of $G_{αi}$ (C351G) is substituted with a corresponding region of $G_{αolf}$.

Figure 11:
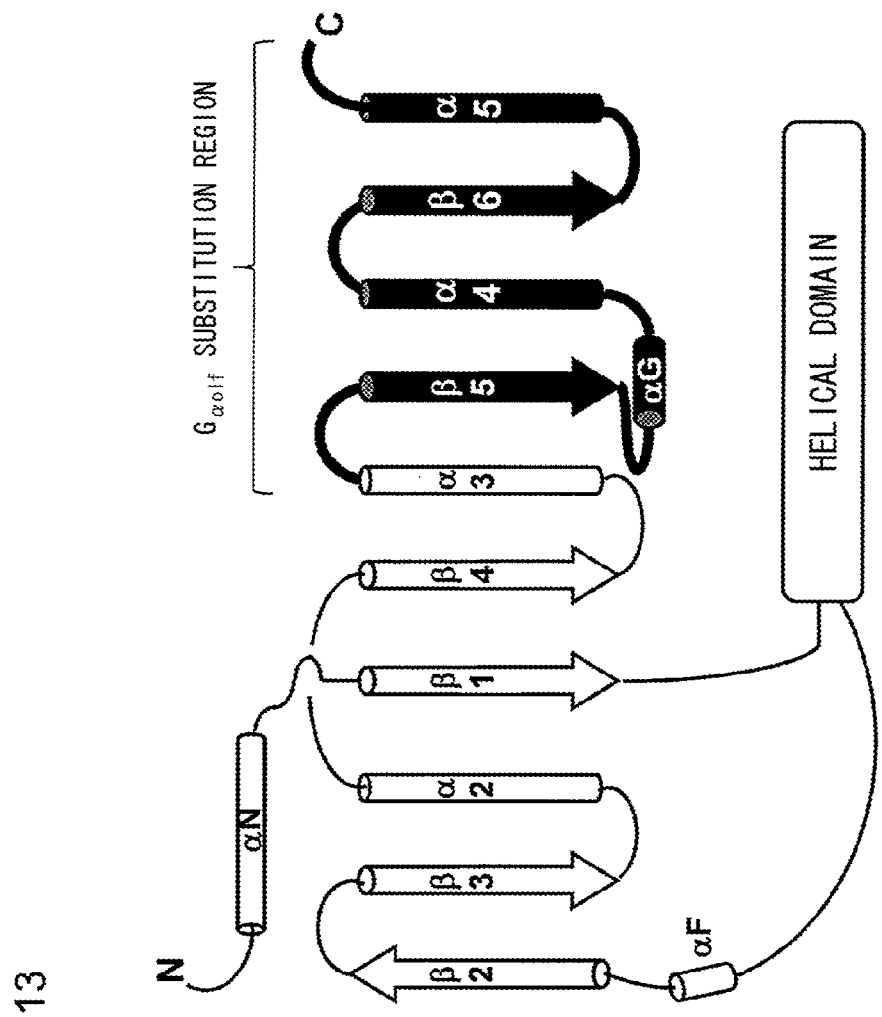
FIG. 11 schematically shows a secondary structure of $G_{i/olf113}$.

As shown in FIG. 11, the secondary structure of $G_{i/olfl13}$ is a structure in which the region located at the C-terminal side including α3-β5 loop of $G_{αi}$ (C351G) is substituted with a corresponding region of $G_{αolf}$.

Figure 15:
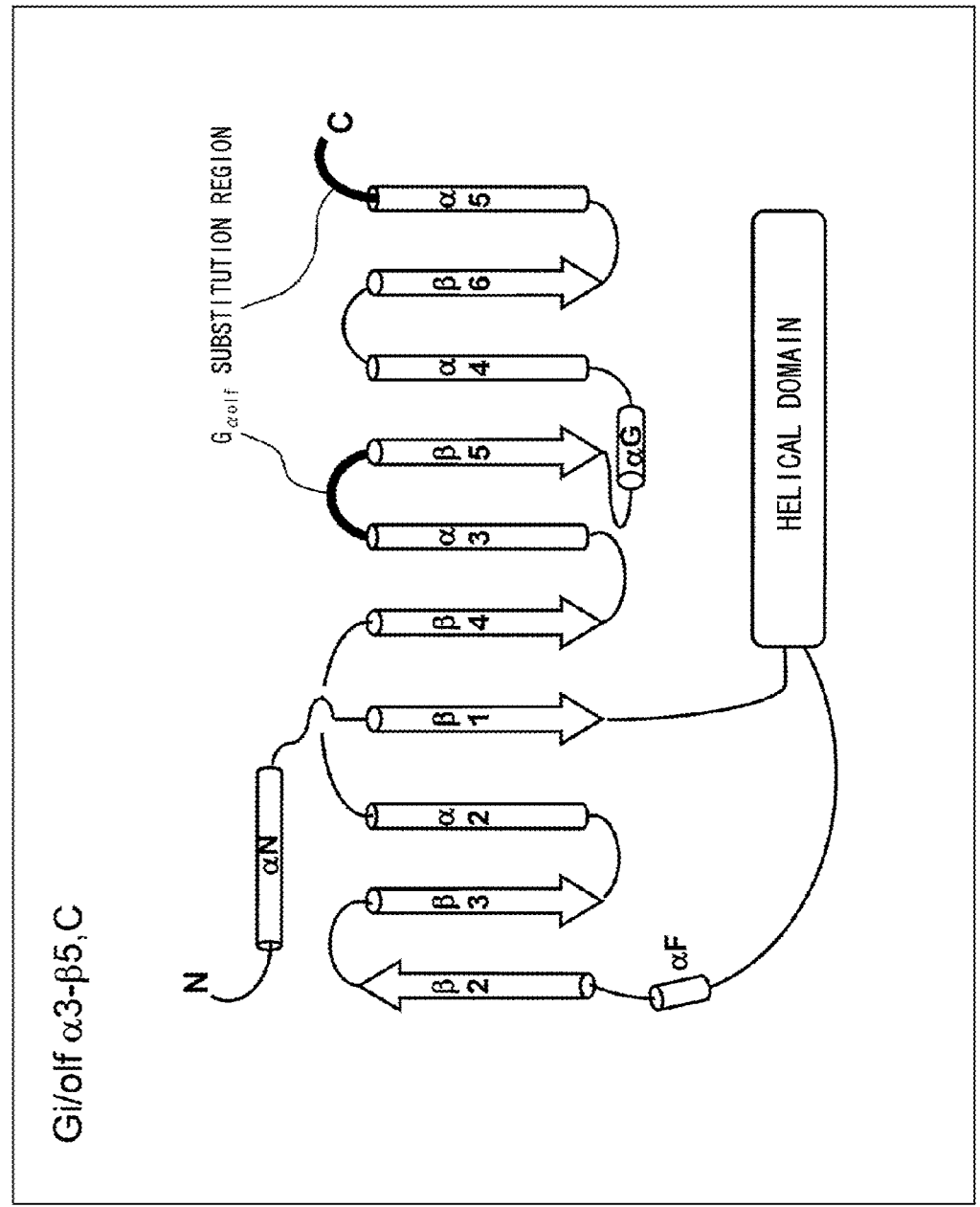
FIG. 15 schematically shows a secondary structure of $G_{i/olf\alpha3\text{-}\beta5,C}$.

As shown in FIG. 15, the secondary structure of $G_{i/olfα3-β5,C}$ is a structure in which α3-β5 loop and α5-C-terminal loop of $G_{αi}$ (C351G) are substituted with corresponding loops of $G_{αolf}$.

Figure 18:
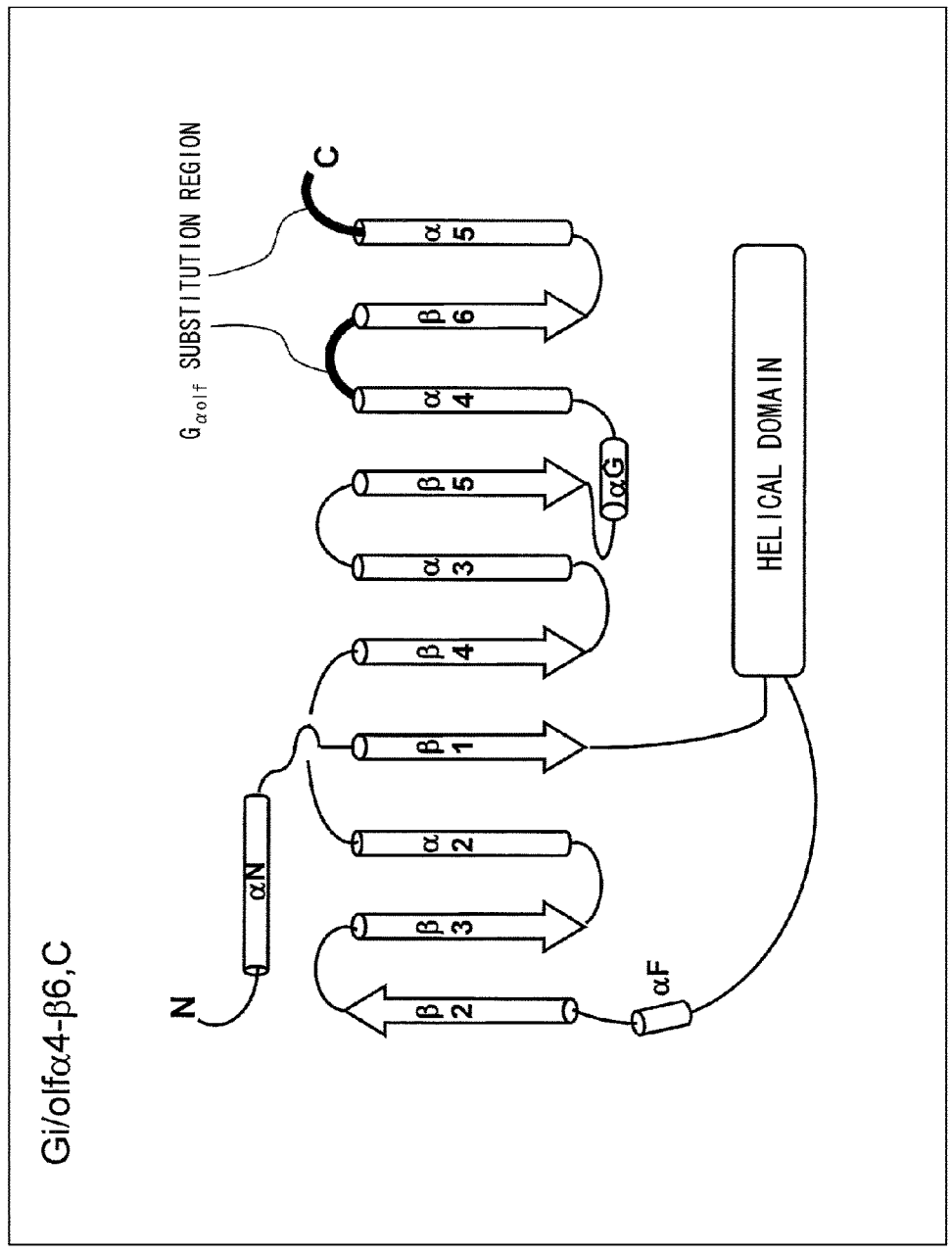
FIG. 18 schematically shows a secondary structure of $G_{i/olf\alpha4\text{-}\beta6,C}$.

As shown in FIG. 18, the secondary structure of $G_{i/olfα4-β6,C}$ is a structure in which α3-β5 loop and α5-C-terminal loop of $G_{αi}$ (C351G) are substituted with corresponding loops of $G_{αolf}$.

(Potassium Ion Channel)

As potassium ion channels, G protein-coupled inwardly rectifying potassium channels (GIRKs) are used. The GIRKs are classified into four subtypes, Kir3.1, Kir3.2, Kir3.3 and Kir3.4. In the present invention, preferably used is a mutated form of Kir3.1, i.e., Kir3.1 (F137S) in which phenylalanine at position 137 of Kir3.1 is substituted with serine. The reason is described below. Each of the subtypes Kir3.1 to Kir3.4 assembles with a different subtype to form a heteromultimer. In other words, a GIRK includes two types of the subtypes. However, the mutated form Kir3.1 (F137S) assembles into a homotetramer, and the tetramer constitutes a potassium ion channel. Therefore, when the mutated form Kir3.1 (F137S) is used, the single type of protein is required for forming a potassium ion channel.

The lipid bilayer membrane comprising the chemical substance receptor, the chimeric G protein and the potassium ion channel, is prepared, for example, by a method described below. An expression plasmid coding for the chemical substance receptor, an expression plasmid coding for the chimeric G protein, and an expression plasmid coding for the potassium ion channel are constructed. Each of the constructed plasmids is introduced into cells and is expressed. Specific procedure of the method is described in detail in the examples.

(Potassium Ion Transport)

A front side and a back side of the lipid bilayer membrane comprising the chemical substance receptor, the chimeric G protein and the potassium ion channel, are each in contact with appropriate buffer solutions.

When the chemical substance is supplied to the front side of the lipid bilayer membrane and binds to the chemical substance receptor, the chimeric G protein bound to the chemical substance receptor on the back side of the lipid bilayer membrane is divided into and released as a chimeric $G_α$ subunit and a $G_{βγ}$ subunit complex. Contact of the $G_{βγ}$ subunit complex to the potassium ion channel leads to opening of a gate of the potassium ion channel. When the gate of the potassium ion channel is opened, potassium ions are transported from the front side to the back side of the lipid bilayer membrane.

(Detection or Quantification of Chemical Substance)

The chemical substance can be detected or quantified by using the above described method of transporting potassium ions from the front side to the back side of the lipid bilayer membrane. A change in ionic current caused by the potassium ion transport is measured to detect or quantify the chemical substance existing on the front side of the lipid bilayer membrane. More particularly, the chemical substance is detected or quantified as described below. First, potassium ions are supplied to the front side of the lipid bilayer membrane comprising the chemical substance receptor, the chimeric G protein and the potassium ion channel described above. More particularly, for example, a first liquid is supplied to the front side of the lipid bilayer membrane, and a second liquid is supplied to the back side of the lipid bilayer membrane. Thus, the lipid bilayer membrane is interposed between the first liquid and the second liquid. Generally, the first liquid and the second liquid are buffer solutions having a pH of around 7. The first liquid contains potassium ions. The second liquid may also contain potassium ions.

A target chemical substance is also supplied on the front side of the lipid bilayer membrane. More particularly, the target chemical substance is supplied to the first liquid in a state where the lipid bilayer membrane is interposed between the first liquid and the second liquid. The target chemical substance is supplied to the chemical substance receptor. Supply of the target chemical substance to the chemical substance receptor causes the subunits of the chimeric G protein to be released. This gives rise to the transport of potassium ions (contained in the first liquid) locating in the front side of the lipid bilayer membrane to the back side (the second liquid) thereof. The change in ionic current generated by the potassium ion transport is measured to detect or quantify the chemical substance on the basis of the measurement result. The above-described supply of the chemical substance may be conducted with a solution instead of the first fluid, where the solution has the same composition as that of the first fluid except for containing an additional chemical substance.

Generally, a standard curve is used to quantify a chemical substance.

(Chemical Substance)

Any chemical substance capable of functioning as an agonist of the chemical substance receptor can be used as the chemical substance, and there is no particular limitation in the chemical substance. If an adrenergic receptor is used as the chemical substance receptor, the chemical substance includes, for example, isoproterenol, dopamine, and dobutamine.

EXAMPLES

Construction of Plasmids

Methods for constructing plasmids used in the Examples and Comparative Examples are shown below.

(Construction of Adrenergic Receptor Expression Plasmid)

FIG. 20 shows a procedure to construct an adrenergic receptor expression plasmid. The gene of a β adrenergic receptor (GenBank Accession Number: J05561.1) was amplified in accordance with the following procedure. Rat heart-derived cDNA (rat heart cDNA) was amplified as two separate fragments by PCR methods. Primers used to amplify one of the fragments were primer 1 (SEQ ID NO: 17) and primer 2 (SEQ ID NO: 18). Primers used to amplify the other fragment were primer 3 (SEQ ID NO: 19) and primer 4 (SEQ ID NO: 20). Each of the obtained two fragments was ligated into a plasmid. PCRs were performed by using these two plasmids as templates. Primers used to amplify one of the plasmids were primer 5 (SEQ ID NO: 21) and primer 2 (SEQ ID NO: 18). Primers used to amplify the other plasmid were primer 3 (SEQ ID NO: 19) and primer 6 (SEQ ID NO: 22). As a result, restriction enzyme sites were added to the ends of the amplified fragments. One of the two obtained fragments was treated with EcoRI and HindIII. The other one was treated with HindIII and SalI. The treated fragments were ligated into an expression plasmid pretreated with EcoRI and SalI to obtain a β1 adrenergic receptor expression plasmid (hereinafter, referred to as "plasmid (βAR)").

Table 1 shows sequences of the used primers.

TABLE 1

| | Sequence | SEQ ID NO: |
|---|---|---|
| Primer 1 | atgggcgcggggcgctcg | 17 |
| Primer 2 | gaagacgaagaggcgatccggcaccagg | 18 |
| Primer 3 | cactgggcatcatcatgggtgtgttcac | 19 |
| Primer 4 | ctacaccttggactcggaggagaagcc | 20 |
| Primer 5 | ttcgaattcgccac-catgggcgcggggcgct | 21 |
| Primer 6 | gaagtcgacctacaccttggactcggagg | 22 |

(Construction of Mutated Potassium Ion Channel Kir3.1 (F137S) Expression Plasmid)

Figure 21:
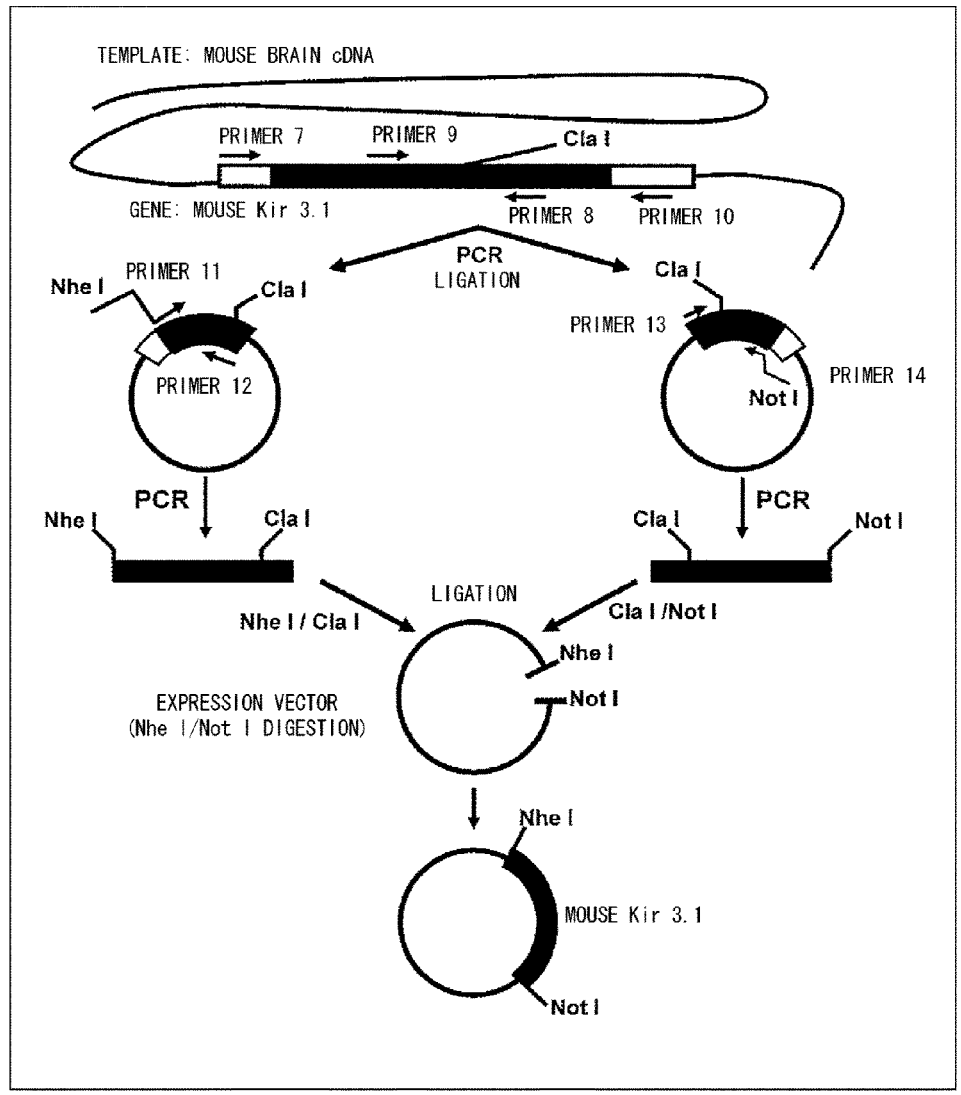
FIG. 21 illustrates a concept of a method for constructing a Kir3.1 expression plasmid.

The gene of a mutated potassium ion channel Kir3.1 (F137S) was constructed by partially mutating the mouse Kir3.1 gene. FIG. 21 shows a procedure to construct a mouse Kir3.1 expression plasmid. The mouse Kir3.1 gene was amplified in two separate fragments. Mouse Brain cDNA Library (Clontech Laboratories, Inc.) was used as a template. Primers used in the first round of PCR to amplify one of the fragments were primer 7 (SEQ ID NO: 23) and primer 8 (SEQ ID NO: 24). Primers used to amplify the other fragment were primer 9 (SEQ ID NO: 25) and primer 10 (SEQ ID NO: 26). Primers used to amplify one of the fragments in the second round of PCR were primer 11 (SEQ ID NO: 27) and primer 12 (SEQ ID NO: 28). Nhe I and Cla I were used as restriction enzymes to cut out a PCR product. Primers used to amplify the other fragment were primer 13 (SEQ ID NO: 29) and primer 14 (SEQ ID NO: 30). Cla I and Not I were used as restriction enzymes to cut out a PCR product. The obtained gene fragments were ligated into an expression plasmid pretreated with Nhe I and Not I to obtain a mouse Kir3.1 expression plasmid (hereinafter, referred to as "plasmid (Kir3.1)").

Table 2 shows sequences of the used primers.

TABLE 2

| | Sequence | SEQ ID NO: |
|---|---|---|
| Primer 7 | gcgcctccgcttcgtgtttgaatctggc | 23 |
| Primer 8 | gccttccaggatgacgacaacctcgaac | 24 |
| Primer 9 | ccgggtgggcaacctgcgcaacagcc | 25 |
| Primer 10 | gccaggctaggatagacctctcag | 26 |
| Primer 11 | gcgctagcgccaccatgtctgcactccgaa | 27 |
| Primer 12 | ggcatcgatcacgtggcaaattgtgagagg | 28 |
| Primer 13 | gtgatcgatgccaaaagcccccttctatgac | 29 |
| Primer 14 | gcgcggccgcctatgtgaaacggtcagag | 30 |

Figure 22:
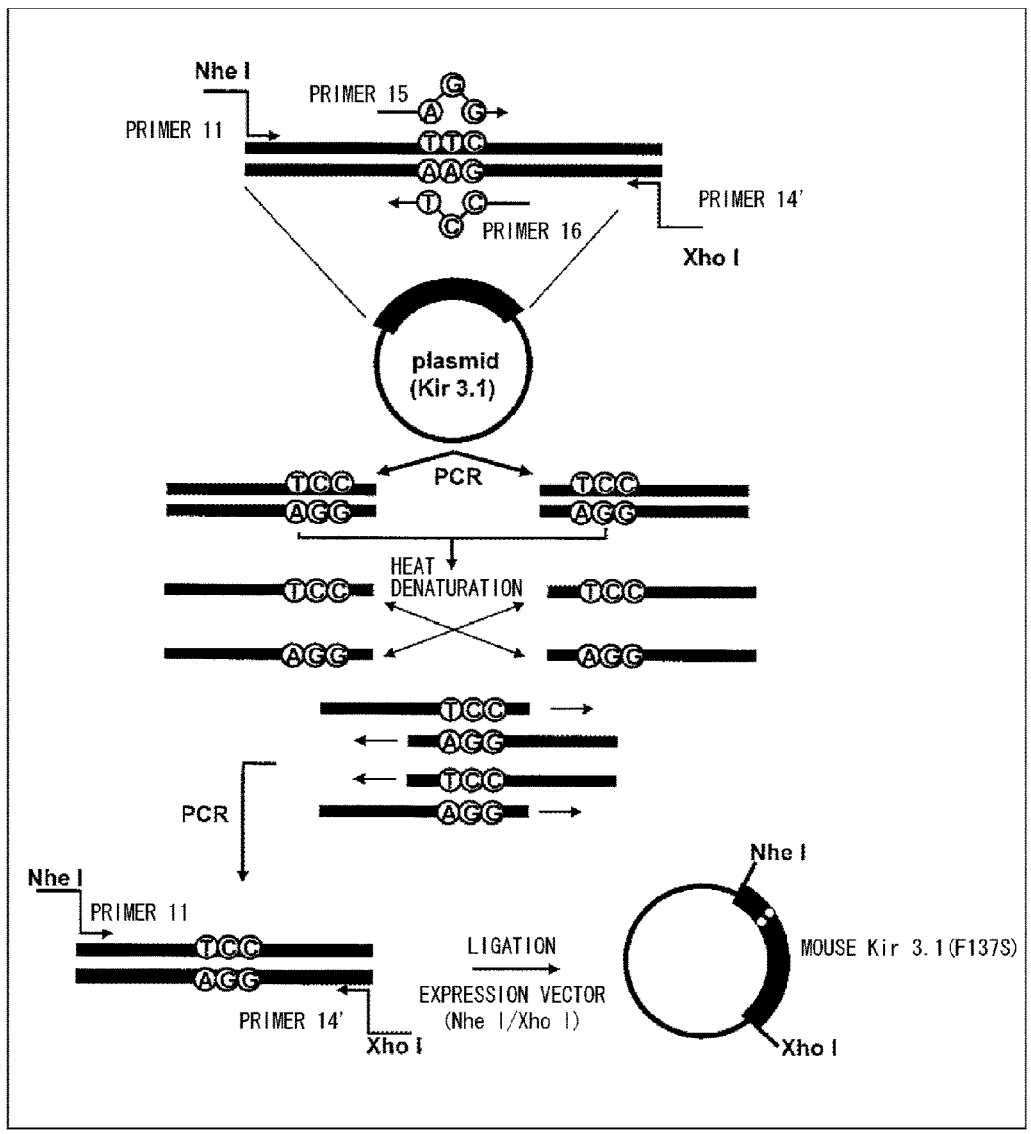
FIG. 22 illustrates a concept of a method for constructing a Kir3.1 (F137S) expression plasmid.

FIG. 22 shows a procedure to construct a mutated potassium ion channel Kir3.1 (F137S) expression plasmid. The Kir3.1 (F137S) gene was constructed by the following procedure. By using the plasmid (Kir3.1) as a template, the Kir3.1 gene was amplified as two fragments. These fragments were connected by performing overlap extension PCR method. Primer 11 (SEQ ID NO: 27) and primer 16 (SEQ ID NO: 32) were used to amplify one of the fragments. Then, primer 15 (SEQ ID NO: 31) and primer 14' (SEQ ID NO: 78) were used to amplify the other fragment. The PCR products were mixed, heat denatured, and amplified by performing PCR. Primer 11 (SEQ ID NO: 27) and primer 14' (SEQ ID NO: 78) were used for this PCR reaction. The obtained fragment was treated with Nhe I and Xho I. The treated fragment was ligated into a plasmid pretreated with Nhe I and Xho I to obtain an expression plasmid (hereinafter, referred to as "plasmid (Kir3.1 (F137S)").

(Construction of Wild Type G Protein ($G_{\alpha olf}$) Expression Plasmid)

RNA was isolated from mouse olfactory bulb and was then reverse transcribed by using reverse transcriptase to obtain total cDNA in mouse olfactory cells. The obtained cDNA was used as template, and the $G_{\alpha olf}$ gene was amplified by PCR. Primer 17 (SEQ ID NO: 33) and primer 18 (SEQ ID NO: 34) were used. The obtained gene fragment was ligated into a plasmid, and thereby the $G_{\alpha olf}$ gene (GenBank Accession Number: AY179168.1) was cloned. The obtained $G_{\alpha olf}$ fragment was further amplified by PCR. Primer 19 (SEQ ID NO: 35) and primer 20 (SEQ ID NO: 36) were used. As a result, restriction enzyme sites were added to the ends of the amplified fragment. The amplified fragment having the restriction enzyme sites was ligated into an expression plasmid to obtain a wild type G protein ($G_{\alpha olf}$) expression plasmid (hereinafter, referred to as "plasmid ($G_{\alpha olf}$)").

(Construction of G Protein ($G_{\alpha i}$ (C351G)) Expression Plasmid)

Figure 23:
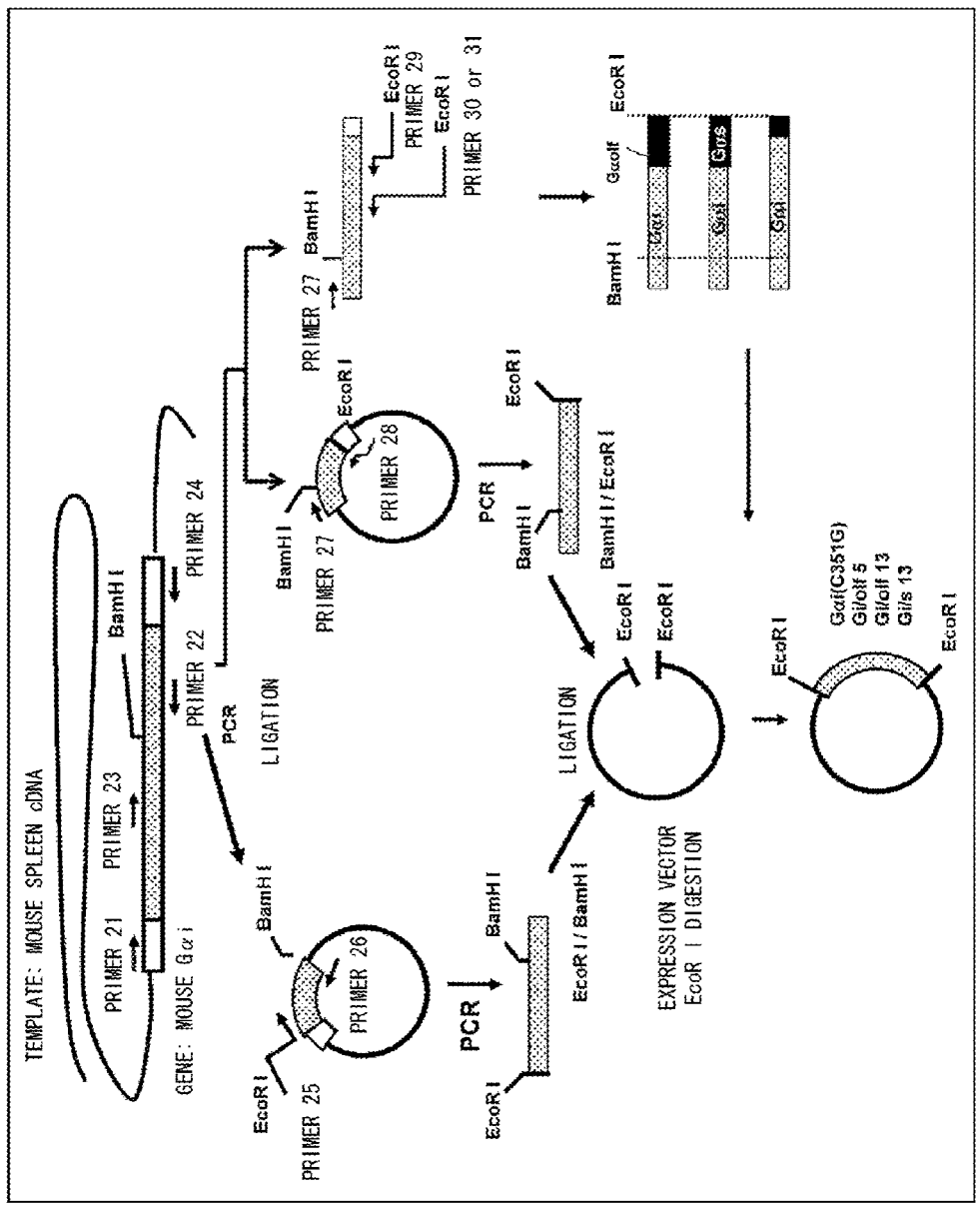
FIG. 23 illustrates a concept of a method for constructing a chimeric G protein expression plasmid.

FIG. 23 shows a procedure to construct $G_{\alpha i}$ (C351G) protein expression plasmid in which cysteine at position 351 of $G_{\alpha i}$ was substituted with glycine. It has been revealed that $G_{\alpha i}$ (C351G) has the same functions as wild type $G_{\alpha i}$, except for having resistance to pertussis toxin which is a selective inhibitor of $G_{\alpha i}$. A procedure in which the $G_{\alpha i}$ (mouse $G_{i}$: NM-010305) gene was amplified is shown below. Mouse spleen-derived cDNA (mouse spleen cDNA) was amplified as two separate fragments by performing PCRs. Primers used to amplify one of the fragments were primer 21 (SEQ ID NO: 37) and primer 22 (SEQ ID NO: 38). Primers used to amplify the other fragment were primer 23 (SEQ ID NO: 39) and primer 24 (SEQ ID NO: 40). Each of the obtained two fragments was ligated into a plasmid. PCRs were performed by using these two plasmids as templates. Primers used to amplify one of the plasmids were primer 25 (SEQ ID NO: 41) and primer 26 (SEQ ID NO: 42). Primers used to amplify the other plasmid were primer 27 (SEQ ID NO: 43) and primer 28 (SEQ ID NO: 44). As a result, restriction enzyme sites were added to the ends of the amplified fragments. One of the two obtained fragments was treated with EcoRI and BamHI. The other one was treated with BamHI and EcoRI. The treated fragments were ligated into an expression plasmid pretreated with EcoRI to obtain a wild type G protein ($G_{\alpha i}$) expression plasmid (hereinafter, referred to as "plasmid ($G_{\alpha i}$)"). Table 3 shows sequences of the used primers.

TABLE 3

| | Sequence | SEQ ID NO: |
|---|---|---|
| Primer 14' | gcctcgagctatgtgaaacggtcagag | 78 |
| Primer 15 | ctctgccttcctcttctccatcgagaccga | 31 |
| Primer 16 | ggtctcgatggagaagaggaaggcagagg | 32 |
| Primer 17 | atggggtgtttgggcaacagcagcaagac | 33 |
| Primer 18 | ggaggaggaggagggtaggtttagg | 34 |
| Primer 19 | aatgaattcgccaccatgggtgtttgggcaacag | 35 |
| Primer 20 | aatgtcgactcacaagagttcgtactgcttgag | 36 |
| Primer 21 | cggcagcgtgcggactagcagacct | 37 |
| Primer 22 | gaacagcttcatgctctcgtgcatacgg | 38 |
| Primer 23 | gctgaacgattcggcagcgtactatctg | 39 |
| Primer 24 | ggtcagaactctggtcaggtccaggatg | 40 |
| Primer 25 | gcgctcgagccaccatgggctgcacattgagcgct | 41 |
| Primer 26 | aagtggatccactgctttgaagg | 42 |
| Primer 27 | agtggatccacttatccgctc | 43 |
| Primer 28 | cgcgaattcttagaagagaccaatgtcttttaggttattctttatgat gacgtctgttacagcatcgaacacgaac | 44 |

(Construction of Chimeric G Protein ($G_{i/olf5}$) Expression Plasmid)

A chimeric G protein ($G_{i/olf5}$) expression plasmid (hereinafter, referred to as "plasmid ($G_{i/olf5}$)") was constructed in accordance with a procedure same as that used for constructing the plasmid ($G_{\alpha i}$), except for using primer 29 (SEQ ID NO: 45) instead of primer 28. The construction procedure is shown in FIG. 23.

(Construction of Chimeric G Protein ($G_{i/s13}$) Expression Plasmid)

A chimeric G protein ($G_{i/s13}$) expression plasmid (hereinafter, referred to as "plasmid ($G_{i/s13}$)") was constructed in accordance with a procedure same as that used for constructing the plasmid ($G_{\alpha i}$), except for using primer 30 (SEQ ID NO: 46) instead of primer 28. The construction procedure is shown in FIG. 23.

(Construction of Chimeric G Protein ($G_{i/olf13}$) Expression Plasmid)

A chimeric G protein ($G_{i/olf13}$) expression plasmid (hereinafter, referred to as "plasmid ($G_{i/olf13}$)") was constructed in accordance with a procedure same as that used for constructing the plasmid ($G_{\alpha i}$), except for using primer 31 (SEQ ID NO: 47) instead of primer 28. The construction procedure is shown in FIG. 23. Table 4 shows sequences of the used primers.

TABLE 4

| | Sequence | SEQ ID NO: |
|---|---|---|
| Primer 29 | cgcgaattcttagagcagctcgtattgttttaggttatt ctttatgatgacgtctgttacagcatcgaacacgaa c | 45 |
| Primer 30 | cgcgaattcttagagcagctcgtattggcggagatg catgcgctggatgatgtctgttacagcatcgaacac gaac | 46 |
| Primer 31 | cgcgaattcttagagcagctcgtattgcttgagatgc atgcgctggatgatgtctgttacagcatcgaacacg aac | 47 |

(Construction of Chimeric G Protein ($G_{i/olf28}$) Expression Plasmid)

A chimeric G protein ($G_{i/olf28}$) expression plasmid (hereinafter, referred to as "plasmid ($G_{i/olf28}$)") was constructed through overlap extension PCR by using the plasmid ($G_{i/olf13}$) as template I and the plasmid ($G_{\alpha olf}$) as template II. As shown in FIG. 24, A-PRIMER and B-PRIMER were used as primers for the PCR using template I. By using A-PRIMER and B-PRIMER, a base sequence coding for amino acids of predetermined regions included in $G_{\alpha i}$ can be selectively amplified. One part of the obtained fragment was added to the complementary sequence of B-PRIMER to form a sticky end. C-PRIMER and D-PRIMER were used as primers for the PCR using template II. By using C-PRIMER and D-PRIMER, a base sequence coding for amino acids of predetermined regions included in $G_{\alpha olf}$ can be selectively amplified. One part of the obtained fragment was added to the complementary sequence of C-PRIMER to form a sticky end. More particularly, primer 32 (SEQ ID NO: 48) was used as A-PRIMER, and primer 33 (SEQ ID NO: 49) was used as B-PRIMER. Primer 34 (SEQ ID NO: 50) was used as C-PRIMER, and primer 35 (SEQ ID NO: 51) was used as D-PRIMER. Both PCR products were connected to each other via the sticky ends by overlap extension PCR. Here, A-PRIMER and D-PRIMER were used as primers. The obtained fragment was treated with EcoRI and SalI, and the treated fragment was ligated into an expression plasmid pretreated with EcoRI and SalI to obtain plasmid ($G_{i/olf28}$). Escherichia coli transformed with the plasmid ($G_{i/olf28}$) was cultured. The plasmid ($G_{i/olf28}$) purified from Escherichia coli was used for transfecting cells.

(Construction of Chimeric G Protein ($G_{i/olf45}$) Expression Plasmid)

A chimeric G protein ($G_{i/olf48}$) expression plasmid (hereinafter, referred to as "plasmid ($G_{i/olf48}$)") was constructed in accordance with a procedure same as that used for constructing the plasmid ($G_{i/olf28}$), except for using primers shown in Table 5.

(Construction of Chimeric G Protein ($G_{i/olf94}$) Expression Plasmid)

A chimeric G protein ($G_{i/olf94}$) expression plasmid (hereinafter, referred to as "plasmid ($G_{i/olf94}$)") was constructed in accordance with a procedure same as that used for constructing the plasmid ($G_{i/olf28}$), except for using primers shown in Table 5.

(Construction of Chimeric G Protein ($G_{i/olf113}$) Expression Plasmid)

A chimeric G protein ($G_{i/olf113}$) expression plasmid (hereinafter, referred to as "plasmid ($G_{i/olf113}$)") was constructed in accordance with a procedure same as that used for constructing the plasmid ($G_{i/olf28}$), except for using primers shown in Table 5.

(Construction of Chimeric G Protein ($G_{i/olf156}$) Expression Plasmid)

A chimeric G protein ($G_{i/olf156}$) expression plasmid (hereinafter, referred to as "plasmid ($G_{i/olf156}$)") was constructed in accordance with a procedure same as that used for constructing the plasmid ($G_{i/olf28}$), except for using primers shown in Table 5.

(Construction of Chimeric G Protein ($G_{i/olf195}$) Expression Plasmid)

A chimeric G protein ($G_{i/olf195}$) expression plasmid (hereinafter, referred to as "plasmid ($G_{i/olf195}$)") was constructed in accordance with a procedure same as that used for constructing the plasmid ($G_{i/olf28}$), except for using primers shown in Table 5.

TABLE 5

| | | Sequence (5'→3') | SEQ ID NO: |
|---|---|---|---|
| $G_{i/olf}$ 38 | A-PRIMER Primer 32 | cctgaattctgccaccatgggctgcacattgagcg | 48 |
| | B-PRIMER Primer 33 | cccgtggctgtattgaggtcttcaaactgacactg | 49 |
| | C-PRIMER Primer 34 | agtttgaagacctcaatacagccacgggtgatg | 50 |
| | D-PRIMER Primer 35 | accgtcgacgtcacaagagttcgtactgcttgag | 51 |
| $G_{i/olf}$ 45 | A-PRIMER Primer 42 | cctgaattctgccaccatgggctgcacattgagcg | 58 |
| | B-PRIMER Primer 43 | tgtgtccacggcgcacgtgaagtggg | 59 |

TABLE 5-continued

| | | Sequence (5'→3') | SEQ ID NO: |
|---|---|---|---|
| | C-PRIMER Primer 44 | acgtgcgccgtggacacagagaacatccg | 60 |
| | D-PRIMER Primer 45 | accgtcgacgtcacaagagttcgtactgcttgag | 61 |
| $G_{i/olf\,94}$ | A-PRIMER Primer 46 | cctgaattctgccaccatgggctgcacattgagcg | 62 |
| | B-PRIMER Primer 47 | tgccaagactttttcttcgaagaggtccttcttg | 63 |
| | C-PRIMER Primer 48 | gaagaaaaagtcttggcagggaagtcaaaaatcg | 64 |
| | D-PRIMER Primer 49 | accgtcgacgtcacaagagttcgtactgcttgag | 65 |
| $G_{i/olf\,113}$ | A-PRIMER Primer 50 | cctgaattctgccaccatgggctgcacattgagcg | 66 |
| | B-PRIMER Primer 51 | atggttcgcaaccacttgttgttacagatgctatcg | 67 |
| | C-PRIMER Primer 52 | acaacaagtggttgcgaaccatttctatcatcc | 68 |
| | D-PRIMER Primer 53 | accgtcgacgtcacaagagttcgtactgcttgag | 69 |
| $G_{i/olf\,156}$ | A-PRIMER Primer 54 | cctgaattctgccaccatgggctgcacattgagcg | 70 |
| | B-PRIMER Primer 55 | acatcattaaagcagtggatccacttcttccg | 71 |
| | C-PRIMER Primer 56 | actgctttaatgatgtcactgcgatcatttacg | 72 |
| | D-PRIMER Primer 57 | accgtcgacgtcacaagagttcgtactgcttgag | 73 |
| $G_{i/olf\,195}$ | A-PRIMER Primer 58 | cctgaattctgccaccatgggctgcacattgagcg | 74 |
| | B-PRIMER Primer 59 | actctgcatctgaggacatcctgctgagttg | 75 |
| | C-PRIMER Primer 60 | gtcctcagatgcagagtgctgacatcagg | 76 |
| | D-PRIMER Primer 61 | accgtcgacgtcacaagagttcgtactgcttgag | 77 |

Table 6 shows regions of amino acid sequences amplified by respective primers.

TABLE 6

| $G_{\alpha i}$ | | $G_{\alpha olf}$ | | Chimeric G |
|---|---|---|---|---|
| Primer | Region | Primer | Region | protein |
| | 1-354 | | | $G_{\alpha i}$ |
| Primer 32/ Primer 33 | 1-326 | Primer 34/ Primer 35 | 354-381 | $G_{i/olf28}$ |
| Primer 42/ Primer 43 | 1-311 | Primer 44/ Primer 45 | 335-381 | $G_{i/olf45}$ |
| Primer 46/ Primer 47 | 1-277 | Primer 48/ Primer 49 | 288-381 | $G_{i/olf94}$ |
| Primer 54/ Primer 55 | 1-215 | Primer 56/ Primer 57 | 226-381 | $G_{i/olf156}$ |
| Primer 58/ Primer 59 | 1-176 | Primer 60/ Primer 61 | 187-381 | $G_{i/olf195}$ |
| Primer 50/ Primer 51 | 1-258 | Primer 52/ Primer 53 | 269-381 | $G_{i/olf113}$ |
| | | | 1-381 | $G_{olf}$ |

(Construction of Chimeric G Protein ($G_{i/olf\alpha 3-\beta 5}$) Expression Plasmid)

Figure 25:
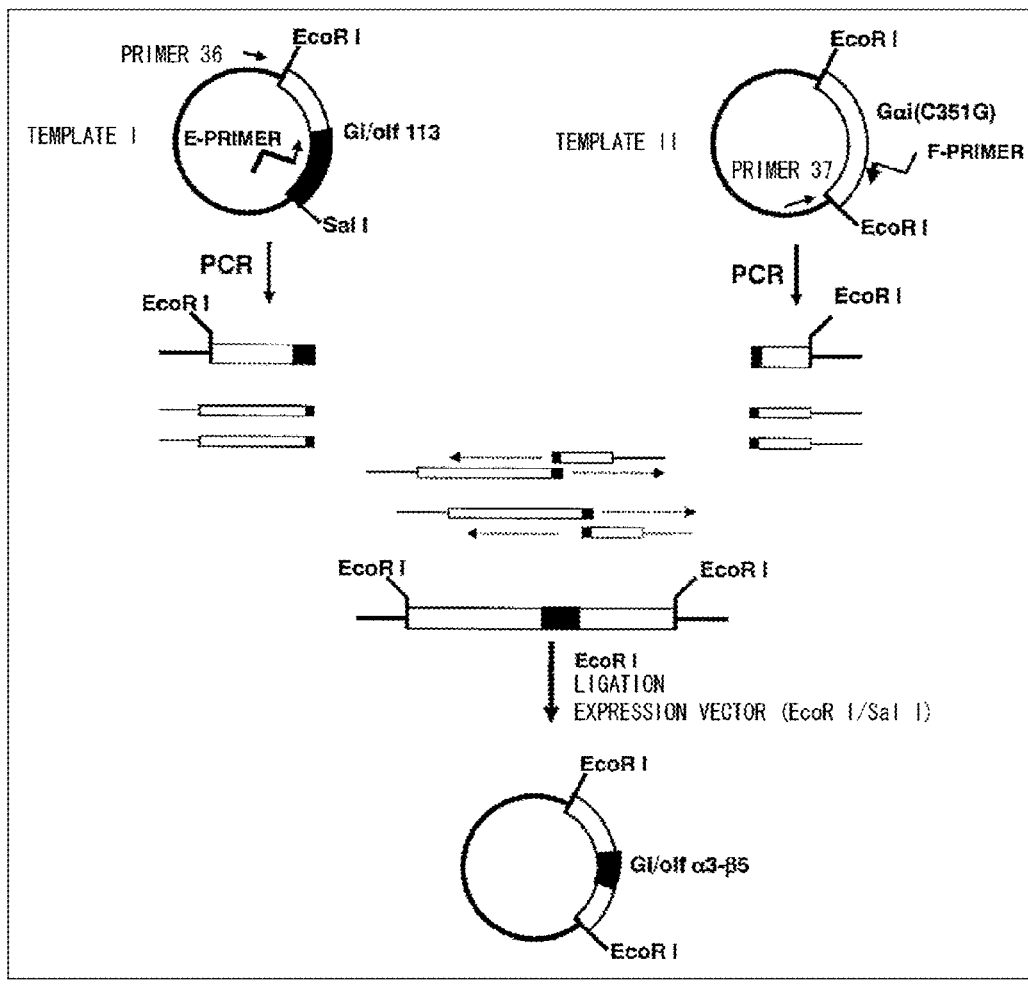
FIG. 25 illustrates a concept of a method for constructing a chimeric G protein expression plasmid.

A chimeric G protein ($G_{i/olf\alpha 3-\beta 5}$) expression plasmid (hereinafter, referred to as "plasmid ($G_{i/olf\alpha 3-\beta 5}$)") was constructed through overlap extension PCR by using the plasmid ($G_{i/olf13}$) as template I and the plasmid ($G_{\alpha i}$) as template II. As shown in FIG. 25, primer 36 (SEQ ID NO: 52) and E-PRIMER were used as primers for the PCR using template I. More particularly, primer 37 (SEQ ID NO: 53) was used as E-PRIMER. One part of the obtained fragment was added to the complementary sequence of E-PRIMER to form a sticky end. Primer 39 (SEQ ID NO: 55) and F-PRIMER were used as primers for the PCR using template II. More particularly, primer 38 (SEQ ID NO: 54) was used as F-PRIMER. One part of the obtained fragment was added to the complementary sequence of F-PRIMER to form a sticky end. Both PCR products were connected to each other via sticky ends by overlap extension PCR using primer 36 and primer 39. The obtained fragment was treated with EcoRI, and ligated into an expression plasmid pretreated with EcoRI to obtain the plasmid ($G_{i/olf\alpha 3-\beta 5}$). *Escherichia coli* transformed with the plasmid ($G_{i/olf\alpha 3-\beta 5}$) was cultured. The plasmid ($G_{i/olf\alpha 3-\beta 5}$) purified from *Escherichia coli* was used for transfecting cells.

(Construction of Chimeric G Protein ($G_{i/olf\alpha 3-\beta 5,C}$) Expression Plasmid)

A chimeric G protein ($G_{i/olf\alpha 3-\beta 5,C}$) expression plasmid (hereinafter, referred to as "plasmid ($G_{i/olf\alpha 3-\beta 5,C}$)") was constructed in accordance with a procedure same as that used for constructing the plasmid ($G_{olf\alpha 3-\beta 5}$), except for using templates and restriction enzymes described in Table 7.

(Construction of Chimeric G Protein ($G_{i/olf\alpha 4-\beta 6}$) Expression Plasmid)

A chimeric G protein ($G_{i/olf\alpha 4-\beta 6}$) expression plasmid (hereinafter, referred to as "plasmid ($G_{i/olf\alpha 4-\beta 6}$)") was constructed in accordance with a procedure same as that used for constructing the plasmid ($G_{olf\alpha 3-\beta 5}$), except for using templates, E-PRIMER, F-PRIMER, and a restriction enzyme described in Table 7.

(Construction of Chimeric G Protein ($G_{i/olf\alpha 4-\beta 6,C}$) Expression Plasmid)

A chimeric G protein ($G_{i/olf\alpha 4-\beta 6,C}$) expression plasmid (hereinafter, referred to as "plasmid ($G_{i/olf\alpha 4-\beta 6,C}$)") was constructed in accordance with a procedure same as that used for constructing the plasmid ($G_{olf\alpha 3-\beta 5}$), except for using templates, E-PRIMER, F-PRIMER, and restriction enzymes described in Table 7.

(Construction of Chimeric G Protein ($G_{i/olf\alpha 3-\beta 5,\alpha 4-\beta 6}$) Expression Plasmid)

A chimeric G protein ($G_{i/olf\alpha 3-\beta 5,\alpha 4-\beta 6}$) expression plasmid (hereinafter, referred to as "plasmid ($G_{i/olf\alpha 3-\beta 5,\alpha 4-\beta 6}$)") was constructed in accordance with a procedure same as that used for constructing the plasmid ($G_{olf\alpha 3-\beta 5}$), except for using templates, E-PRIMER, F-PRIMER, and a restriction enzyme described in Table 7.

(Construction of Chimeric G Protein ($G_{i/olf\alpha 3-\beta 5,\alpha 4-\beta 6,C}$) Expression Plasmid)

A chimeric G protein ($G_{i/olf\alpha 3-\beta 5,\alpha 4-\beta 6,C}$) expression plasmid (hereinafter, referred to as "plasmid ($G_i/olf\alpha 3-\beta 5,\alpha 4-\beta 6,C$)") was constructed in accordance with a procedure same as that used for constructing the plasmid ($G_{olf\alpha 3-\beta 5}$), except for using templates, E-PRIMER, F-PRIMER, and restriction enzymes described in Table 7.

TABLE 7

| Constructed Expression Plasmid | Template I | Template II | E-PRIMER | F-PRIMER | Restriction Enzyme |
|---|---|---|---|---|---|
| Plasmid ($G_{i/olf\alpha 3-\beta 5}$) | Plasmid ($G_{i/olf13}$)  | plasmid ($G_{\alpha i}$)  | Primer 37 | Primer 38 | EcoRI |
| Plasmid ($G_{i/olf\alpha 3-\beta 5,C}$) | Plasmid ($G_{i/olf13}$)  | plasmid ($_{Gi/olf13}$)  | Primer 37 | Primer 38 | EcoRI/SalI |
| Plasmid ($G_{i/olf\alpha 4-\beta 6}$) | plasmid ($G_{i/olf45}$)  | plasmid ($G_{\alpha i}$)  | Primer 40 | Primer 41 | EcoRI |
| Plasmid ($G_{i/olf\alpha 4-\beta 6,C}$) | plasmid ($G_{i/olf45}$)  | plasmid ($G_{i/olf13}$)  | Primer 40 | Primer 41 | EcoRI/SalI |
| Plasmid ($G_{i/olf\alpha 3-\beta 5,\alpha 4-\beta 6}$) | plasmid ($G_{i/olf\alpha 3-\beta 5}$)  | plasmid ($G_{i/olf\alpha 4-\beta 6}$)  | Primer 37 | Primer 38 | EcoRI |
| Plasmid ($G_{i/olf\alpha 3-\beta 5,\alpha 4-\beta 6,C}$) | plasmid ($G_{i/olf\alpha 3-\beta 5}$)  | plasmid ($_{Gi/olf\alpha 4-\beta 6,C}$)  | Primer 37 | Primer 38 | EcoRI/SalI |

[Measurement of Electrophysiological Activities]

A cell was obtained that expressed a chimeric G protein, a potassium ion channel, and a chemical substance receptor (hereinafter, the cell is referred to as "chimeric G protein expressing cell"). An electrophysiological activity of the chimeric G protein expressing cell was measured by using patch-clamp method. The chimeric G protein expressing cell was prepared in accordance with the following procedure. First, a chimeric G protein expression plasmid, a potassium ion channel expression plasmid, and a chemical substance receptor expression plasmid were prepared. Next, the three expression plasmids were transfected into HEK293T cells, and were then expressed inside the cells.

Example 1

A chimeric G protein comprising $G_{i/olf13}$ as a chimeric $G_\alpha$ subunit was employed. The mutated potassium ion channel Kir3.1 (F137S) was employed as a potassium ion channel. The β1 adrenergic receptor was employed as a chemical substance receptor.

(Preparation of Chimeric G Protein Expressing Cells)

The plasmid (βAR), the plasmid Kir3.1 (F137S), and the plasmid ($G_{i/olf13}$) were expressed in HEK293T cells. The procedure for the expression is shown below. Approximately 80% confluent cultured HEK293T cells were collected, and plated on a new culture petri dish. The passage number of the used cells was not more than ten generations. DMEM (supplemented with 10% FBS (fetal bovine serum) and streptomycin) was used. After culturing the cells for 24 hours, the cells were transfected with the plasmids by using a transfection reagent. The cells were cultured for 48 hours after being transfected with the plasmids, and thereby chimeric G protein expressing cells were prepared.

(Measurement of Current Change Levels)

Membrane current of the chimeric G protein expressing cell was measured by using a patch-clamp technique. Measurements were conducted with and without supplying isoproterenol (hereinafter, referred to as "ISO") which was a β1 adrenergic receptor agonist. Procedure for the measurements is shown below.

(Samples for Measurements)

The chimeric G protein expressing cells were plated on coverslips (3 mm×10 mm; Matsunami Glass Ind., Ltd.,) treated with PLL (poly-L-lysine) and kept still for four hours to obtain samples for the measurements.

(Glass Electrodes)

Procedure for preparing glass electrodes used for the measurements is described below. By using a glass electrode manufacturing device ("Laser Puller P-2000" manufactured by Sutter Instrument Co.,), glass pipettes having a 1 μm diameter at one end were prepared from glass tubes (outer diameter 1.5 mm, internal diameter 0.86 mm, length 100 mm). Silver/silver chloride (Ag/AgCl) electrodes were inserted in the glass pipettes. The glass pipettes were filled with buffer A. The composition of the buffer A was similar to the composition of an intracellular fluid. The composition of the buffer A is shown in Table 8

(Measurements)

Measurement operations were conducted under a microscope ("1X71" manufactured by Olympus, Inc.). A liquid circulation chamber was mounted on the silver/silver chloride (Ag/AgCl) electrode. A sample for measurement was placed in the liquid circulation chamber filled with Tyroad's buffer. At a state where a single cell was in contact with the tip of a glass electrode, negative pressure was applied in the glass electrode. The portion of a cell membrane in contact with the tip of the glass electrode was torn to form an equivalent circuit (Whole-cell mode). The electric potential difference between inside and outside a cell was kept at 0 mV by using a patch clamp amplifier ("EPC10" manufactured by HEKA Instrument Inc.). Under this mode, the Tyroad's buffer in the liquid circulation chamber was substituted with a GIRK buffer. Pulse potentials (electric potential: −50 mV; duration time: 100 mS) were applied every 10 seconds, and membrane currents obtained upon the application were measured. Table 8 shows the compositions of the Tyroad's buffer and the GIRK buffer.

Next, membrane currents obtained when isoproterenol (hereinafter, abbreviated as "ISO") which is a β1 adrenergic receptor agonist was brought into contact with the cell were measured in accordance with the following procedure. The GIRK buffer in the liquid circulation chamber was substituted with a sample solution. Under a condition in which the electric potential difference between inside and outside a cell was kept at 0 mV, pulse potentials (electric potential: −50 mV; duration time: 100 mS) were applied every 10 seconds, and membrane currents obtained upon the application were measured. The composition of the sample solution is shown in Table 8.

TABLE 8

|  | Tyroad's buffer | GIRK buffer | Buffer A | Sample solution |
|---|---|---|---|---|
| Sodium Chloride (mM) | 140 | — | — | — |
| Potassium Chloride (mM) | 5 | 140 | 107 | 140 |
| Calcium Chloride (mM) | 2 | 2.6 | 1 | 2.6 |
| Magnesium Chloride (mM) | 1 | 1.2 | 1.2 | 1.2 |
| Glucose (mM) | 10 | 10 | — | 10 |
| HEPES (mM) | 10 | 5 | 5 | 5 |
| EGTA (mM) |  |  | 10 | — |
| ATP (mM) | — | — | 2 | — |
| GTP (mM) | — | — | 0.3 | — |
| ISO (nM) | — | — | — | 30 |
| pH | 7.4 | 7.4 | 7.2 | 7.2 |
| Osmotic Pressure (mOsm/kg) | 290-300 | 290-300 | 290-300 | 290-300 |

Examples 2 to 6

Chimeric G protein expressing cells were prepared and membrane currents were measured similarly to Example 1, except for employing chimeric G proteins comprising respective $G_\alpha$ subunits described in Table 9 instead of the chimeric G protein comprising $G_{i/olf13}$.

TABLE 9

|  | $G_\alpha$ subunit | SEQ ID NO: |
|---|---|---|
| Example 1 | $G_{i/olf13}$ | 4 |
| Example 2 | $G_{i/olf28}$ | 5 |
| Example 3 | $G_{i/olf94}$ | 7 |
| Example 4 | $G_{i/olf113}$ | 8 |
| Example 5 | $G_{i/olf\alpha3-\beta5,C}$ | 12 |
| Example 6 | $G_{i/olf\alpha4-\beta6,C}$ | 15 |

Comparative Examples 1 to 10

Chimeric G protein expressing cells were prepared and membrane currents were measured similarly to Example 1, except for employing chimeric G proteins comprising respective $G_\alpha$ subunits described in Table 10 instead of the chimeric G protein comprising $G_{i/olf13}$.

TABLE 10

|  | $G_\alpha$ subunit | SEQ ID NO: |
|---|---|---|
| Comparative Example 1 | $G_{\alpha i}$ (C351G) | 1 |
| Comparative Example 2 | $G_{\alpha olf}$ | 2 |
| Comparative Example 3 | $G_{i/olf5}$ | 3 |
| Comparative Example 4 | $G_{i/olf45}$ | 6 |
| Comparative Example 5 | $G_{i/olf156}$ | 9 |
| Comparative Example 6 | $G_{i/olf195}$ | 10 |
| Comparative Example 7 | $G_{i/olf\alpha3-\beta5}$ | 11 |
| Comparative Example 8 | $G_{i/olf\alpha4-\beta6}$ | 13 |
| Comparative Example 9 | $G_{i/olf\alpha3-\beta5,\alpha4-\beta6}$ | 14 |
| Comparative Example 10 | $G_{i/olf\alpha3-\beta5,\alpha4-\beta6,C}$ | 16 |

Comparative Example 11

When the chimeric G protein expressing cells was prepared, the cells were prepared similarly to Example 1, except for transfecting the cells with the plasmid ($G_{i/olf13}$). Then, membrane currents of the prepared cells were measured.

Figure 4:
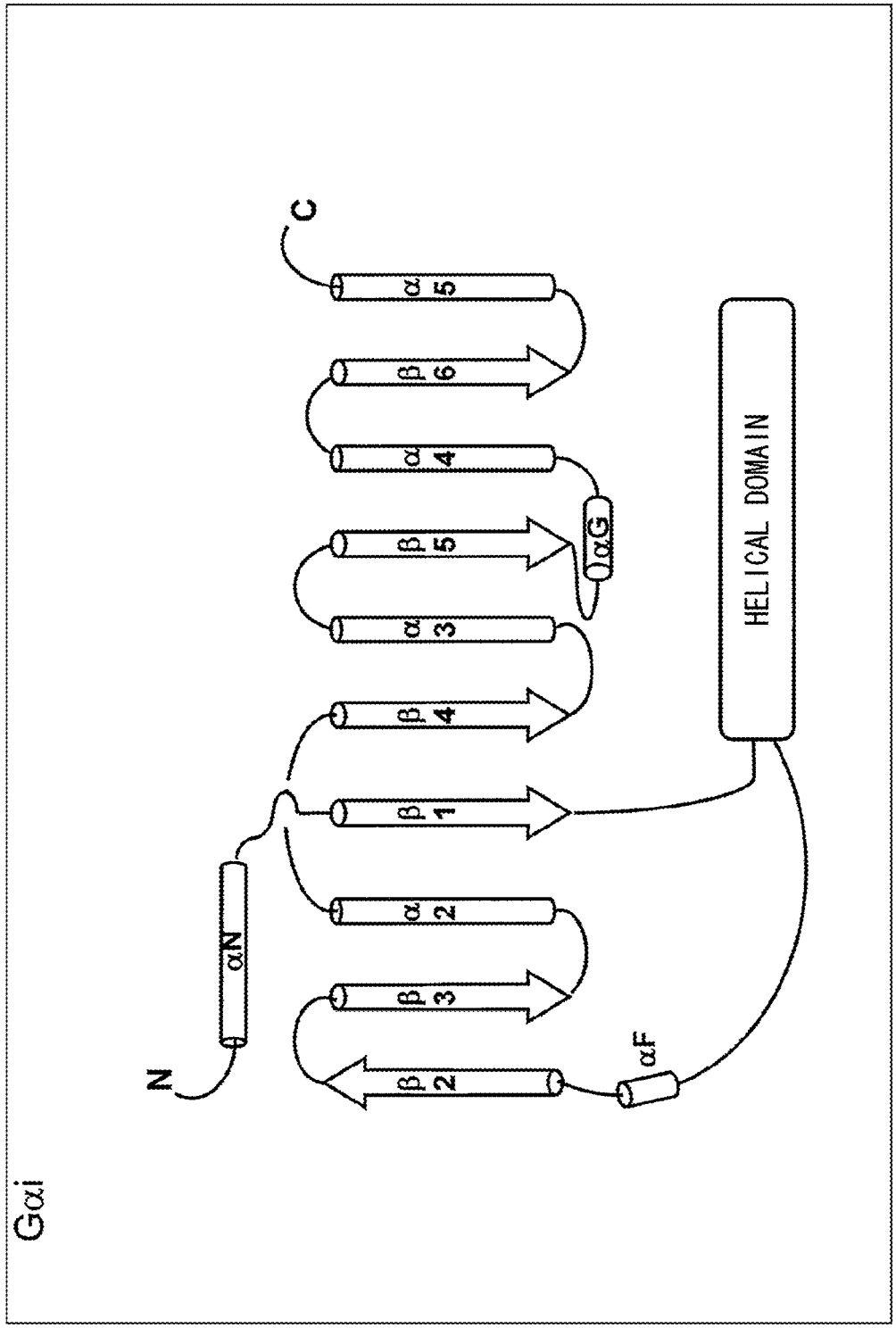
FIG. 4 is a schematic diagram showing a secondary structure of $G_{\alpha i}$.

The amino acid sequence of $G_\alpha$ subunit ($G_{\alpha i}$ (C351G)) used in Comparative Example 1 is shown below. FIG. 4 schematically shows a secondary structure of ($G_{\alpha i}$ (C351G)).

(SEQ ID NO: 1)
MGCTLSAEDKAAVERSKMIDRNLREDGEKAAREVKLLLLGAGESGKSTIV

KQMKIIHEAGYSEEECKQYKAVVYSNTIQSIIAIIRAMGRLKIDFGDSAR

ADDARQLFVLAGAAEEGFMTAELAGVIKRLWKDSGVQACFNRSREYQLND

SAAYYLNDLDRIAQPNYIPTQQDVLRTRVKTTGIVETHFTFKDLHFKMFD

VGGQRSERKKWIHCFEGVTAIIFCVALSDYDLVLAEDEEMNRMHESMKLF

DSICNNKWFTDTSIILFLNKKDLFEEKIKKSPLTICYPEYAGSNTYEEAA

AYIQCQFEDLNKRKDTKEIYTHFTCATDTKNVQFVFDAVTDVIIKNNLKD

IGLF

Figure 5:
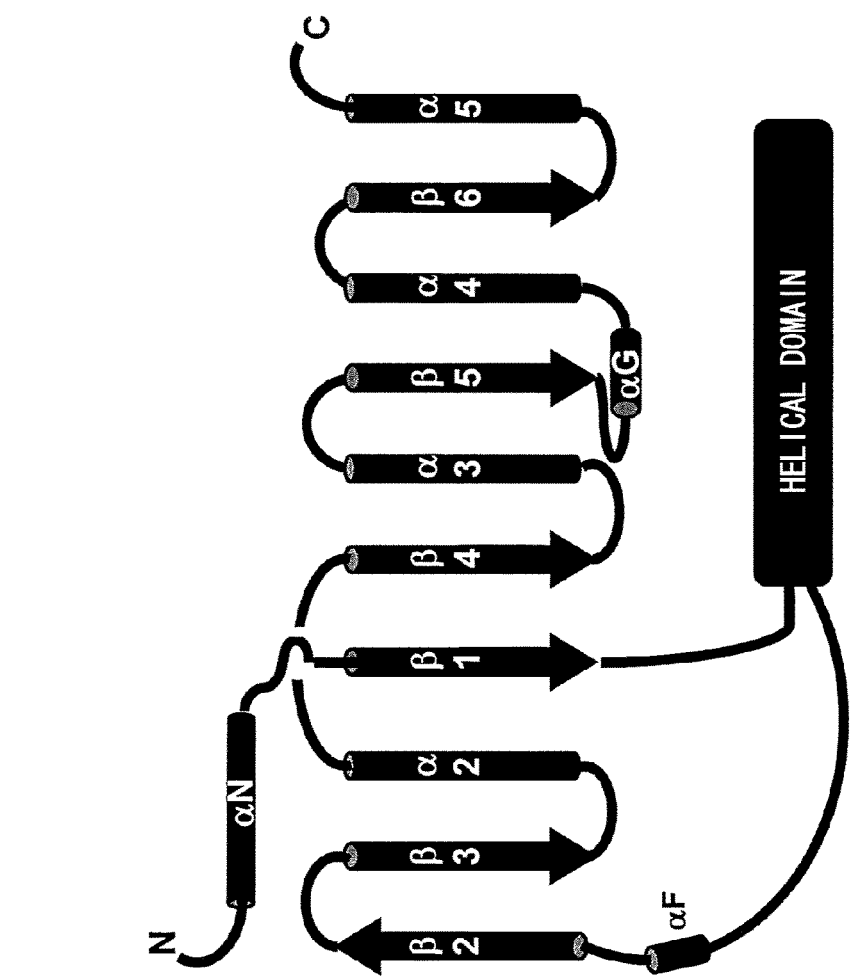
FIG. 5 schematically shows a secondary structure of $G_{\alpha olf}$.

The amino acid sequence of $G_\alpha$ subunit ($G_{\alpha olf}$) used in Comparative Example 2 is shown below. FIG. 5 schematically shows a secondary structure of ($G_{\alpha olf}$).

(SEQ ID NO: 2)
MGCLGNSSKTAEDQGVDEKERREANKKIEKQLQKERLAYKATHRLLLLGA

GESGKSTIVKQMRILHVNGFNPEEKKQKILDIRKNVKDAIVTIVSAMSTI

```
IPPVPLANPENQFRSDYIKSIAPITDFEYSQEFFDHVKKLWDDEGVKACF

ERSNEYQLIDCAQYFLERIDSVSLVDYTPTDQDLLRCRVLTSGIFETRFQ

VDKVNFHMFDVGGQRDERRKWIQCFNDVTAIIYVAACSSYNMVIREDNNT

NRLRESLDLFESIWNNRWLRTISIILFLNKQDMLAEKVLAGKSKIEDYFP

EYANYTVPEDATPDAGEDPKVTRAKFFIRDLFLRISTATGDGKHYCYPHF

TCAVDTENIRRVFNDCRDIIQRMHLKQYELL
```

Figure 6:
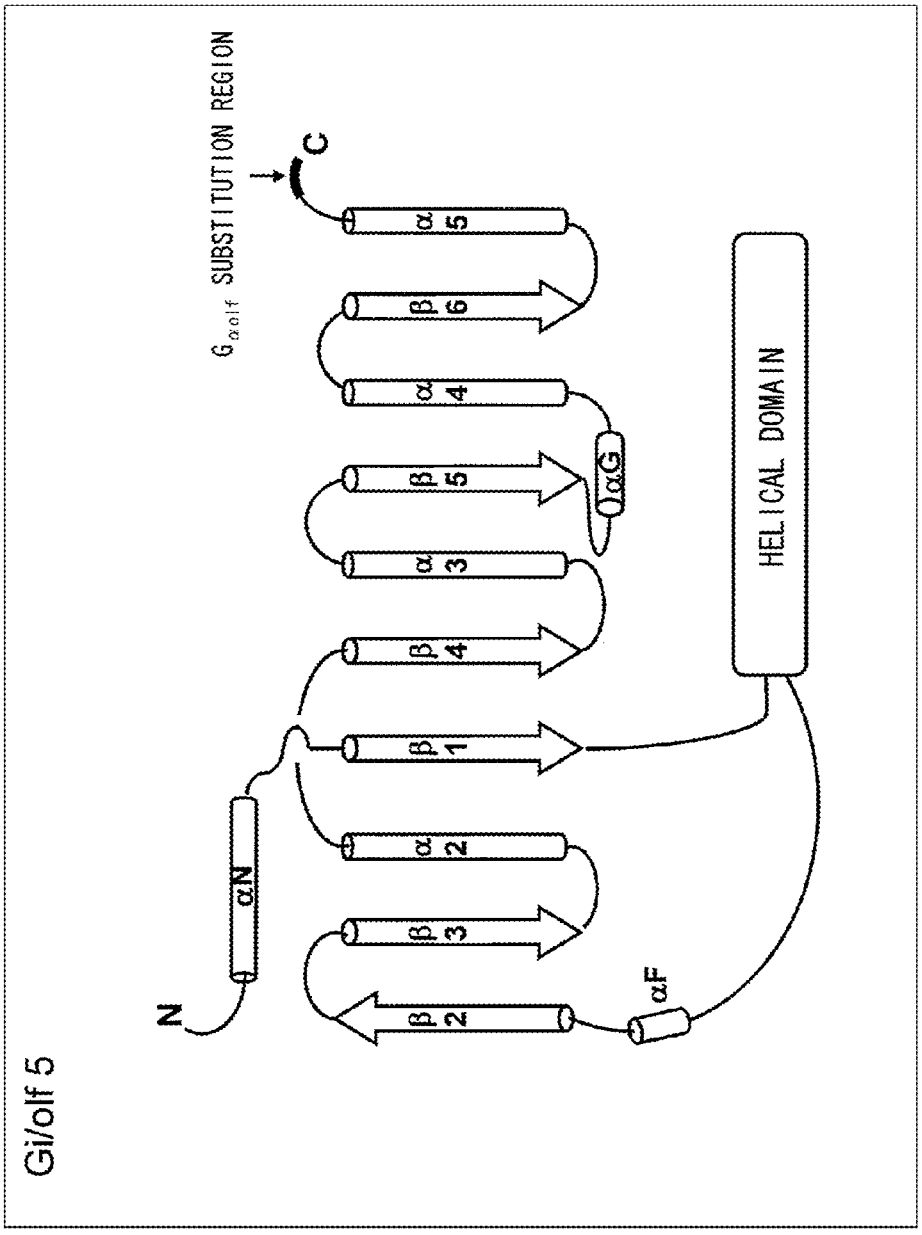
FIG. 6 schematically shows a secondary structure of $G_{i/olf5}$.

The amino acid sequence of a chimeric $G_\alpha$ subunit ($G_{i/olf5}$) used in Comparative Example 3 is shown below. $G_{i/olf5}$ is a chimeric $G_\alpha$ subunit obtained by substituting five amino acids on the C-terminal side of $G_{\alpha i}$ protein with corresponding amino acids of $G_{\alpha olf}$. FIG. 6 schematically shows a secondary structure of $G_{i/olf5}$.

```
                                        (SEQ ID NO: 3)
MGCTLSAEDKAAVERSKMIDRNLREDGEKAAREVKLLLLGAGESGKSTIV

KQMKIIHEAGYSEEECKQYKAVVYSNTIQSIIAIIRAMGRLKIDFGDSAR

ADDARQLFVLAGAAEEGFMTAELAGVIKRLWKDSGVQACFNRSREYQLND

SAAYYLNDLDRIAQPNYIPTQQDVLRTRVKTTGIVETHFTFKDLHFKMFD

VGGQRSERKKWIHCFEGVTAIIFCVALSDYDLVLAEDEEMNRMHESMKLF

DSICNNKWFTDTSIILFLNKKDLFEEKIKKSPLTICYPEYAGSNTYEEAA

AYIQCQFEDLNKRKDTKEIYTHFTCATDTKNVQFVFDAVTDVIIKNNLKQ

YELL
```

Figure 9:
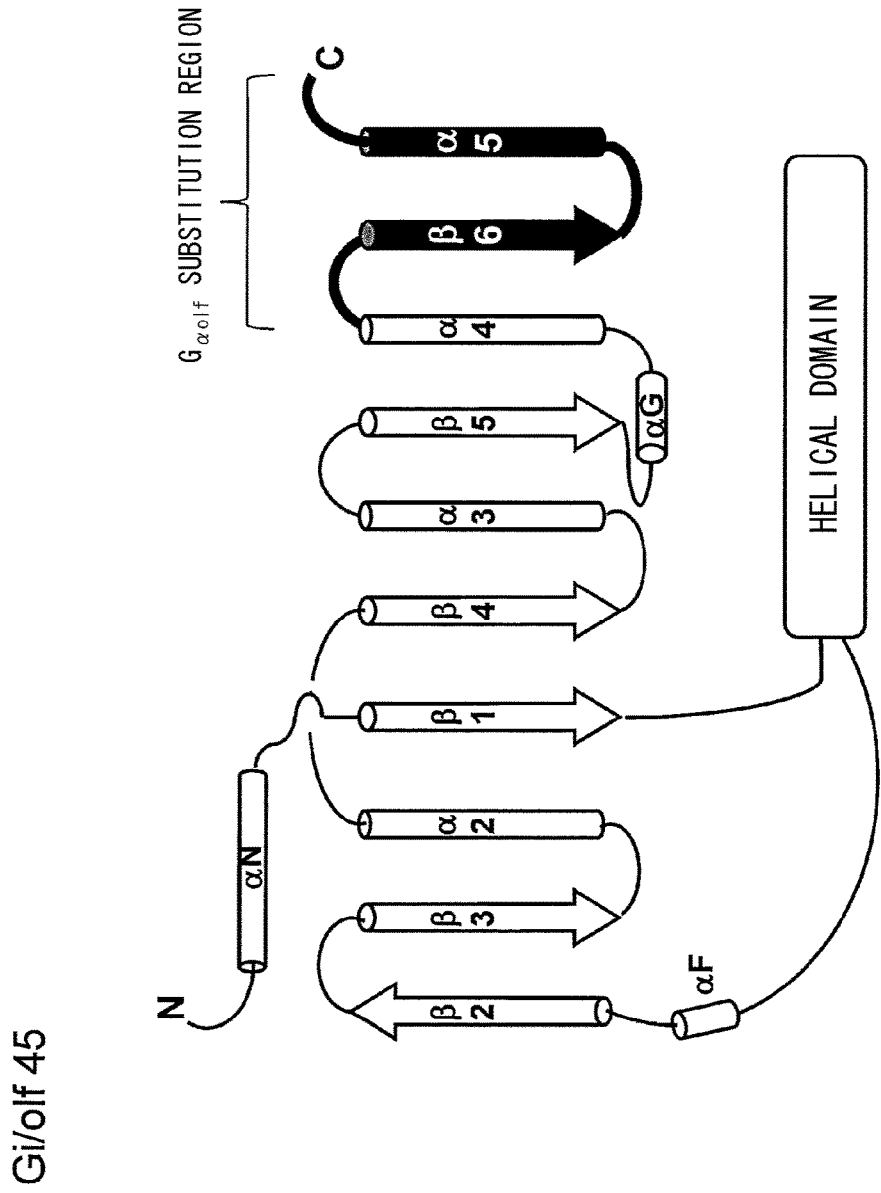
FIG. 9 schematically shows a secondary structure of $G_{i/olf45}$.

The amino acid sequence of a chimeric $G_\alpha$ subunit ($G_{i/olf45}$) used in Comparative Example 4 is shown below. FIG. 9 schematically shows a secondary structure of $G_{i/olf45}$.

```
                                        (SEQ ID NO: 6)
MGCTLSAEDKAAVERSKMIDRNLREDGEKAAREVKLLLLGAGESGKSTIV

KQMKIIHEAGYSEEECKQYKAVVYSNTIQSIIAIIRAMGRLKIDFGDSAR

ADDARQLFVLAGAAEEGFMTAELAGVIKRLWKDSGVQACFNRSREYQLND

SAAYYLNDLDRIAQPNYIPTQQDVLRTRVKTTGIVETHFTFKDLHFKMFD

VGGQRSERKKWIHCFEGVTAIIFCVALSDYDLVLAEDEEMNRMHESMKLF

DSICNNKWFTDTSIILFLNKKDLFEEKIKKSPLTICYPEYAGSNTYEEAA

AYIQCQFEDLNTATGDGKHYCYPHFTCAVDTENIRRVFNDCRDIIQRMHL

KQYELL
```

Figure 12:
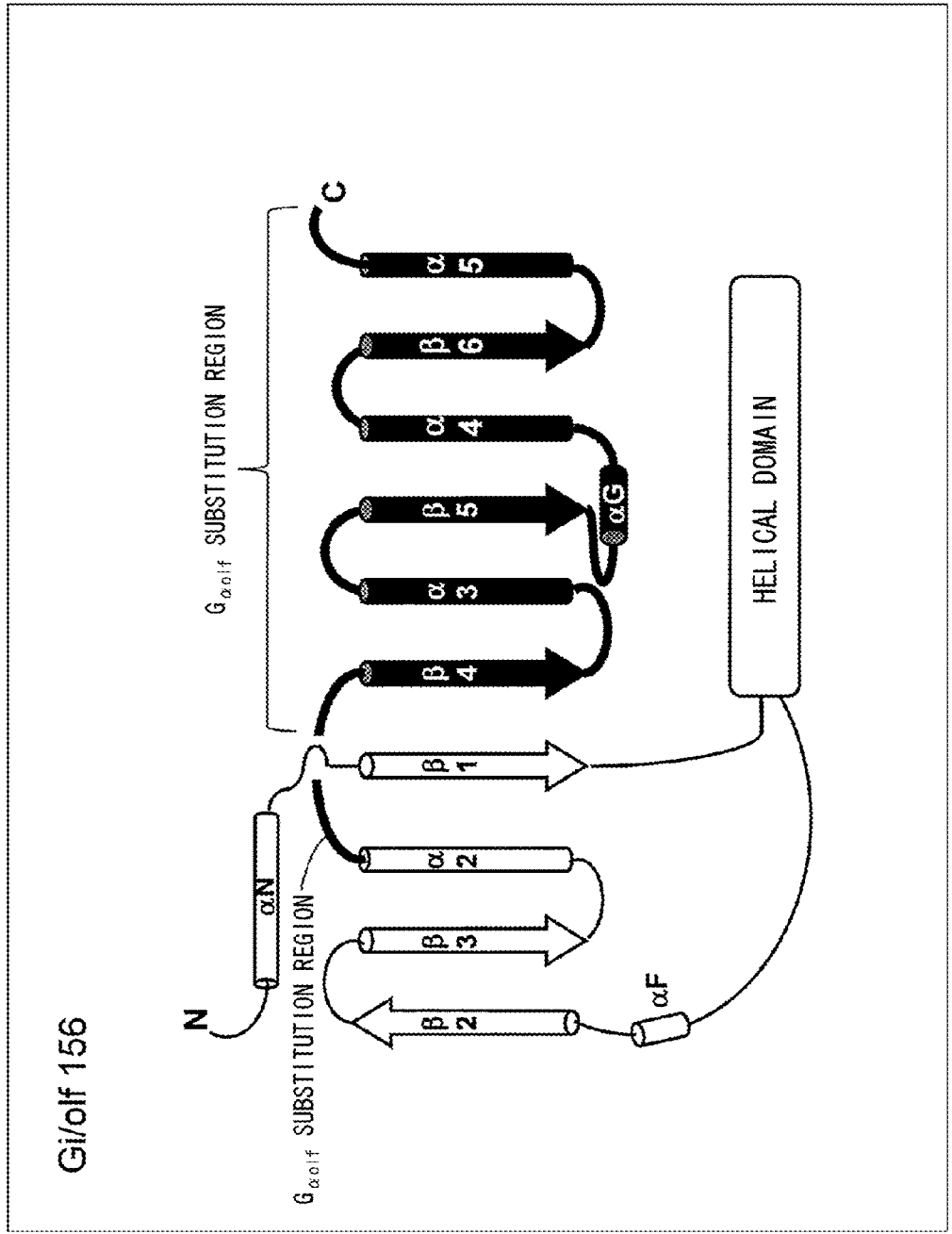
FIG. 12 schematically shows a secondary structure of $G_{i/olf156}$.

The amino acid sequence of $G_\alpha$ subunit ($G_{i/olf156}$) used in Comparative Example 5 is shown below. FIG. 12 schematically shows a secondary structure of $G_{i/olf156}$.

```
                                        (SEQ ID NO: 9)
MGCTLSAEDKAAVERSKMIDRNLREDGEKAAREVKLLLLGAGESGKSTIV

KQMKIIHEAGYSEEECKQYKAVVYSNTIQSIIAIIRAMGRLKIDFGDSAR

ADDARQLFVLAGAAEEGFMTAELAGVIKRLWKDSGVQACFNRSREYQLND

SAAYYLNDLDRIAQPNYIPTQQDVLRTRVKTTGIVETHFTFKDLHFKMFD

VGGQRSERKKWIHCFNDVTAIIYVAACSSYNMVIREDNNTNRLRESLDLF

ESIWNNRWLRTISIILFLNKQDMLAEKVLAGKSKIEDYFPEYANYTVPED

ATPDAGEDPKVTRAKFFIRDLFLRISTATGDGKHYCYPHFTCAVDTENIR

RVFNDCRDIIQRMHLKQYELL
```

Figure 13:
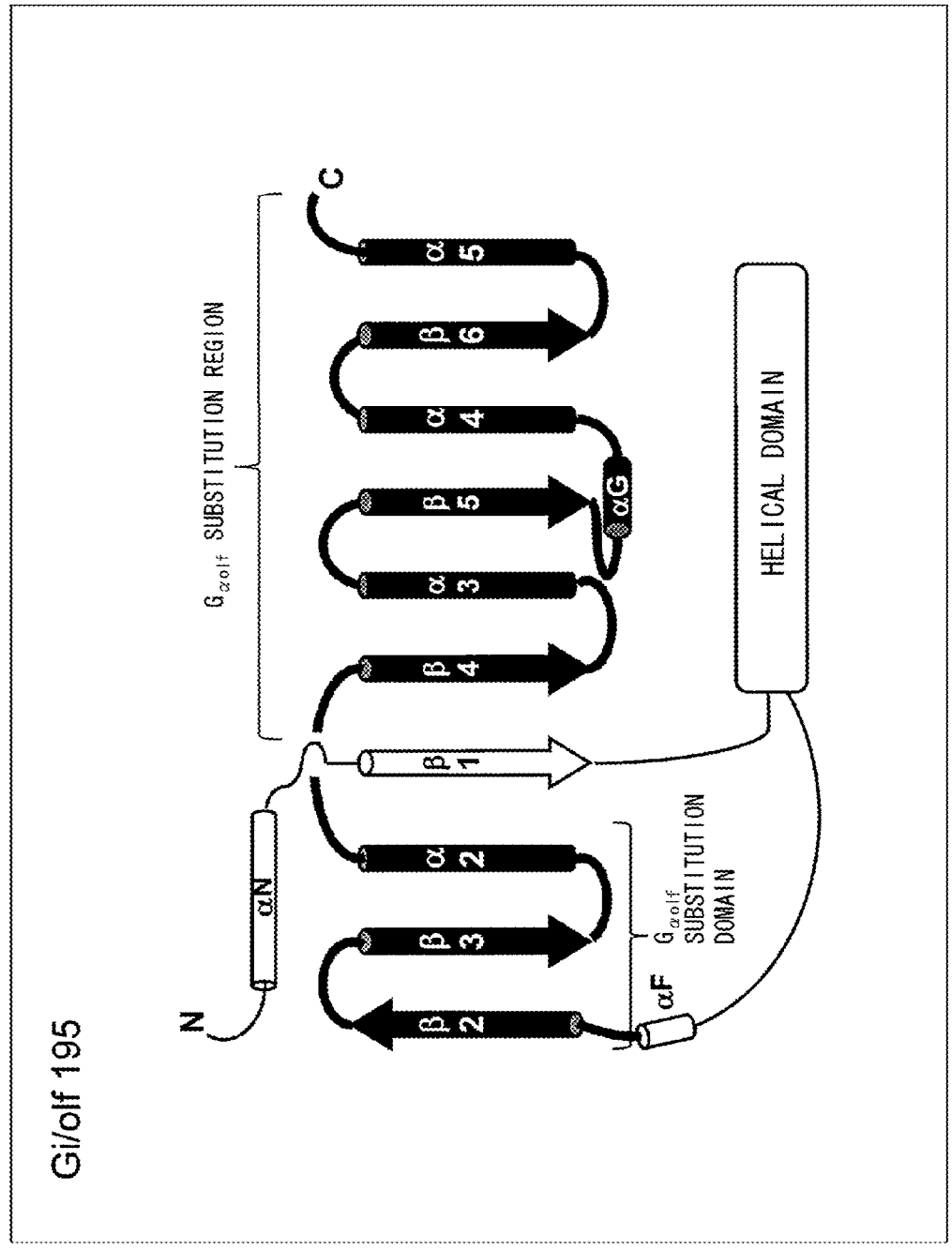
FIG. 13 schematically shows a secondary structure of $G_{i/olf195}$.

The amino acid sequence of a chimeric $G_\alpha$ subunit ($G_{i/olf195}$) used in Comparative Example 6 is shown below. FIG. 13 schematically shows a secondary structure of $G_{i/olf195}$.

```
                                        (SEQ ID NO: 10)
MGCTLSAEDKAAVERSKMIDRNLREDGEKAAREVKLLLLGAGESGKSTIV

KQMKIIHEAGYSEEECKQYKAVVYSNTIQSIIAIIRAMGRLKIDFGDSAR

ADDARQLFVLAGAAEEGFMTAELAGVIKRLWKDSGVQACFNRSREYQLND

SAAYYLNDLDRIAQPNYIPTQQDVLRCRVLTSGIFETRFQVDKVNFHMFD

VGGQRDERRKWIQCFNDVTAIIYVAACSSYNMVIREDNNTNRLRESLDLF

ESIWNNRWLRTISIILFLNKQDMLAEKVLAGKSKIEDYFPEYANYTVPED

ATPDAGEDPKVTRAKFFIRDLFLRISTATGDGKHYCYPHFTCAVDTENIR

RVFNDCRDIIQRMHLKQYELL
```

Figure 14:
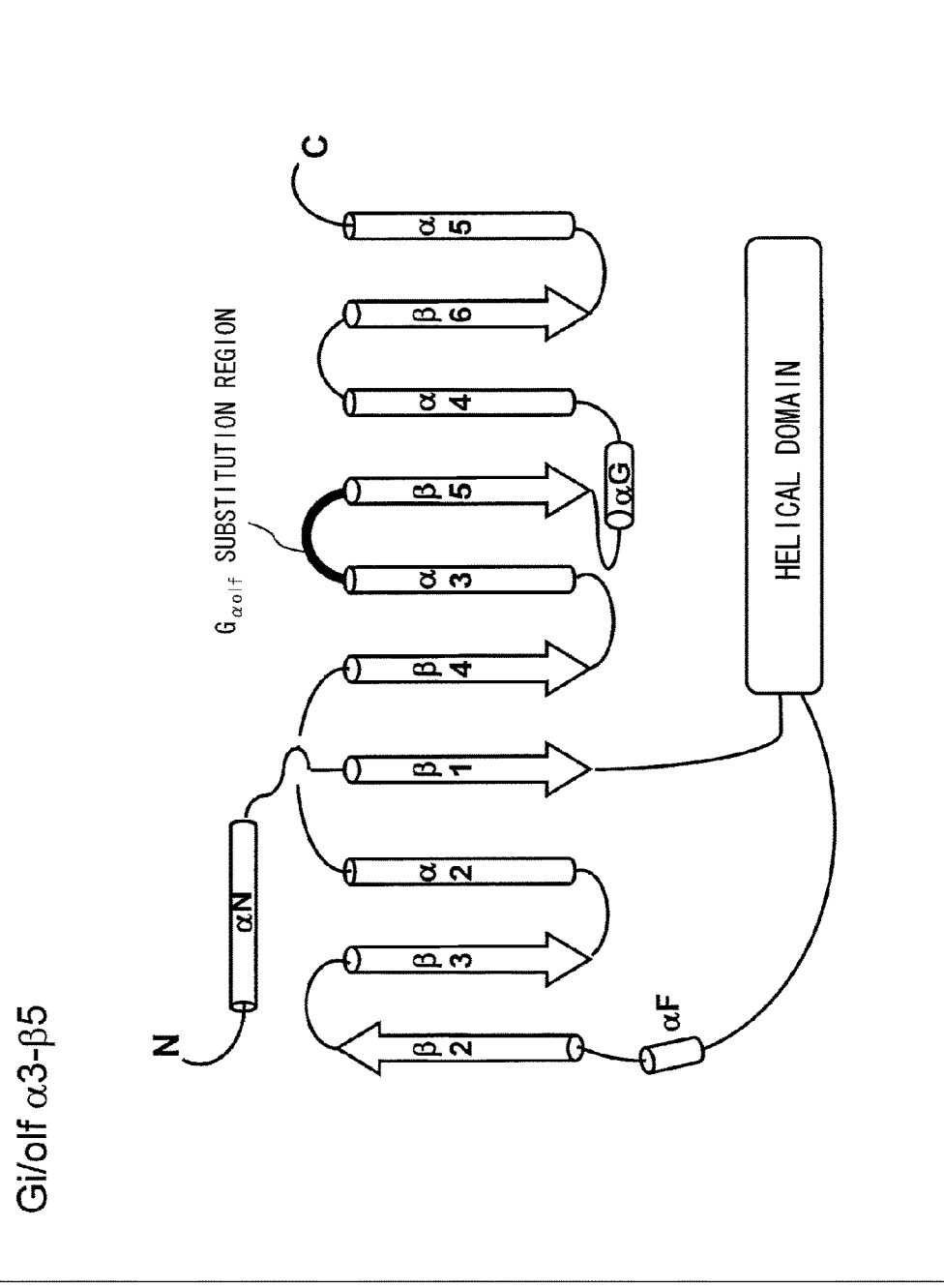
FIG. 14 schematically shows a secondary structure of $G_{i/olf\alpha3\text{-}\beta5}$.

The amino acid sequence of a chimeric $G_\alpha$ subunit ($G_{i/olf\alpha3-\beta5}$) used in Comparative Example 7 is shown below. FIG. 14 schematically shows a secondary structure of $G_{i/olf\alpha3-\beta5}$.

```
                                        (SEQ ID NO: 11)
MGCTLSAEDKAAVERSKMIDRNLREDGEKAAREVKLLLLGAGESGKSTIV

KQMKIIHEAGYSEEECKQYKAVVYSNTIQSIIAIIRAMGRLKIDFGDSAR

ADDARQLFVLAGAAEEGFMTAELAGVIKRLWKDSGVQACFNRSREYQLND

SAAYYLNDLDRIAQPNYIPTQQDVLRTRVKTTGIVETHFTFKDLHFKMFD

VGGQRSERKKWIHCFEGVTAIIFCVALSDYDLVLAEDEEMNRMHESMKLF

DSICNNKWLRTISIILFLNKKDLFEEKIKKSPLTICYPEYAGSNTYEEAA

AYIQCQFEDLNKRKDTKEIYTHFTCATDTKNVQFVFDAVTDVIIKNNLKD

CGLF
```

Figure 16:
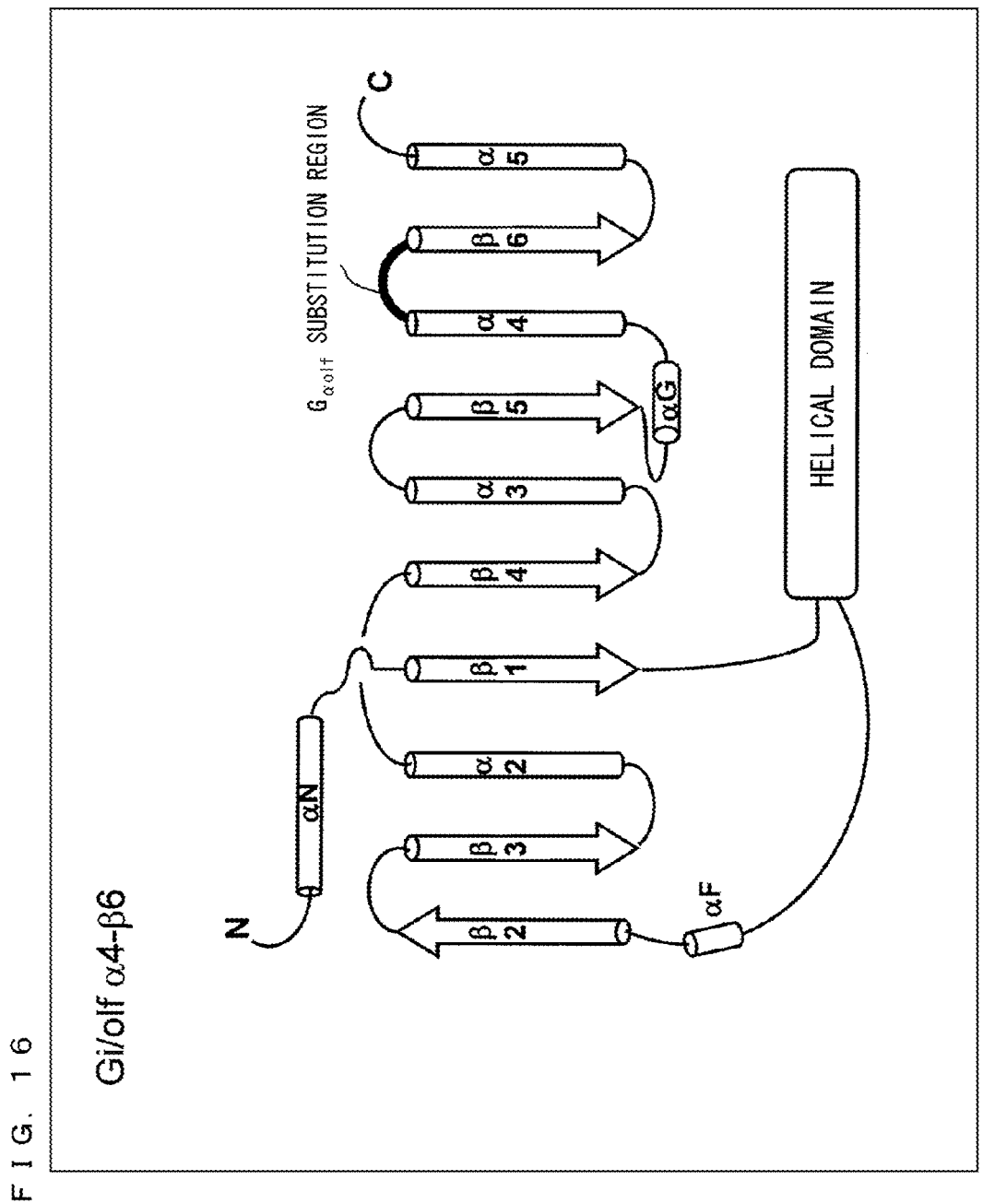
FIG. 16 schematically shows a secondary structure of $G_{i/olf\alpha4\text{-}\beta6}$.

The amino acid sequence of a chimeric $G_\alpha$ subunit ($G_{i/olf\alpha4-\beta6}$) used in Comparative Example 8 is shown below. FIG. 16 schematically shows a secondary structure of $G_{\alpha i/olf\alpha4-\beta6}$.

```
                                        (SEQ ID NO: 13)
MGCTLSAEDKAAVERSKMIDRNLREDGEKAAREVKLLLLGAGESGKSTIV

KQMKIIHEAGYSEEECKQYKAVVYSNTIQSIIAIIRAMGRLKIDFGDSAR

ADDARQLFVLAGAAEEGFMTAELAGVIKRLWKDSGVQACFNRSREYQLND

SAAYYLNDLDRIAQPNYIPTQQDVLRTRVKTTGIVETHFTFKDLHFKMFD

VGGQRSERKKWIHCFEGVTAIIFCVALSDYDLVLAEDEEMNRMHESMKLF

DSICNNKWFTDTSIILFLNKKDLFEEKIKKSPLTICYPEYAGSNTYEEAA

AYIQCQFEDLNTATGDGKHYCYTHFTCATDTKNVQFVFDAVTDVIIKNNL

KDCGLF
```

Figure 17:
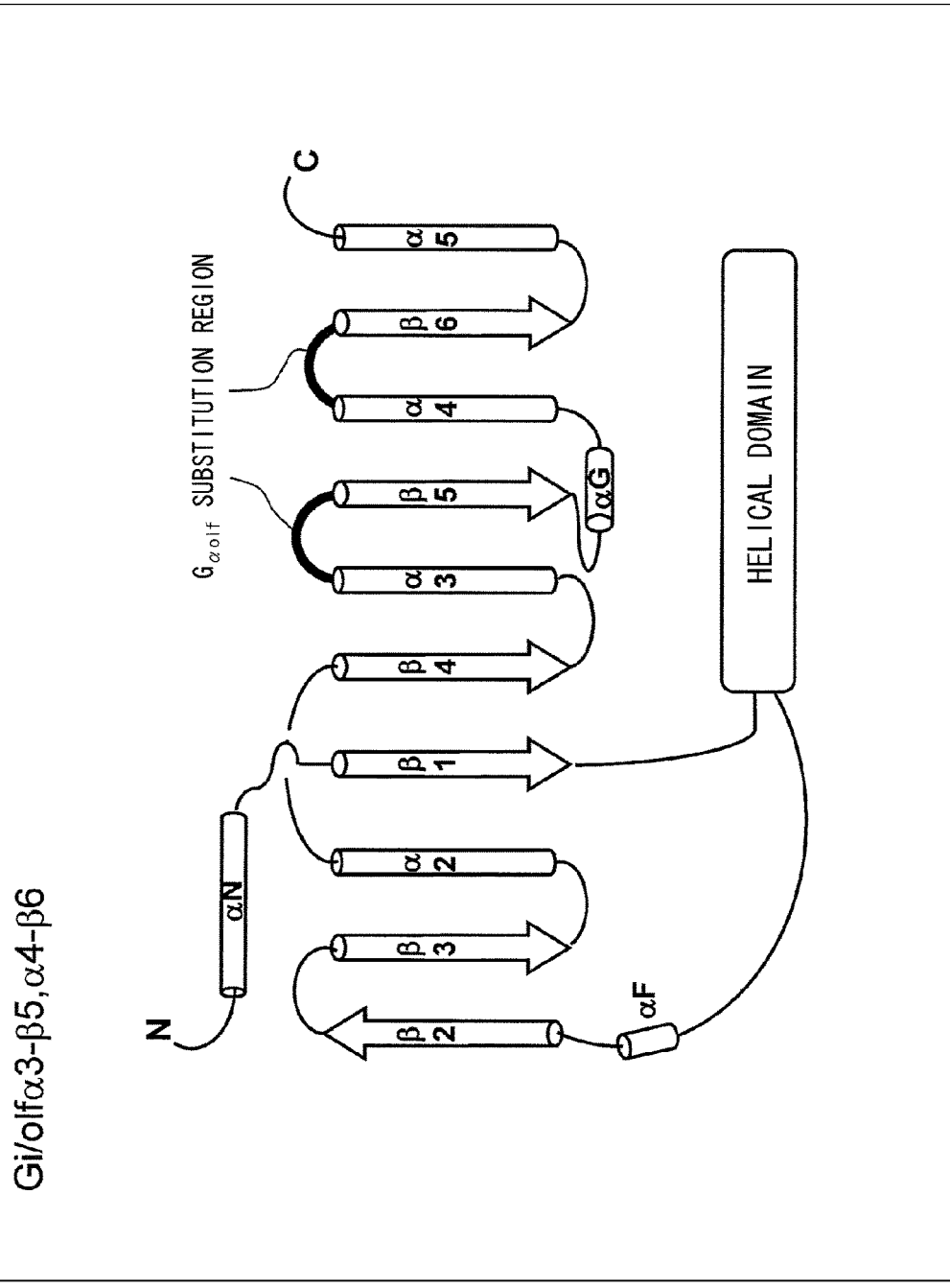
FIG. 17 schematically shows a secondary structure of $G_{i/olf\alpha3\text{-}\beta5,\alpha4\text{-}\beta6}$.

The amino acid sequence of a chimeric $G_\alpha$ subunit ($G_{i/olf\alpha3-\beta5,\alpha4-\beta6}$) used in Comparative Example 9 is shown below. FIG. 17 schematically shows a secondary structure of $G_{\alpha i/olf\alpha3-\beta5,\alpha4-\beta6}$.

```
                                                    (SEQ ID NO: 14)
MGCTLSAEDKAAVERSKMIDRNLREDGEKAAREVKLLLLGAGESGKSTIV

KQMKIIHEAGYSEEECKQYKAVVYSNTIQSIIAIIRAMGRLKIDFGDSAR

ADDARQLFVLAGAAEEGFMTAELAGVIKRLWKDSGVQACFNRSREYQLND

SAAYYLNDLDRIAQPNYIPTQQDVLRTRVKTTGIVETHFTFKDLHFKMFD

VGGQRSERKKWIHCFEGVTAIIFCVALSDYDLVLAEDEEMNRMHESMKLF

DSICNNKWLRTISIILFLNKKDLFEEKIKKSPLTICYPEYAGSNTYEEAA

AYIQCQFEDLNTATGDGKHYCYTHFTCATDTKNVQFVFDAVTDVIIKNNL

KDCGLF
```

The amino acid sequence of a chimeric $G_\alpha$ subunit ($G_{i/olf\alpha3\text{-}\beta5,\alpha4\text{-}\beta6,C}$) used in Comparative Example 10 is shown below. FIG. 19 schematically shows a secondary structure of $G_{i/olf\alpha3\text{-}\beta5,\alpha4\text{-}\beta6,C}$.

```
                                                    (SEQ ID NO: 16)
MGCTLSAEDKAAVERSKMIDRNLREDGEKAAREVKLLLLGAGESGKSTIV

KQMKIIHEAGYSEEECKQYKAVVYSNTIQSIIAIIRAMGRLKIDFGDSAR

ADDARQLFVLAGAAEEGFMTAELAGVIKRLWKDSGVQACFNRSREYQLND

SAAYYLNDLDRIAQPNYIPTQQDVLRTRVKTTGIVETHFTFKDLHFKMFD

VGGQRSERKKWIHCFEGVTAIIFCVALSDYDLVLAEDEEMNRMHESMKLF

DSICNNKWLRTISIILFLNKKDLFEEKIKKSPLTICYPEYAGSNTYEEAA

AYIQCQFEDLNTATGDGKHYCYTHFTCATDTKNVQFVFDAVTDIIQRMHL

KQYELL
```

Figure 30:
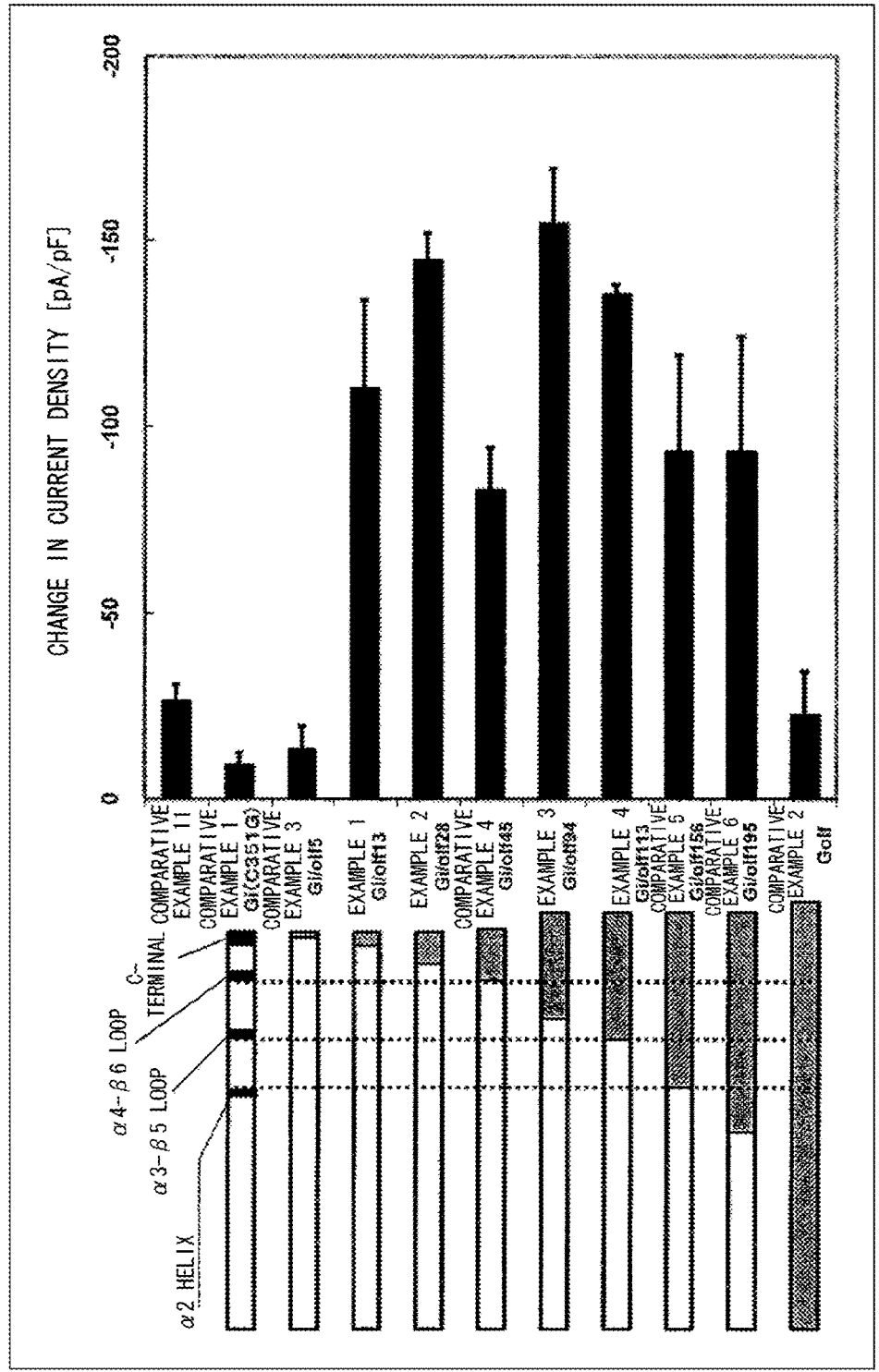
FIG. 30 shows changes in ionic current of G protein expressing cells.
Figure 31:
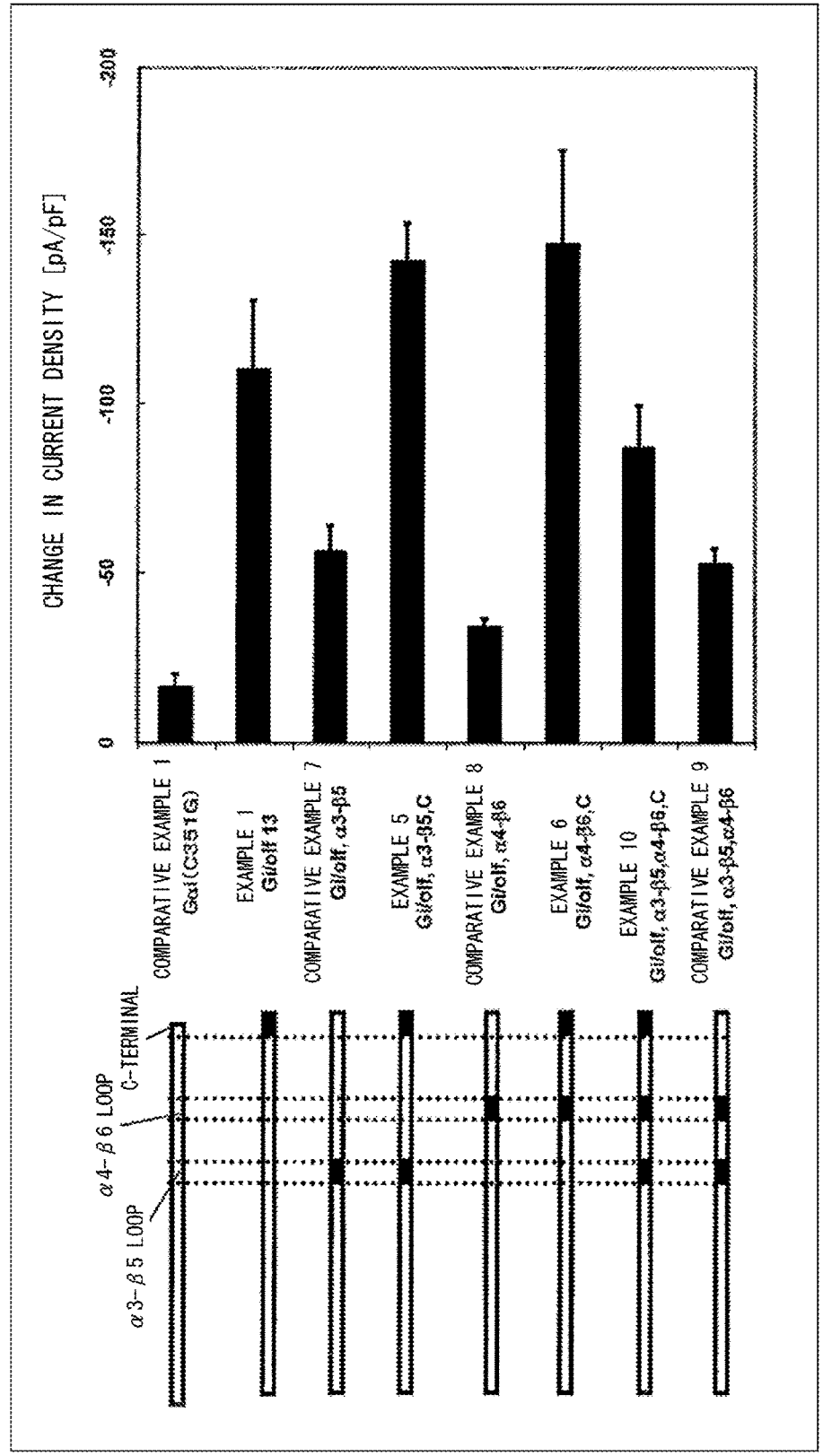
FIG. 31 shows changes in ionic current of G protein expressing cells.

Table 11 and FIG. 30 show measurement results from Examples 1 to 4, Comparative Examples 1 to 6, and Comparative Example 11. The measurement results are shown as change levels in current density, i.e., a difference between current densities (current value/cell membrane capacity) of membrane current measured when ISO was not supplied and when ISO was supplied.

TABLE 11

|  | $G_\alpha$ subunit | Change Level in Current Density [pA/pF] | Limit of Error |
|---|---|---|---|
| Comparative Example 11 |  | −26.29 | 3.38 |
| Comparative Example 1 | $G_{\alpha i}$ (C351G) | −9.14 | 3.36 |
| Comparative Example 3 | $G_{i/olf5}$ | −13.37 | 6.05 |
| Example 1 | $G_{i/olf13}$ | −110.50 | 20.36 |
| Example 2 | $G_{i/olf28}$ | −144.91 | 30.42 |
| Comparative Example 4 | $G_{i/olf45}$ | −83.20 | 17.00 |
| Example 3 | $G_{i/olf94}$ | −154.64 | 22.14 |
| Example 4 | $G_{i/olf113}$ | −135.63 | 15.71 |
| Comparative Example 5 | $G_{i/olf156}$ | −93.32 | 19.35 |
| Comparative Example 6 | $G_{i/olf195}$ | −93.49 | 8.57 |
| Comparative Example 2 | $G_{\alpha olf}$ | −22.59 | 3.70 |

Table 12 and FIG. 30 show measurement results from Example 1, Example 5, Example 6, Comparative Example 1, and Comparative Examples 7 to 10. The measurement results are shown as amounts of change in current densities, i.e., a difference between current density (current value/cell membrane capacity) of membrane current measured when ISO was not supplied and when ISO was supplied.

TABLE 12

|  | $G_\alpha$ subunit | Change Level in Current Density [pA/pF] | Limit of Error |
|---|---|---|---|
| Comparative Example 1 | $G_{\alpha i}$ (C351G) | −16.37 | 4.19 |
| Example 1 | $G_{i/olf13}$ | −110.50 | 20.36 |
| Comparative Example 7 | $G_{i/olf\alpha3\text{-}\beta5}$ | −56.66 | 7.76 |
| Example 5 | $G_{i/olf\alpha3\text{-}\beta5,C}$ | −142.54 | 11.47 |
| Comparative Example 8 | $G_{i/olf\alpha4\text{-}\beta6}$ | −34.15 | 2.63 |
| Example 6 | $G_{i/olf\alpha4\text{-}\beta6,C}$ | −147.49 | 28.15 |
| Comparative Example 10 | $G_{i/olf\alpha3\text{-}\beta5,\alpha4\text{-}\beta6,C}$ | −86.88 | 12.85 |
| Comparative Example 9 | $G_{i/olf\alpha3\text{-}\beta5,\alpha4\text{-}\beta6}$ | −52.78 | 5.00 |

(Comparison to Camp Technique)

Chemical substance detection sensitivity according to the present invention was compared to detection sensitivity of cAMP technique, which is a commonly used chemical substance detection technique. The cAMP technique is a technique for measuring an increase in cAMP concentration in an intracellular fluid caused by an interaction between an agonist and a receptor, and quantifying the concentration of the agonist based on the measured value. More particularly, cells expressing β1 adrenergic receptor and potassium ion channel Kir3.1 (F137S) were placed in contact with a buffer solution containing ISO, and then were homogenized. The concentration of cAMP contained in the obtained homogenate liquid was measured. The concentration measurement was performed by using a measurement kit (cyclic AMP EIA kit; Assay Designs, Inc.). The kit measures cAMP concentration by utilizing competitive EIA (competitive enzyme immunoassay). A cAMP concentration obtained when the ISO concentration inside of a buffer solution was 1000 nM was represented as 100 as a standard, and cAMP concentrations at respective ISO concentrations were calculated as ratios with regard to this standard cAMP concentration. On the other hand, measurements were conducted similarly to Example 3, except that the measurements were conducted by changing the ISO concentration. A change value in current density obtained when the ISO concentration was 30 nM was represented as 100 as a standard, and change values in current density at respective ISO concentrations were calculated as ratios with regard to the standard change value. Table 13 and FIG. 32 show the results.

TABLE 13

| ISO Concentration (nM) | cAMP technique | Present Invention |
|---|---|---|
| 0 | 9.56 | — |
| 0.01 | 2.95 | — |
| 0.03 | 1.78 | 2.34 |
| 0.1 | 3.00 | — |
| 0.3 | 4.25 | 19.22 |
| 1 | 3.21 | 48.01 |
| 3 | — | 78.00 |
| 10 | 9.95 | — |
| 30 | — | 100 |
| 100 | 44.66 | — |
| 300 | 93.82 | 95.94 |
| 1000 | 100 | — |
| 3000 | — | — |

Figure 32:
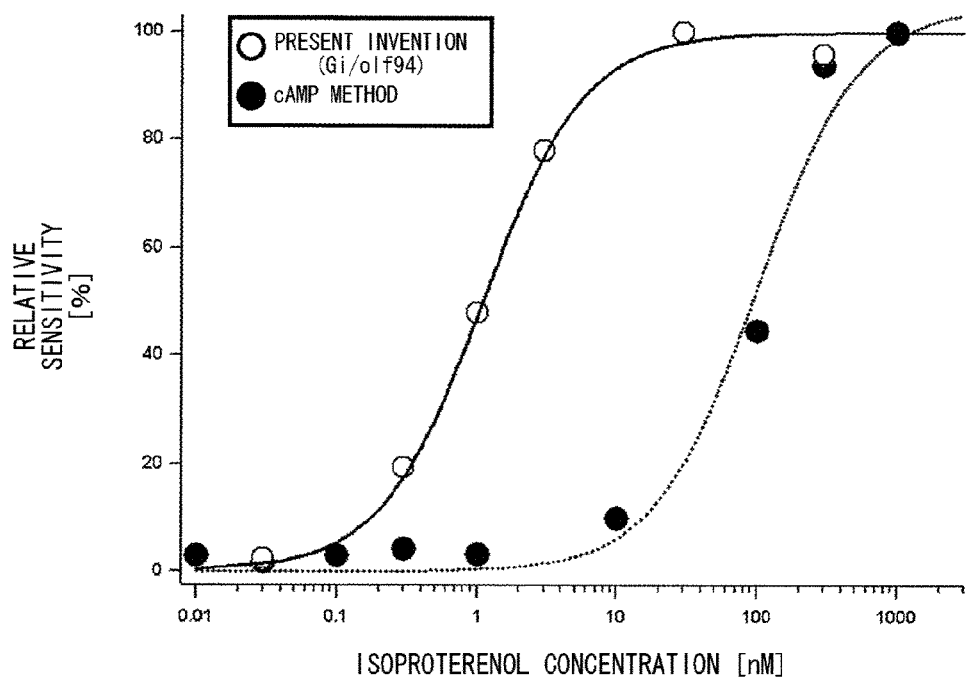
FIG. 32 indicates an advantage of a chemical sensor of the present invention over a conventional chemical substance detection method.

The following describes what is understood from Table 13 and FIG. 32. A detectable lower limit of ISO concentration when using cAMP technique is thought to be approximately 10 nM. This is because an ISO concentration-dependent increase in the cAMP concentration was not observed upon contact with a buffer solution having an ISO concentration of 0 to 1 nM. A half maximal effective concentration ($EC_{50}$) of ISO, which is an index of ISO detection sensitivity, with regard to β1 adrenergic receptor was 135 nM. On the other hand, with the method according to the present invention using the chimeric α subunit $G_{i/olf94}$ protein, the lower limit of detection concentration of ISO was 0.3 nM. The change level in ionic current saturated at an ISO concentration of approximately 30 nM. In this case, the half maximal effective concentration of ISO was 1 nM with regard to β1 adrenergic receptor. With the chemical substance detection method using the chimeric $G_\alpha$ subunit protein of the present invention, ISO can be detected with sensitivity approximately 100 times higher than a conventional generally-used cAMP technique. It is thought that the highly sensitive detection was enabled since bindings of chemical substances to receptors have been directly transferred to ion channels via chimeric G proteins without depending on a complicated intermolecular reaction within cells.

(Detection of β Adrenergic Receptor Agonist)

Figure 33:
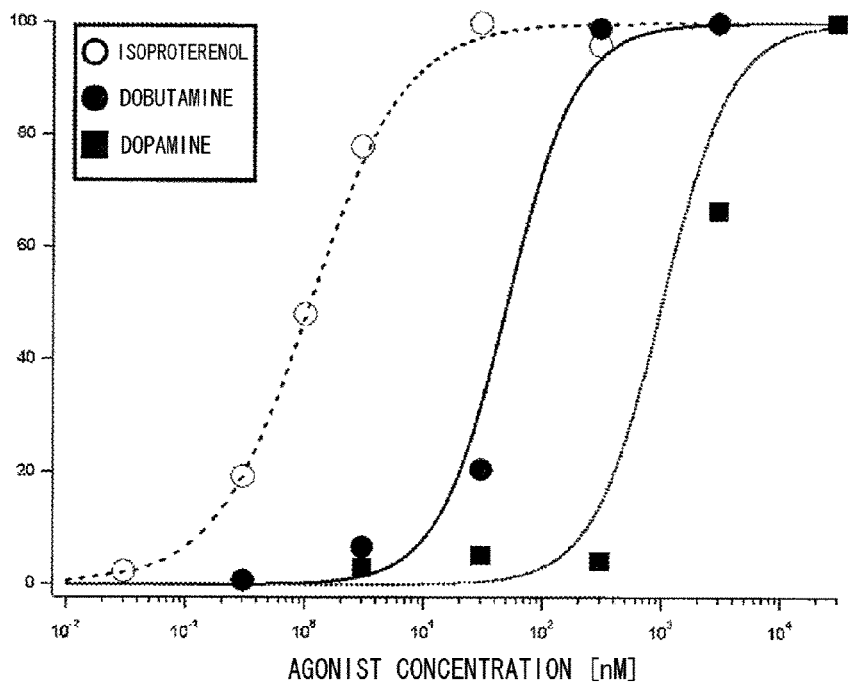
FIG. 33 shows dependence of potassium ion current of chimeric G protein expressing cells over concentrations of various chemical substances.

Detections of β1 agonists other than isoproterenol were conducted. Measurements were conducted similarly to Example 3, except for using, in addition to ISO as chemical substances, dobutamine, which is a selective agonist of β1 adrenergic receptor, and dopamine which is an agonist of β adrenergic receptor. Table 14 and FIG. 33 show measurement results. Change values in current density observed at concentrations of 30000 nM for dopamine, 100 nM for dobutamine, and 30 nM for ISO were each represented as 100, and measurement results were described as relative values with regard to those.

TABLE 14

| Concentration | Change Level in Current Density | | |
|---|---|---|---|
| [nM] | dopamine | dobutamine | isoproterenol |
| 0.03 | — | — | 2.34 |
| 0.3 | — | 0.67 | 19.22 |
| 1 | — | — | 48.01 |
| 3 | 3.07 | 6.80 | 78.01 |
| 30 | 5.32 | 20.59 | 100 |
| 300 | 4.11 | 99.15 | 95.94 |
| 3000 | 66.61 | 100 | — |
| 30000 | 100 | — | — |

With every agonist used, the change values in current density increased in association with increases in agonist concentrations. The $EC_{50}$ values for dopamine and dobutamine were 1000 nM and 50 nM, respectively. It is reasonably presumed that a change in current density is generated by agonists activating chimeric G proteins via chemical substance receptors and opening gates of ion channels. This is because the $EC_{50}$ values are different depending on the type of agonist. Therefore, agonists are not directly but indirectly activating chimeric G proteins.

Reference Example

The present inventors examined the following in advance of the present invention, and determined a design plan for the chimeric $G_\alpha$ subunits. $G_{\alpha i}$ (C351G), $G_{\alpha olf}$ and $G_{i/olf13}$ were used as $G_\alpha$ subunits to measure ionic current generated upon contact with ISO. The measurements were conducted in accordance with a method similar to that in Example 1.

Figure 26:
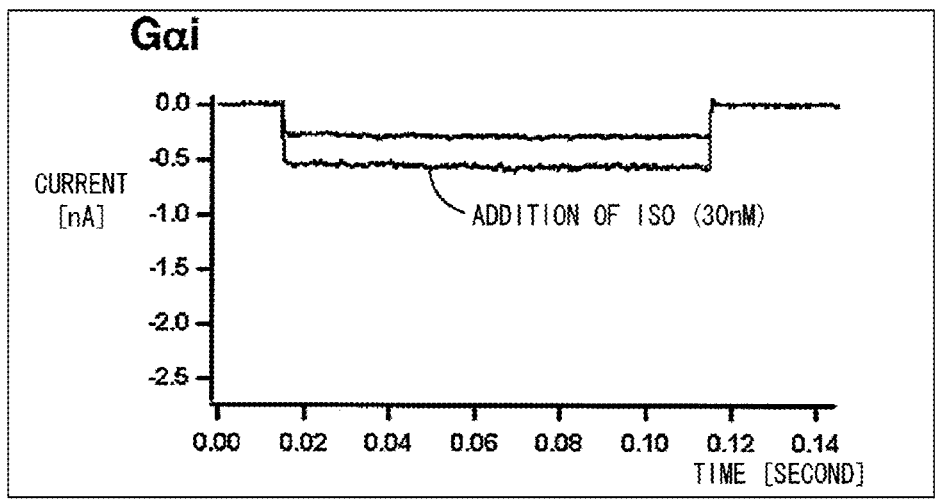
FIG. 26 indicates ionic current of $G_{\alpha i}$ (C351G) protein expressing cells.

As shown in FIG. 26, when $G_{\alpha i}$ (C351G) was used as the chimeric $G_\alpha$ subunit and when ISO was not supplied, a current value of approximately −0.2 nA was measured immediately after a pulse wave was applied. Here, the current value being "−" (negative) indicates that potassium ions have moved from a front side to a back side of a lipid bilayer membrane (from outside to inside a cell). When ISO was supplied, the current value changed and became approximately 0.5 nA.

Figure 27:
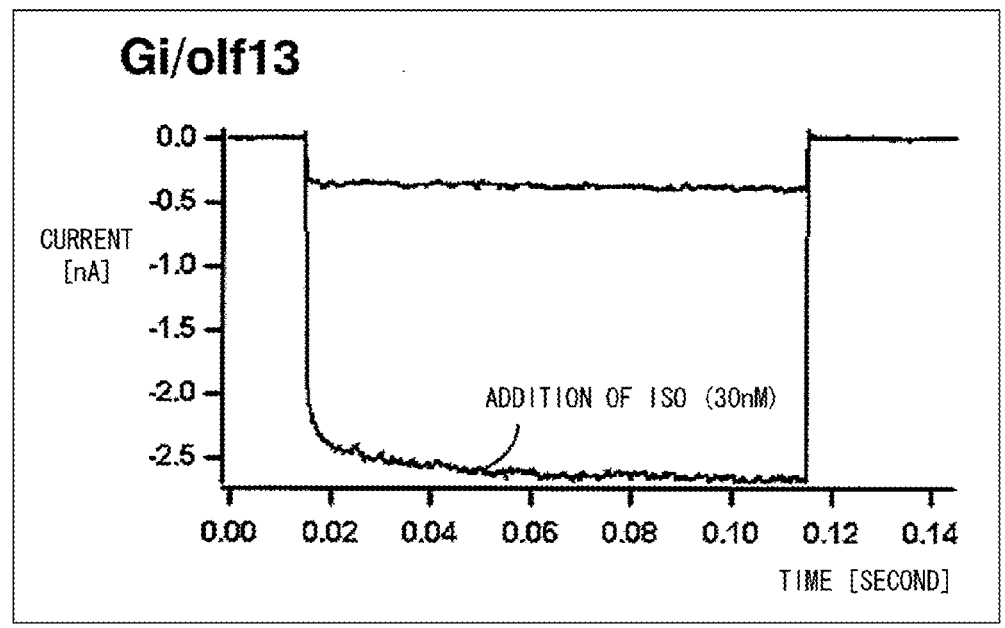
FIG. 27 indicates ionic current of $G_{i/olf13}$ protein expressing cells.
Figure 28:
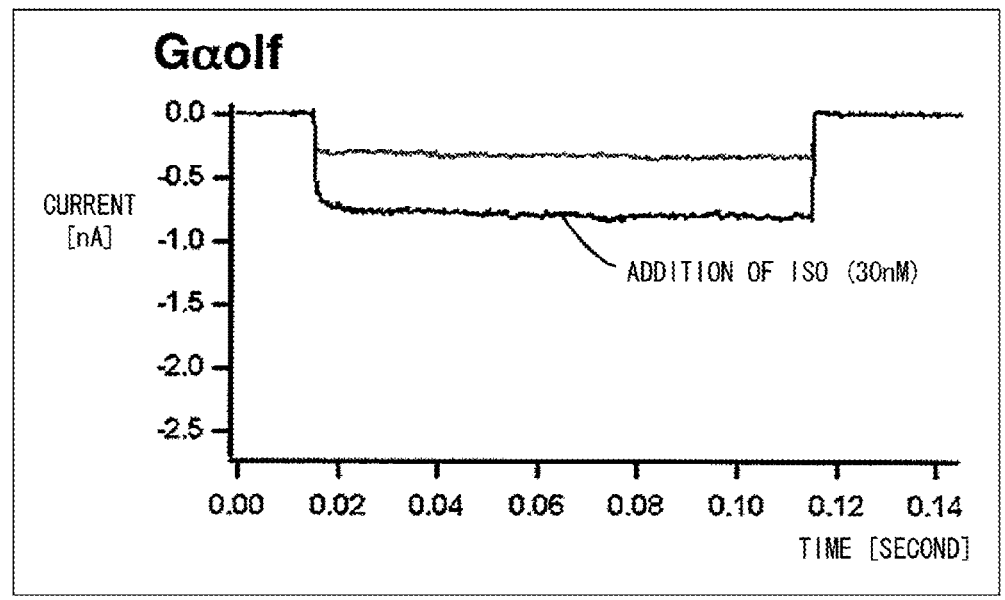
FIG. 28 indicates ionic current of wild type $G_{\alpha olf}$ protein expressing cells.

As shown in FIG. 27, when $G_{i/olf13}$ was used as the chimeric $G_\alpha$ subunit, the current value changed due to having ISO supplied and became approximately −2.5 nA. As shown in FIG. 28, when $G_{\alpha olf}$ protein was used as the chimeric $G_\alpha$ subunit, a current value of approximately 0.5 nA was measured similarly to the case where $G_{\alpha i}$ (C351G) was used, and change level of current value caused by an addition of ISO was small.

The present inventors derived the following conclusion from the above described measurement results. $G_{\alpha i}$ (C351G) can activate potassium ion channels but cannot bind to chemical substance receptors. $G_{\alpha olf}$ can bind to chemical substance receptors but cannot activate potassium ion channels. Thus, the current change level caused by the addition of ISO was small. On the other hand, when $G_{i/olf13}$ was used, a large current change was observed caused by the addition of ISO, since the chimeric $G_\alpha$ subunit can bind to chemical substance receptors via the $G_{\alpha olf}$ region at the C-terminal and the $G_{\alpha i}$ region activates potassium ion channels. Therefore, the chimerization of the $G_\alpha$ subunit increases the current change level caused by the addition of ISO.

Figure 29:
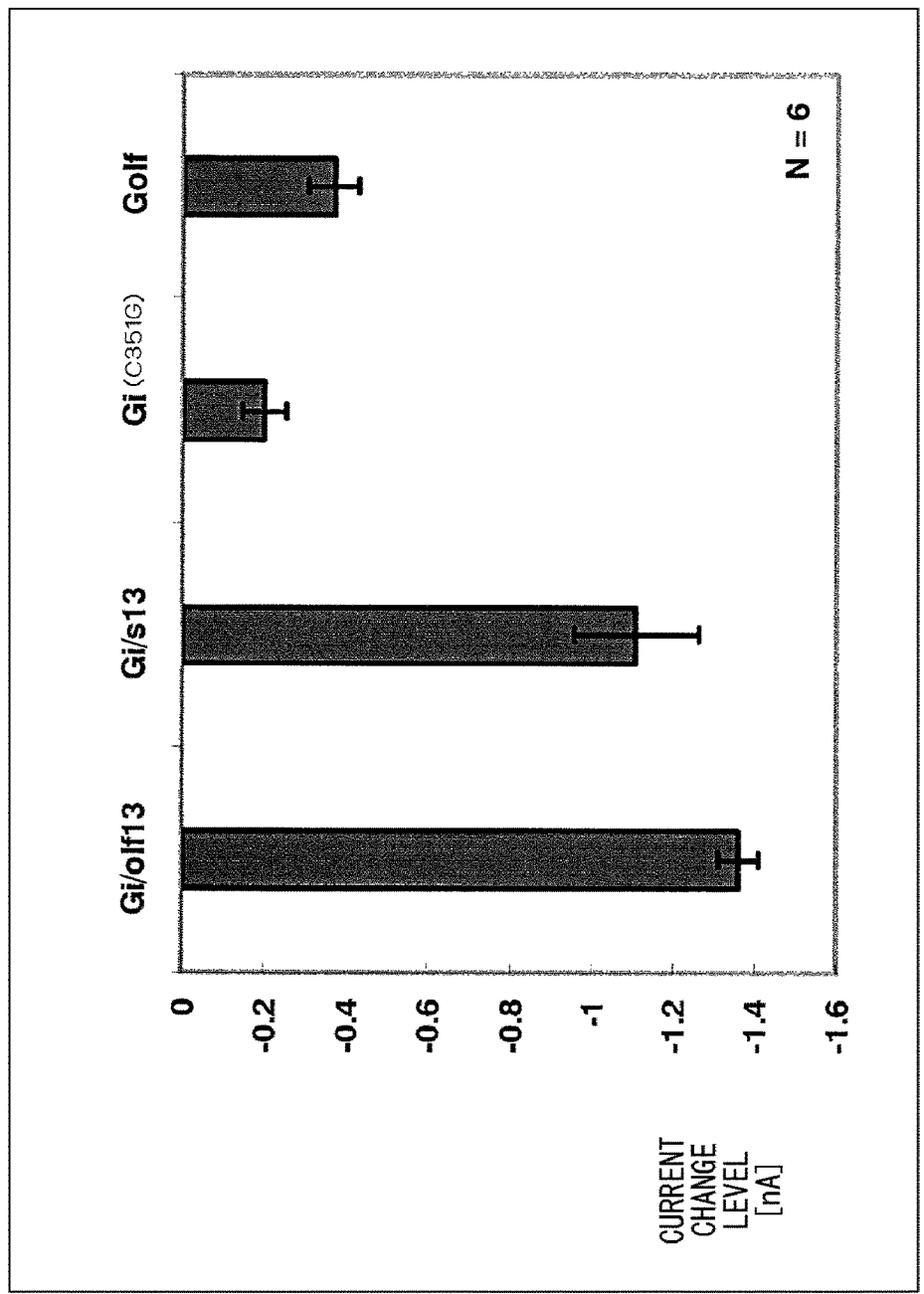
FIG. 29 shows changes in ionic current of chimeric G protein expressing cells.

Furthermore, a current change level obtained when $G_{i/s13}$ was used as the chimeric $G_\alpha$ subunit was compared to a current change level obtained when $G_{i/olf13}$ was used as the chimeric $G_\alpha$ subunit. Table 15 and FIG. 29 show measurement results. The measurement results obtained when $G_{\alpha i}$ (C351G) and $G_{olf}$ apply were used are shown on the side as references.

TABLE 15

| | $G_{i/olf13}$ | $G_{i/s13}$ | $G_{\alpha i}$ (C351G) | $G_{\alpha olf}$ |
|---|---|---|---|---|
| Current Change Level [nA] | −1.36 | −1.11 | −0.20 | −0.37 |
| Limit of Error | 0.05 | 0.15 | 0.05 | 0.06 |

The current change level obtained when $G_{i/olf13}$ was used was larger than the current change level obtained when $G_{i/s13}$ was used. Therefore, it was determined that larger current changes can be expected when a chimera of $G_{\alpha i}$ and $G_{\alpha olf}$ were used. Hence, it was determined to create a chimeric $G_\alpha$ subunit in which a region generally considered to participate in the coupling with a chemical substance receptor in the amino acid sequence of $G_{\alpha i}$ was substituted with a corresponding amino acid sequence of $G_{\alpha olf}$.

INDUSTRIAL APPLICABILITY

According to a chimeric G protein of the present invention, a detection of a chemical substance that binds to a chemical substance receptor is enabled.

What is claimed is:

1. A method for transporting potassium ions from a front side of a lipid bilayer membrane to a back side thereof, the method comprising the following steps (a) and (b):

step (a) of preparing the lipid bilayer membrane, wherein the lipid bilayer membrane comprises a G protein-coupled receptor, a G protein, and a G protein-coupled inwardly rectifying potassium ion channel, the G protein comprises a chimeric $G_\alpha$ subunit and a $G_{\beta\gamma}$ subunit complex, and the chimeric $G_\alpha$ subunit consists of any one of $G_{i/olf13}$ (SEQ ID NO: 04), $G_{i/olf28}$ (SEQ ID NO: 05), $G_{i/olf94}$ (SEQ ID NO: 07), $G_{i/olf113}$ (SEQ ID NO: 08), $G_{i/olf\alpha3-\beta5,C}$ (SEQ ID NO: 12), or $G_{i/olf\alpha4-\beta6,C}$ (SEQ ID NO: 15); and step (b) of supplying an agonist of said G protein-coupled receptor and the potassium ions to the front side to release the chimeric $G_\alpha$ subunit and $G_{\beta\gamma}$ subunit complex, and to allow the $G_{\beta\gamma}$ subunit complex to bind to the potassium ion channel for transporting the potassium ions from the front side to the back side.

2. The method according to claim 1, wherein the agonist of said G protein-coupled receptor is an adrenergic receptor agonist.

3. A method for detecting or quantifying a G protein-coupled receptor agonist, the method comprising the following steps (c), (d), and (e):

step (c) of preparing a lipid bilayer membrane, a first liquid located on a front side of the lipid bilayer membrane, and a second liquid located on a back side of the lipid bilayer membrane, wherein the lipid bilayer membrane comprises a G protein-coupled receptor, a G protein, and a G protein-coupled inwardly rectifying potassium ion channel, the G protein comprises a chimeric $G_\alpha$ subunit and a $G_{\beta\gamma}$ subunit complex, the chimeric $G_\alpha$ subunit consists of any one of $G_{i/olf13}$ (SEQ ID NO: 04), $G_{i/olf28}$ (SEQ ID NO: 05), $G_{i/olf94}$ (SEQ ID NO: 07), $G_{i/olf113}$ (SEQ ID NO: 08), $G_{i/olf\alpha3-\beta5,C}$ (SEQ ID NO: 12), or $G_{i/olf\alpha4-\beta6,C}$ (SEQ ID NO: 15), and the first liquid contains potassium ions;

step (d) of supplying the G protein-coupled receptor agonist to the first liquid; and step (e) of measuring an amount of potassium ions in at least one of the first and second liquids to detect or quantify the G protein-coupled receptor agonist based on the amount of the potassium ions.

4. The method according to claim 3, wherein the G protein-coupled receptor agonist is an adrenergic receptor agonist.

5. A method for detecting or quantifying a G protein-coupled receptor agonist, the method comprising the following steps (f), (g), and (h):

step (f) of preparing a lipid bilayer membrane, wherein the lipid bilayer membrane comprises a G protein-coupled receptor, a G protein, and a G protein-coupled inwardly rectifying potassium ion channel, the G protein comprises a chimeric $G_\alpha$ subunit and a $G_{\beta\gamma}$ subunit complex, and the chimeric $G_\alpha$ subunit consists of any one of $G_{i/olf13}$ (SEQ ID NO: 04), $G_{i/olf28}$ (SEQ ID NO: 05), $G_{i/olf94}$ (SEQ ID NO: 07), $G_{i/olf13}$ (SEQ ID NO: 08), $G_{i/olf\alpha3-\beta5,C}$ (SEQ ID NO: 12), or $G_{i/olf\alpha4-\beta6,C}$ (SEQ ID NO: 15);

step (g) of supplying a first liquid and a second liquid located respectively on a front side and a back side of the lipid bilayer membrane such that the lipid bilayer membrane is interposed between the first liquid and second liquid, wherein the first liquid contains potassium ions and the G protein-coupled receptor agonist; and step (h) of measuring an amount of potassium ions in at least one of the first and second liquids to detect or quantify the G protein-coupled receptor agonist based on the amount of the potassium ions.

6. The method according to claim 5, wherein the G protein-coupled receptor agonist is an adrenergic receptor agonist.

* * * * *

SEQUENCE LISTING

<160> NUMBER OF SEQ ID NOS: 78

<210> SEQ ID NO 1
<211> LENGTH: 354
<212> TYPE: PRT
<213> ORGANISM: Mus musculus
<220> FEATURE:
<221> NAME/KEY: MISC_FEATURE
<222> LOCATION: (1)..(354)
<223> OTHER INFORMATION: Spleen of Mouse

<400> SEQUENCE: 1

Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Ala Gly Tyr Ser Glu Glu
    50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
        115                 120                 125

Arg Leu Trp Lys Asp Ser Gly Val Gln Ala Cys Phe Asn Arg Ser Arg
    130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
        195                 200                 205

Lys Lys Trp Ile His Cys Phe Glu Gly Val Thr Ala Ile Ile Phe Cys
    210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Phe Thr Asp Thr Ser Ile Ile Leu Phe Leu Asn Lys Lys Asp
            260                 265                 270

Leu Phe Glu Glu Lys Ile Lys Lys Ser Pro Leu Thr Ile Cys Tyr Pro
        275                 280                 285

Glu Tyr Ala Gly Ser Asn Thr Tyr Glu Glu Ala Ala Ala Tyr Ile Gln
    290                 295                 300

Cys Gln Phe Glu Asp Leu Asn Lys Arg Lys Asp Thr Lys Glu Ile Tyr
305                 310                 315                 320

Thr His Phe Thr Cys Ala Thr Asp Thr Lys Asn Val Gln Phe Val Phe
                325                 330                 335

Asp Ala Val Thr Asp Val Ile Ile Lys Asn Asn Leu Lys Asp Ile Gly

-continued

```
                340                 345                 350
Leu Phe

<210> SEQ ID NO 2
<211> LENGTH: 381
<212> TYPE: PRT
<213> ORGANISM: Mus musculus
<220> FEATURE:
<221> NAME/KEY: MISC_FEATURE
<222> LOCATION: (1)..(381)
<223> OTHER INFORMATION: bulbus olfactorius of mouse

<400> SEQUENCE: 2

Met Gly Cys Leu Gly Asn Ser Ser Lys Thr Ala Glu Asp Gln Gly Val
1               5                   10                  15

Asp Glu Lys Glu Arg Arg Glu Ala Asn Lys Lys Ile Glu Lys Gln Leu
            20                  25                  30

Gln Lys Glu Arg Leu Ala Tyr Lys Ala Thr His Arg Leu Leu Leu Leu
        35                  40                  45

Gly Ala Gly Glu Ser Gly Lys Ser Thr Ile Val Lys Gln Met Arg Ile
    50                  55                  60

Leu His Val Asn Gly Phe Asn Pro Glu Glu Lys Lys Gln Lys Ile Leu
65                  70                  75                  80

Asp Ile Arg Lys Asn Val Lys Asp Ala Ile Val Thr Ile Val Ser Ala
                85                  90                  95

Met Ser Thr Ile Ile Pro Pro Val Pro Leu Ala Asn Pro Glu Asn Gln
            100                 105                 110

Phe Arg Ser Asp Tyr Ile Lys Ser Ile Ala Pro Ile Thr Asp Phe Glu
        115                 120                 125

Tyr Ser Gln Glu Phe Phe Asp His Val Lys Lys Leu Trp Asp Asp Glu
    130                 135                 140

Gly Val Lys Ala Cys Phe Glu Arg Ser Asn Glu Tyr Gln Leu Ile Asp
145                 150                 155                 160

Cys Ala Gln Tyr Phe Leu Glu Arg Ile Asp Ser Val Ser Leu Val Asp
                165                 170                 175

Tyr Thr Pro Thr Asp Gln Asp Leu Leu Arg Cys Arg Val Leu Thr Ser
            180                 185                 190

Gly Ile Phe Glu Thr Arg Phe Gln Val Asp Lys Val Asn Phe His Met
        195                 200                 205

Phe Asp Val Gly Gly Gln Arg Asp Glu Arg Arg Lys Trp Ile Gln Cys
    210                 215                 220

Phe Asn Asp Val Thr Ala Ile Ile Tyr Val Ala Ala Cys Ser Ser Tyr
225                 230                 235                 240

Asn Met Val Ile Arg Glu Asp Asn Thr Asn Arg Leu Arg Glu Ser
                245                 250                 255

Leu Asp Leu Phe Glu Ser Ile Trp Asn Asn Arg Trp Leu Arg Thr Ile
            260                 265                 270

Ser Ile Ile Leu Phe Leu Asn Lys Gln Asp Met Leu Ala Glu Lys Val
        275                 280                 285

Leu Ala Gly Lys Ser Lys Ile Glu Asp Tyr Phe Pro Glu Tyr Ala Asn
    290                 295                 300

Tyr Thr Val Pro Glu Asp Ala Thr Pro Asp Ala Gly Glu Asp Pro Lys
305                 310                 315                 320

Val Thr Arg Ala Lys Phe Phe Ile Arg Asp Leu Phe Leu Arg Ile Ser
                325                 330                 335

Thr Ala Thr Gly Asp Gly Lys His Tyr Cys Tyr Pro His Phe Thr Cys
```

```
            340                 345                 350
Ala Val Asp Thr Glu Asn Ile Arg Arg Val Phe Asn Asp Cys Arg Asp
            355                 360                 365

Ile Ile Gln Arg Met His Leu Lys Gln Tyr Glu Leu Leu
        370                 375                 380

<210> SEQ ID NO 3
<211> LENGTH: 354
<212> TYPE: PRT
<213> ORGANISM: Artificial
<220> FEATURE:
<223> OTHER INFORMATION: Chemically synthesized

<400> SEQUENCE: 3

Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Ala Gly Tyr Ser Glu Glu
    50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
        115                 120                 125

Arg Leu Trp Lys Asp Ser Gly Val Gln Ala Cys Phe Asn Arg Ser Arg
    130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
        195                 200                 205

Lys Lys Trp Ile His Cys Phe Glu Gly Val Thr Ala Ile Ile Phe Cys
    210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Phe Thr Asp Thr Ser Ile Ile Leu Phe Leu Asn Lys Lys Asp
            260                 265                 270

Leu Phe Glu Glu Lys Ile Lys Lys Ser Pro Leu Thr Ile Cys Tyr Pro
        275                 280                 285

Glu Tyr Ala Gly Ser Asn Thr Tyr Glu Glu Ala Ala Tyr Ile Gln
    290                 295                 300

Cys Gln Phe Glu Asp Leu Asn Lys Arg Lys Asp Thr Lys Glu Ile Tyr
305                 310                 315                 320

Thr His Phe Thr Cys Ala Thr Asp Thr Lys Asn Val Gln Phe Val Phe
                325                 330                 335
```

```
Asp Ala Val Thr Asp Val Ile Ile Lys Asn Asn Leu Lys Gln Tyr Glu
            340                 345                 350
Leu Leu
```

<210> SEQ ID NO 4
<211> LENGTH: 354
<212> TYPE: PRT
<213> ORGANISM: Artificial
<220> FEATURE:
<223> OTHER INFORMATION: Chemically synthesized

<400> SEQUENCE: 4

```
Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Ala Gly Tyr Ser Glu Glu
    50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
        115                 120                 125

Arg Leu Trp Lys Asp Ser Gly Val Gln Ala Cys Phe Asn Arg Ser Arg
    130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
        195                 200                 205

Lys Lys Trp Ile His Cys Phe Glu Gly Val Thr Ala Ile Ile Phe Cys
    210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Phe Thr Asp Thr Ser Ile Ile Leu Phe Leu Asn Lys Lys Asp
            260                 265                 270

Leu Phe Glu Glu Lys Ile Lys Lys Ser Pro Leu Thr Ile Cys Tyr Pro
        275                 280                 285

Glu Tyr Ala Gly Ser Asn Thr Tyr Glu Glu Ala Ala Ala Tyr Ile Gln
    290                 295                 300

Cys Gln Phe Glu Asp Leu Asn Lys Arg Lys Asp Thr Lys Glu Ile Tyr
305                 310                 315                 320

Thr His Phe Thr Cys Ala Thr Asp Thr Lys Asn Val Gln Phe Val Phe
                325                 330                 335

Asp Ala Val Thr Asp Ile Ile Gln Arg Met His Leu Lys Gln Tyr Glu
```

Leu Leu

<210> SEQ ID NO 5
<211> LENGTH: 354
<212> TYPE: PRT
<213> ORGANISM: Artificial
<220> FEATURE:
<223> OTHER INFORMATION: Chemically synthesized

<400> SEQUENCE: 5

Met Gly Cys Thr Leu Ser Ala Glu Asp Lys Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Gly Ala Gly Glu Ser Gly Lys Ser Thr
                35                  40                  45

Ile Val Lys Gln Met Lys Ile Ile His Glu Ala Gly Tyr Ser Glu Glu
                50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                    85                  90                  95

Asp Ser Ala Arg Ala Asp Asp Ala Arg Gln Leu Phe Val Leu Ala Gly
                100                 105                 110

Ala Ala Glu Glu Gly Phe Met Thr Ala Glu Leu Ala Gly Val Ile Lys
            115                 120                 125

Arg Leu Trp Lys Asp Ser Gly Val Gln Ala Cys Phe Asn Arg Ser Arg
130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
                195                 200                 205

Lys Lys Trp Ile His Cys Phe Glu Gly Val Thr Ala Ile Ile Phe Cys
        210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Phe Thr Asp Thr Ser Ile Ile Leu Phe Leu Asn Lys Lys Asp
            260                 265                 270

Leu Phe Glu Glu Lys Ile Lys Lys Ser Pro Leu Thr Ile Cys Tyr Pro
        275                 280                 285

Glu Tyr Ala Gly Ser Asn Thr Tyr Glu Glu Ala Ala Ala Tyr Ile Gln
    290                 295                 300

Cys Gln Phe Glu Asp Leu Asn Lys Arg Lys Asp Thr Lys Glu Ile Tyr
305                 310                 315                 320

Thr His Phe Thr Cys Ala Val Asp Thr Glu Asn Ile Arg Arg Val Phe
                325                 330                 335

Asn Asp Cys Arg Asp Ile Ile Gln Arg Met His Leu Lys Gln Tyr Glu
            340                 345                 350

Leu Leu

<210> SEQ ID NO 6
<211> LENGTH: 356
<212> TYPE: PRT
<213> ORGANISM: Artificial
<220> FEATURE:
<223> OTHER INFORMATION: Chemically synthesized

<400> SEQUENCE: 6

Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Ala Gly Tyr Ser Glu Glu
    50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
        115                 120                 125

Arg Leu Trp Lys Asp Ser Gly Val Gln Ala Cys Phe Asn Arg Ser Arg
    130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
        195                 200                 205

Lys Lys Trp Ile His Cys Phe Glu Gly Val Thr Ala Ile Ile Phe Cys
    210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Phe Thr Asp Thr Ser Ile Ile Leu Phe Leu Asn Lys Lys Asp
            260                 265                 270

Leu Phe Glu Glu Lys Ile Lys Lys Ser Pro Leu Thr Ile Cys Tyr Pro
        275                 280                 285

Glu Tyr Ala Gly Ser Asn Thr Tyr Glu Glu Ala Ala Ala Tyr Ile Gln
    290                 295                 300

Cys Gln Phe Glu Asp Leu Asn Thr Ala Thr Gly Asp Gly Lys His Tyr
305                 310                 315                 320

Cys Tyr Pro His Phe Thr Cys Ala Val Asp Thr Glu Asn Ile Arg Arg
                325                 330                 335

Val Phe Asn Asp Cys Arg Asp Ile Ile Gln Arg Met His Leu Lys Gln
            340                 345                 350

Tyr Glu Leu Leu
        355

<210> SEQ ID NO 7
<211> LENGTH: 371
<212> TYPE: PRT
<213> ORGANISM: Artificial
<220> FEATURE:
<223> OTHER INFORMATION: Chemically synthesized

<400> SEQUENCE: 7

| | | | | | | | | | | | | | | |
|---|---|---|---|---|---|---|---|---|---|---|---|---|---|---|
| Met | Gly | Cys | Thr | Leu | Ser | Ala | Glu | Asp | Lys | Ala | Val | Glu | Arg | Ser |
| 1 | | | | 5 | | | | | 10 | | | | | 15 |
| Lys | Met | Ile | Asp | Arg | Asn | Leu | Arg | Glu | Asp | Gly | Glu | Lys | Ala | Arg |
| | | | 20 | | | | | 25 | | | | | 30 | |
| Glu | Val | Lys | Leu | Leu | Leu | Leu | Gly | Ala | Gly | Glu | Ser | Gly | Lys | Ser | Thr |
| | | 35 | | | | | | 40 | | | | | 45 | |
| Ile | Val | Lys | Gln | Met | Lys | Ile | Ile | His | Glu | Ala | Gly | Tyr | Ser | Glu | Glu |
| | 50 | | | | | 55 | | | | | 60 | | | | |
| Glu | Cys | Lys | Gln | Tyr | Lys | Ala | Val | Val | Tyr | Ser | Asn | Thr | Ile | Gln | Ser |
| 65 | | | | | 70 | | | | | 75 | | | | | 80 |
| Ile | Ile | Ala | Ile | Ile | Arg | Ala | Met | Gly | Arg | Leu | Lys | Ile | Asp | Phe | Gly |
| | | | | 85 | | | | | 90 | | | | | 95 | |
| Asp | Ser | Ala | Arg | Ala | Asp | Asp | Ala | Arg | Gln | Leu | Phe | Val | Leu | Ala | Gly |
| | | | | 100 | | | | | 105 | | | | | 110 | |
| Ala | Ala | Glu | Glu | Gly | Phe | Met | Thr | Ala | Glu | Leu | Ala | Gly | Val | Ile | Lys |
| | | | 115 | | | | | 120 | | | | | 125 | | |
| Arg | Leu | Trp | Lys | Asp | Ser | Gly | Val | Gln | Ala | Cys | Phe | Asn | Arg | Ser | Arg |
| | 130 | | | | | 135 | | | | | 140 | | | | |
| Glu | Tyr | Gln | Leu | Asn | Asp | Ser | Ala | Ala | Tyr | Tyr | Leu | Asn | Asp | Leu | Asp |
| 145 | | | | | 150 | | | | | 155 | | | | | 160 |
| Arg | Ile | Ala | Gln | Pro | Asn | Tyr | Ile | Pro | Thr | Gln | Gln | Asp | Val | Leu | Arg |
| | | | | 165 | | | | | 170 | | | | | 175 | |
| Thr | Arg | Val | Lys | Thr | Thr | Gly | Ile | Val | Glu | Thr | His | Phe | Thr | Phe | Lys |
| | | | 180 | | | | | 185 | | | | | 190 | | |
| Asp | Leu | His | Phe | Lys | Met | Phe | Asp | Val | Gly | Gly | Gln | Arg | Ser | Glu | Arg |
| | 195 | | | | | 200 | | | | | 205 | | | | |
| Lys | Lys | Trp | Ile | His | Cys | Phe | Glu | Gly | Val | Thr | Ala | Ile | Ile | Phe | Cys |
| 210 | | | | | 215 | | | | | 220 | | | | | |
| Val | Ala | Leu | Ser | Asp | Tyr | Asp | Leu | Val | Leu | Ala | Glu | Asp | Glu | Glu | Met |
| 225 | | | | | 230 | | | | | 235 | | | | | 240 |
| Asn | Arg | Met | His | Glu | Ser | Met | Lys | Leu | Phe | Asp | Ser | Ile | Cys | Asn | Asn |
| | | | | 245 | | | | | 250 | | | | | 255 | |
| Lys | Trp | Phe | Thr | Asp | Thr | Ser | Ile | Ile | Leu | Phe | Leu | Asn | Lys | Lys | Asp |
| | | | 260 | | | | | 265 | | | | | 270 | | |
| Leu | Phe | Glu | Glu | Lys | Val | Leu | Ala | Gly | Lys | Ser | Lys | Ile | Glu | Asp | Tyr |
| | | 275 | | | | | 280 | | | | | 285 | | | |
| Phe | Pro | Glu | Tyr | Ala | Asn | Tyr | Thr | Val | Pro | Glu | Asp | Ala | Thr | Pro | Asp |
| | 290 | | | | | 295 | | | | | 300 | | | | |
| Ala | Gly | Glu | Asp | Pro | Lys | Val | Thr | Arg | Ala | Lys | Phe | Phe | Ile | Arg | Asp |
| 305 | | | | | 310 | | | | | 315 | | | | | 320 |
| Leu | Phe | Leu | Arg | Ile | Ser | Thr | Ala | Thr | Gly | Asp | Gly | Lys | His | Tyr | Cys |
| | | | | 325 | | | | | 330 | | | | | 335 | |
| Tyr | Pro | His | Phe | Thr | Cys | Ala | Val | Asp | Thr | Glu | Asn | Ile | Arg | Arg | Val |
| | | | 340 | | | | | 345 | | | | | 350 | | |
| Phe | Asn | Asp | Cys | Arg | Asp | Ile | Ile | Gln | Arg | Met | His | Leu | Lys | Gln | Tyr |
| | | 355 | | | | | 360 | | | | | 365 | | | |

Glu Leu Leu
    370

<210> SEQ ID NO 8
<211> LENGTH: 371
<212> TYPE: PRT
<213> ORGANISM: Artificial
<220> FEATURE:
<223> OTHER INFORMATION: Chemically synthesized

<400> SEQUENCE: 8

Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Ala Gly Tyr Ser Glu Glu
    50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
        115                 120                 125

Arg Leu Trp Lys Asp Ser Gly Val Gln Ala Cys Phe Asn Arg Ser Arg
130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
        195                 200                 205

Lys Lys Trp Ile His Cys Phe Glu Gly Val Thr Ala Ile Ile Phe Cys
    210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Leu Arg Thr Ile Ser Ile Ile Leu Phe Leu Asn Lys Gln Asp
            260                 265                 270

Met Leu Ala Glu Lys Val Leu Ala Gly Lys Ser Lys Ile Glu Asp Tyr
        275                 280                 285

Phe Pro Glu Tyr Ala Asn Tyr Thr Val Pro Glu Asp Ala Thr Pro Asp
    290                 295                 300

Ala Gly Glu Asp Pro Lys Val Thr Arg Ala Lys Phe Phe Ile Arg Asp
305                 310                 315                 320

Leu Phe Leu Arg Ile Ser Thr Ala Thr Gly Asp Gly Lys His Tyr Cys
                325                 330                 335

Tyr Pro His Phe Thr Cys Ala Val Asp Thr Glu Asn Ile Arg Arg Val
            340                 345                 350

Phe Asn Asp Cys Arg Asp Ile Ile Gln Arg Met His Leu Lys Gln Tyr

Glu Leu Leu
    370

<210> SEQ ID NO 9
<211> LENGTH: 371
<212> TYPE: PRT
<213> ORGANISM: Artificial
<220> FEATURE:
<223> OTHER INFORMATION: Chemically synthesized

<400> SEQUENCE: 9

Met Gly Cys Thr Leu Ser Ala Glu Asp Lys Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Gly Ala Gly Glu Ser Gly Lys Ser Thr
            35                  40                  45

Ile Val Lys Gln Met Lys Ile Ile His Glu Ala Gly Tyr Ser Glu Glu
        50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
        115                 120                 125

Arg Leu Trp Lys Asp Ser Gly Val Gln Ala Cys Phe Asn Arg Ser Arg
130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
        195                 200                 205

Lys Lys Trp Ile His Cys Phe Asn Asp Val Thr Ala Ile Ile Tyr Val
    210                 215                 220

Ala Ala Cys Ser Ser Tyr Asn Met Val Ile Arg Glu Asp Asn Asn Thr
225                 230                 235                 240

Asn Arg Leu Arg Glu Ser Leu Asp Leu Phe Glu Ser Ile Trp Asn Asn
                245                 250                 255

Arg Trp Leu Arg Thr Ile Ser Ile Ile Leu Phe Leu Asn Lys Gln Asp
            260                 265                 270

Met Leu Ala Glu Lys Val Leu Ala Gly Lys Ser Lys Ile Glu Asp Tyr
        275                 280                 285

Phe Pro Glu Tyr Ala Asn Tyr Thr Val Pro Glu Asp Ala Thr Pro Asp
    290                 295                 300

Ala Gly Glu Asp Pro Lys Val Thr Arg Ala Lys Phe Phe Ile Arg Asp
305                 310                 315                 320

Leu Phe Leu Arg Ile Ser Thr Ala Thr Gly Asp Gly Lys His Tyr Cys
                325                 330                 335

Tyr Pro His Phe Thr Cys Ala Val Asp Thr Glu Asn Ile Arg Arg Val
            340                 345                 350

-continued

Phe Asn Asp Cys Arg Asp Ile Ile Gln Arg Met His Leu Lys Gln Tyr
        355                 360                 365

Glu Leu Leu
    370

<210> SEQ ID NO 10
<211> LENGTH: 371
<212> TYPE: PRT
<213> ORGANISM: Artificial
<220> FEATURE:
<223> OTHER INFORMATION: Chemically synthesized

<400> SEQUENCE: 10

Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Ala Gly Tyr Ser Glu Glu
    50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
        115                 120                 125

Arg Leu Trp Lys Asp Ser Gly Val Gln Ala Cys Phe Asn Arg Ser Arg
    130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Cys Arg Val Leu Thr Ser Gly Ile Phe Glu Thr Arg Phe Gln Val Asp
            180                 185                 190

Lys Val Asn Phe His Met Phe Asp Val Gly Gly Gln Arg Asp Glu Arg
        195                 200                 205

Arg Lys Trp Ile Gln Cys Phe Asn Asp Val Thr Ala Ile Ile Tyr Val
    210                 215                 220

Ala Ala Cys Ser Ser Tyr Asn Met Val Ile Arg Glu Asp Asn Asn Thr
225                 230                 235                 240

Asn Arg Leu Arg Glu Ser Leu Asp Leu Phe Glu Ser Ile Trp Asn Asn
                245                 250                 255

Arg Trp Leu Arg Thr Ile Ser Ile Ile Leu Phe Leu Asn Lys Gln Asp
            260                 265                 270

Met Leu Ala Glu Lys Val Leu Ala Gly Lys Ser Lys Ile Glu Asp Tyr
        275                 280                 285

Phe Pro Glu Tyr Ala Asn Tyr Thr Val Pro Glu Asp Ala Thr Pro Asp
    290                 295                 300

Ala Gly Glu Asp Pro Lys Val Thr Arg Ala Lys Phe Phe Ile Arg Asp
305                 310                 315                 320

Leu Phe Leu Arg Ile Ser Thr Ala Thr Gly Asp Gly Lys His Tyr Cys
                325                 330                 335

```
Tyr Pro His Phe Thr Cys Ala Val Asp Thr Glu Asn Ile Arg Arg Val
                340                 345                 350

Phe Asn Asp Cys Arg Asp Ile Ile Gln Arg Met His Leu Lys Gln Tyr
            355                 360                 365

Glu Leu Leu
    370

<210> SEQ ID NO 11
<211> LENGTH: 354
<212> TYPE: PRT
<213> ORGANISM: Artificial
<220> FEATURE:
<223> OTHER INFORMATION: Chemically synthesized

<400> SEQUENCE: 11

Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Ala Gly Tyr Ser Glu Glu
    50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
        115                 120                 125

Arg Leu Trp Lys Asp Ser Gly Val Gln Ala Cys Phe Asn Arg Ser Arg
130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
        195                 200                 205

Lys Lys Trp Ile His Cys Phe Glu Gly Val Thr Ala Ile Ile Phe Cys
210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Leu Arg Thr Ile Ser Ile Ile Leu Phe Leu Asn Lys Lys Asp
            260                 265                 270

Leu Phe Glu Glu Lys Ile Lys Lys Ser Pro Leu Thr Ile Cys Tyr Pro
        275                 280                 285

Glu Tyr Ala Gly Ser Asn Thr Tyr Glu Glu Ala Ala Ala Tyr Ile Gln
        290                 295                 300

Cys Gln Phe Glu Asp Leu Asn Lys Arg Lys Asp Thr Lys Glu Ile Tyr
305                 310                 315                 320

Thr His Phe Thr Cys Ala Thr Asp Thr Lys Asn Val Gln Phe Val Phe
```

Asp Ala Val Thr Asp Val Ile Ile Lys Asn Asn Leu Lys Asp Cys Gly
            325                 330                 335

Leu Phe
            340                 345                 350

<210> SEQ ID NO 12
<211> LENGTH: 354
<212> TYPE: PRT
<213> ORGANISM: Artificial
<220> FEATURE:
<223> OTHER INFORMATION: Chemically synthesized

<400> SEQUENCE: 12

Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Ala Gly Tyr Ser Glu Glu
    50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
        115                 120                 125

Arg Leu Trp Lys Asp Ser Gly Val Gln Ala Cys Phe Asn Arg Ser Arg
    130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
        195                 200                 205

Lys Lys Trp Ile His Cys Phe Glu Gly Val Thr Ala Ile Ile Phe Cys
    210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Leu Arg Thr Ile Ser Ile Ile Leu Phe Leu Asn Lys Lys Asp
            260                 265                 270

Leu Phe Glu Glu Lys Ile Lys Lys Ser Pro Leu Thr Ile Cys Tyr Pro
        275                 280                 285

Glu Tyr Ala Gly Ser Asn Thr Tyr Glu Glu Ala Ala Ala Tyr Ile Gln
    290                 295                 300

Cys Gln Phe Glu Asp Leu Asn Lys Arg Lys Asp Thr Lys Glu Ile Tyr
305                 310                 315                 320

Thr His Phe Thr Cys Ala Thr Asp Thr Lys Asn Val Gln Phe Val Phe
                325                 330                 335

Asp Ala Val Thr Asp Ile Ile Gln Arg Met His Leu Lys Gln Tyr Glu
            340                 345                 350

Leu Leu

<210> SEQ ID NO 13
<211> LENGTH: 356
<212> TYPE: PRT
<213> ORGANISM: Artificial
<220> FEATURE:
<223> OTHER INFORMATION: Chemically synthesized

<400> SEQUENCE: 13

Met Gly Cys Thr Leu Ser Ala Glu Asp Lys Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
            35                  40                  45

Ile Val Lys Gln Met Lys Ile Ile His Glu Ala Gly Tyr Ser Glu Glu
50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
            115                 120                 125

Arg Leu Trp Lys Asp Ser Gly Val Gln Ala Cys Phe Asn Arg Ser Arg
130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
            195                 200                 205

Lys Lys Trp Ile His Cys Phe Glu Gly Val Thr Ala Ile Ile Phe Cys
210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Phe Thr Asp Thr Ser Ile Ile Leu Phe Leu Asn Lys Lys Asp
            260                 265                 270

Leu Phe Glu Glu Lys Ile Lys Lys Ser Pro Leu Thr Ile Cys Tyr Pro
            275                 280                 285

Glu Tyr Ala Gly Ser Asn Thr Tyr Glu Glu Ala Ala Tyr Ile Gln
            290                 295                 300

Cys Gln Phe Glu Asp Leu Asn Thr Ala Thr Gly Asp Gly Lys His Tyr
305                 310                 315                 320

Cys Tyr Thr His Phe Thr Cys Ala Thr Asp Thr Lys Asn Val Gln Phe
                325                 330                 335

Val Phe Asp Ala Val Thr Asp Val Ile Ile Lys Asn Asn Leu Lys Asp
            340                 345                 350

```
Cys Gly Leu Phe
        355

<210> SEQ ID NO 14
<211> LENGTH: 356
<212> TYPE: PRT
<213> ORGANISM: Artificial
<220> FEATURE:
<223> OTHER INFORMATION: Chemically synthesized

<400> SEQUENCE: 14

Met Gly Cys Thr Leu Ser Ala Glu Asp Lys Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
            35                  40                  45

Ile Val Lys Gln Met Lys Ile Ile His Glu Ala Gly Tyr Ser Glu Glu
            50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
            115                 120                 125

Arg Leu Trp Lys Asp Ser Gly Val Gln Ala Cys Phe Asn Arg Ser Arg
            130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
            195                 200                 205

Lys Lys Trp Ile His Cys Phe Glu Gly Val Thr Ala Ile Ile Phe Cys
            210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Leu Arg Thr Ile Ser Ile Ile Leu Phe Leu Asn Lys Lys Asp
            260                 265                 270

Leu Phe Glu Glu Lys Ile Lys Lys Ser Pro Leu Thr Ile Cys Tyr Pro
            275                 280                 285

Glu Tyr Ala Gly Ser Asn Thr Tyr Glu Glu Ala Ala Ala Tyr Ile Gln
            290                 295                 300

Cys Gln Phe Glu Asp Leu Asn Thr Ala Thr Gly Asp Gly Lys His Tyr
305                 310                 315                 320

Cys Tyr Thr His Phe Thr Cys Ala Thr Asp Thr Lys Asn Val Gln Phe
                325                 330                 335

Val Phe Asp Ala Val Thr Asp Val Ile Ile Lys Asn Asn Leu Lys Asp
            340                 345                 350
```

Cys Gly Leu Phe
        355

<210> SEQ ID NO 15
<211> LENGTH: 356
<212> TYPE: PRT
<213> ORGANISM: Artificial
<220> FEATURE:
<223> OTHER INFORMATION: Chemically synthesized

<400> SEQUENCE: 15

Met Gly Cys Thr Leu Ser Ala Glu Asp Lys Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Ala Gly Tyr Ser Glu Glu
    50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
        115                 120                 125

Arg Leu Trp Lys Asp Ser Gly Val Gln Ala Cys Phe Asn Arg Ser Arg
    130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
        195                 200                 205

Lys Lys Trp Ile His Cys Phe Glu Gly Val Thr Ala Ile Ile Phe Cys
    210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Phe Thr Asp Thr Ser Ile Ile Leu Phe Leu Asn Lys Lys Asp
            260                 265                 270

Leu Phe Glu Glu Lys Ile Lys Lys Ser Pro Leu Thr Ile Cys Tyr Pro
        275                 280                 285

Glu Tyr Ala Gly Ser Asn Thr Tyr Glu Glu Ala Ala Ala Tyr Ile Gln
    290                 295                 300

Cys Gln Phe Glu Asp Leu Asn Thr Ala Thr Gly Asp Gly Lys His Tyr
305                 310                 315                 320

Cys Tyr Thr His Phe Thr Cys Ala Thr Asp Thr Lys Asn Val Gln Phe
                325                 330                 335

Val Phe Asp Ala Val Thr Asp Ile Ile Gln Arg Met His Leu Lys Gln
            340                 345                 350

Tyr Glu Leu Leu

<210> SEQ ID NO 16
<211> LENGTH: 356
<212> TYPE: PRT
<213> ORGANISM: Artificial
<220> FEATURE:
<223> OTHER INFORMATION: Chemically synthesized

<400> SEQUENCE: 16

```
Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Ala Gly Tyr Ser Glu Glu
    50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
        115                 120                 125

Arg Leu Trp Lys Asp Ser Gly Val Gln Ala Cys Phe Asn Arg Ser Arg
130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
        195                 200                 205

Lys Lys Trp Ile His Cys Phe Glu Gly Val Thr Ala Ile Ile Phe Cys
210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Leu Arg Thr Ile Ser Ile Ile Leu Phe Leu Asn Lys Lys Asp
            260                 265                 270

Leu Phe Glu Glu Lys Ile Lys Lys Ser Pro Leu Thr Ile Cys Tyr Pro
        275                 280                 285

Glu Tyr Ala Gly Ser Asn Thr Tyr Glu Glu Ala Ala Ala Tyr Ile Gln
290                 295                 300

Cys Gln Phe Glu Asp Leu Asn Thr Ala Thr Gly Asp Gly Lys His Tyr
305                 310                 315                 320

Cys Tyr Thr His Phe Thr Cys Ala Thr Asp Thr Lys Asn Val Gln Phe
                325                 330                 335

Val Phe Asp Ala Val Thr Asp Ile Ile Gln Arg Met His Leu Lys Gln
            340                 345                 350

Tyr Glu Leu Leu
        355
```

<210> SEQ ID NO 17
<211> LENGTH: 19
<212> TYPE: DNA
<213> ORGANISM: Artificial
<220> FEATURE:
<223> OTHER INFORMATION: PRIMER FOR PREPARING BETA-1 ADRENERIGIC RECEPTOR

<400> SEQUENCE: 17
atgggcgcgg gggcgctcg                                               19

<210> SEQ ID NO 18
<211> LENGTH: 28
<212> TYPE: DNA
<213> ORGANISM: Artificial
<220> FEATURE:
<223> OTHER INFORMATION: PRIMER FOR PREPARING BETA-1 ADRENERIGIC RECEPTOR

<400> SEQUENCE: 18
gaagacgaag aggcgatccg gcaccagg                                     28

<210> SEQ ID NO 19
<211> LENGTH: 28
<212> TYPE: DNA
<213> ORGANISM: Artificial
<220> FEATURE:
<223> OTHER INFORMATION: PRIMER FOR PREPARING BETA-1 ADRENERIGIC RECEPTOR

<400> SEQUENCE: 19
cactgggcat catcatgggt gtgttcac                                     28

<210> SEQ ID NO 20
<211> LENGTH: 27
<212> TYPE: DNA
<213> ORGANISM: Artificial
<220> FEATURE:
<223> OTHER INFORMATION: PRIMER FOR PREPARING BETA-1 ADRENERIGIC RECEPTOR

<400> SEQUENCE: 20
ctacaccttg gactcggagg agaagcc                                      27

<210> SEQ ID NO 21
<211> LENGTH: 32
<212> TYPE: DNA
<213> ORGANISM: Artificial
<220> FEATURE:
<223> OTHER INFORMATION: PRIMER FOR PREPARING BETA-1 ADRENERIGIC RECEPTOR

<400> SEQUENCE: 21
ttcgaattcg ccaccatggg cgcggggcg ct                                 32

<210> SEQ ID NO 22
<211> LENGTH: 29
<212> TYPE: DNA
<213> ORGANISM: Artificial
<220> FEATURE:
<223> OTHER INFORMATION: PRIMER FOR PREPARING BETA-1 ADRENERIGIC RECEPTOR

<400> SEQUENCE: 22
gaagtcgacc tacaccttgg actcggagg                                    29

```
<210> SEQ ID NO 23
<211> LENGTH: 28
<212> TYPE: DNA
<213> ORGANISM: Artificial
<220> FEATURE:
<223> OTHER INFORMATION: PRIMER FOR PREPARING Kir3.1

<400> SEQUENCE: 23
gcgcctccgc ttcgtgtttg aatctggc                                           28

<210> SEQ ID NO 24
<211> LENGTH: 28
<212> TYPE: DNA
<213> ORGANISM: Artificial
<220> FEATURE:
<223> OTHER INFORMATION: PRIMER FOR PREPARING Kir3.1

<400> SEQUENCE: 24
gccttccagg atgacgacaa cctcgaac                                           28

<210> SEQ ID NO 25
<211> LENGTH: 26
<212> TYPE: DNA
<213> ORGANISM: Artificial
<220> FEATURE:
<223> OTHER INFORMATION: PRIMER FOR PREPARING Kir3.1

<400> SEQUENCE: 25
ccgggtgggc aacctgcgca acagcc                                             26

<210> SEQ ID NO 26
<211> LENGTH: 24
<212> TYPE: DNA
<213> ORGANISM: Artificial
<220> FEATURE:
<223> OTHER INFORMATION: PRIMER FOR PREPARING Kir3.1

<400> SEQUENCE: 26
gccaggctag gatagacctc tcag                                               24

<210> SEQ ID NO 27
<211> LENGTH: 30
<212> TYPE: DNA
<213> ORGANISM: Artificial
<220> FEATURE:
<223> OTHER INFORMATION: PRIMER FOR PREPARING Kir3.1

<400> SEQUENCE: 27
gcgctagcgc caccatgtct gcactccgaa                                         30

<210> SEQ ID NO 28
<211> LENGTH: 30
<212> TYPE: DNA
<213> ORGANISM: Artificial
<220> FEATURE:
<223> OTHER INFORMATION: PRIMER FOR PREPARING Kir3.1

<400> SEQUENCE: 28
ggcatcgatc acgtggcaaa ttgtgagagg                                         30

<210> SEQ ID NO 29
<211> LENGTH: 30
<212> TYPE: DNA
<213> ORGANISM: Artificial
<220> FEATURE:
<223> OTHER INFORMATION: PRIMER FOR PREPARING Kir3.1

<400> SEQUENCE: 29
```

-continued gtgatcgatg ccaaaagccc cttctatgac                    30

<210> SEQ ID NO 30
<211> LENGTH: 29
<212> TYPE: DNA
<213> ORGANISM: Artificial
<220> FEATURE:
<223> OTHER INFORMATION: PRIMER FOR PREPARING Kir3.1

<400> SEQUENCE: 30
gcgcggccgc ctatgtgaaa cggtcagag                     29

<210> SEQ ID NO 31
<211> LENGTH: 30
<212> TYPE: DNA
<213> ORGANISM: Artificial
<220> FEATURE:
<223> OTHER INFORMATION: PRIMER FOR PREPARING Kir3.1

<400> SEQUENCE: 31
ctctgccttc ctcttctcca tcgagaccga                    30

<210> SEQ ID NO 32
<211> LENGTH: 29
<212> TYPE: DNA
<213> ORGANISM: Artificial
<220> FEATURE:
<223> OTHER INFORMATION: PRIMER FOR PREPARING Kir3.1

<400> SEQUENCE: 32
ggtctcgatg gagaagagga aggcagagg                     29

<210> SEQ ID NO 33
<211> LENGTH: 29
<212> TYPE: DNA
<213> ORGANISM: Artificial
<220> FEATURE:
<223> OTHER INFORMATION: PRIMER FOR PREPARING G alpha olf

<400> SEQUENCE: 33
atggggtgtt tgggcaacag cagcaagac                     29

<210> SEQ ID NO 34
<211> LENGTH: 26
<212> TYPE: DNA
<213> ORGANISM: Artificial
<220> FEATURE:
<223> OTHER INFORMATION: PRIMER FOR PREPARING G alpha olf

<400> SEQUENCE: 34
ggaggaggag gagggtagg tttagg                         26

<210> SEQ ID NO 35
<211> LENGTH: 35
<212> TYPE: DNA
<213> ORGANISM: Artificial
<220> FEATURE:
<223> OTHER INFORMATION: PRIMER FOR PREPARING G alpha olf

<400> SEQUENCE: 35
aatgaattcg ccaccatggg gtgtttgggc aacag              35

<210> SEQ ID NO 36
<211> LENGTH: 33
<212> TYPE: DNA
<213> ORGANISM: Artificial

```
<220> FEATURE:
<223> OTHER INFORMATION: PRIMER FOR PREPARING G alpha olf

<400> SEQUENCE: 36
aatgtcgact cacaagagtt cgtactgctt gag                          33

<210> SEQ ID NO 37
<211> LENGTH: 25
<212> TYPE: DNA
<213> ORGANISM: Artificial
<220> FEATURE:
<223> OTHER INFORMATION: PRIMER FOR PREPARING G alpha i

<400> SEQUENCE: 37
cggcagcgtg cggactagca gacct                                   25

<210> SEQ ID NO 38
<211> LENGTH: 28
<212> TYPE: DNA
<213> ORGANISM: Artificial
<220> FEATURE:
<223> OTHER INFORMATION: PRIMER FOR PREPARING G alpha i

<400> SEQUENCE: 38
gaacagcttc atgctctcgt gcatacgg                                28

<210> SEQ ID NO 39
<211> LENGTH: 28
<212> TYPE: DNA
<213> ORGANISM: Artificial
<220> FEATURE:
<223> OTHER INFORMATION: PRIMER FOR PREPARING G alpha i

<400> SEQUENCE: 39
gctgaacgat tcggcagcgt actatctg                                28

<210> SEQ ID NO 40
<211> LENGTH: 28
<212> TYPE: DNA
<213> ORGANISM: Artificial
<220> FEATURE:
<223> OTHER INFORMATION: PRIMER FOR PREPARING G alpha i

<400> SEQUENCE: 40
ggtcagaact ctggtcaggt ccaggatg                                28

<210> SEQ ID NO 41
<211> LENGTH: 35
<212> TYPE: DNA
<213> ORGANISM: Artificial
<220> FEATURE:
<223> OTHER INFORMATION: PRIMER FOR PREPARING G alpha i

<400> SEQUENCE: 41
gcgctcgagc caccatgggc tgcacattga gcgct                        35

<210> SEQ ID NO 42
<211> LENGTH: 23
<212> TYPE: DNA
<213> ORGANISM: Artificial
<220> FEATURE:
<223> OTHER INFORMATION: PRIMER FOR PREPARING G alpha i

<400> SEQUENCE: 42
aagtggatcc actgctttga agg                                     23
```

```
<210> SEQ ID NO 43
<211> LENGTH: 22
<212> TYPE: DNA
<213> ORGANISM: Artificial
<220> FEATURE:
<223> OTHER INFORMATION: PRIMER FOR PREPARING G alpha i

<400> SEQUENCE: 43
agtggatcca cttcttccgc tc                                              22

<210> SEQ ID NO 44
<211> LENGTH: 76
<212> TYPE: DNA
<213> ORGANISM: Artificial
<220> FEATURE:
<223> OTHER INFORMATION: PRIMER FOR PREPARING G alpha i

<400> SEQUENCE: 44
cgcgaattct tagaagagac caatgtcttt taggttattc tttatgatga cgtctgttac     60
agcatcgaac acgaac                                                     76

<210> SEQ ID NO 45
<211> LENGTH: 76
<212> TYPE: DNA
<213> ORGANISM: Artificial
<220> FEATURE:
<223> OTHER INFORMATION: PRIMER FOR PREPARING Gi/olf5

<400> SEQUENCE: 45
cgcgaattct tagagcagct cgtattgttt taggttattc tttatgatga cgtctgttac     60
agcatcgaac acgaac                                                     76

<210> SEQ ID NO 46
<211> LENGTH: 76
<212> TYPE: DNA
<213> ORGANISM: Artificial
<220> FEATURE:
<223> OTHER INFORMATION: PRIMER FOR PREPARING Gi/s13

<400> SEQUENCE: 46
cgcgaattct tagagcagct cgtattggcg gagatgcatg cgctggatga tgtctgttac     60
agcatcgaac acgaac                                                     76

<210> SEQ ID NO 47
<211> LENGTH: 76
<212> TYPE: DNA
<213> ORGANISM: Artificial
<220> FEATURE:
<223> OTHER INFORMATION: PRIMER FOR PREPARING Gi/olf13

<400> SEQUENCE: 47
cgcgaattct tagagcagct cgtattgctt gagatgcatg cgctggatga tgtctgttac     60
agcatcgaac acgaac                                                     76

<210> SEQ ID NO 48
<211> LENGTH: 35
<212> TYPE: DNA
<213> ORGANISM: Artificial
<220> FEATURE:
<223> OTHER INFORMATION: PRIMER FOR PREPARING Gi/olf28

<400> SEQUENCE: 48
cctgaattct gccaccatgg gctgcacatt gagcg                                35
```

<210> SEQ ID NO 49
<211> LENGTH: 35
<212> TYPE: DNA
<213> ORGANISM: Artificial
<220> FEATURE:
<223> OTHER INFORMATION: PRIMER FOR PREPARING Gi/olf28

<400> SEQUENCE: 49
cccgtggctg tattgaggtc ttcaaactga cactg                35

<210> SEQ ID NO 50
<211> LENGTH: 33
<212> TYPE: DNA
<213> ORGANISM: Artificial
<220> FEATURE:
<223> OTHER INFORMATION: PRIMER FOR PREPARING Gi/olf28

<400> SEQUENCE: 50
agtttgaaga cctcaataca gccacgggtg atg                33

<210> SEQ ID NO 51
<211> LENGTH: 34
<212> TYPE: DNA
<213> ORGANISM: Artificial
<220> FEATURE:
<223> OTHER INFORMATION: PRIMER FOR PREPARING Gi/olf28

<400> SEQUENCE: 51
accgtcgacg tcacaagagt tcgtactgct tgag                34

<210> SEQ ID NO 52
<211> LENGTH: 30
<212> TYPE: DNA
<213> ORGANISM: Artificial
<220> FEATURE:
<223> OTHER INFORMATION: PRIMER FOR PREPARING Gi/olf alpha3-beta5

<400> SEQUENCE: 52
tgatggaaat ggttcgcaac cacttgttgt                30

<210> SEQ ID NO 53
<211> LENGTH: 33
<212> TYPE: DNA
<213> ORGANISM: Artificial
<220> FEATURE:
<223> OTHER INFORMATION: PRIMER FOR PREPARING Gi/olf alpha3-beta5

<400> SEQUENCE: 53
gaaccatttc catcatcctt ttcctcaaca aga                33

<210> SEQ ID NO 54
<211> LENGTH: 39
<212> TYPE: DNA
<213> ORGANISM: Artificial
<220> FEATURE:
<223> OTHER INFORMATION: PRIMER FOR PREPARING Gi/olf alpha3-beta5

<400> SEQUENCE: 54
tttgtcgaca ttcgccattc aggctgcgca actgttggg                39

<210> SEQ ID NO 55
<211> LENGTH: 39
<212> TYPE: DNA
<213> ORGANISM: Artificial
<220> FEATURE:
<223> OTHER INFORMATION: PRIMER FOR PREPARING Gi/olf alpha3-beta5

<400> SEQUENCE: 55
tttgtcgaca ttcgccattc aggctgcgca actgttggg        39

<210> SEQ ID NO 56
<211> LENGTH: 28
<212> TYPE: DNA
<213> ORGANISM: Artificial
<220> FEATURE:
<223> OTHER INFORMATION: PRIMER FOR PREPARING Gi/olf alpha4-beta6

<400> SEQUENCE: 56
gtgtagcagt aatgtttgcc atcacccg        28

<210> SEQ ID NO 57
<211> LENGTH: 25
<212> TYPE: DNA
<213> ORGANISM: Artificial
<220> FEATURE:
<223> OTHER INFORMATION: PRIMER FOR PREPARING Gi/olf alpha4-beta6

<400> SEQUENCE: 57
tactgctaca cccacttcac gtgcg        25

<210> SEQ ID NO 58
<211> LENGTH: 35
<212> TYPE: DNA
<213> ORGANISM: Artificial
<220> FEATURE:
<223> OTHER INFORMATION: PRIMER FOR PREPARING Gi/olf 45

<400> SEQUENCE: 58
cctgaattct gccaccatgg gctgcacatt gagcg        35

<210> SEQ ID NO 59
<211> LENGTH: 26
<212> TYPE: DNA
<213> ORGANISM: Artificial
<220> FEATURE:
<223> OTHER INFORMATION: PRIMER FOR PREPARING Gi/olf 45

<400> SEQUENCE: 59
tgtgtccacg gcgcacgtga agtggg        26

<210> SEQ ID NO 60
<211> LENGTH: 29
<212> TYPE: DNA
<213> ORGANISM: Artificial
<220> FEATURE:
<223> OTHER INFORMATION: PRIMER FOR PREPARING Gi/olf 45

<400> SEQUENCE: 60
acgtgcgccg tggacacaga gaacatccg        29

<210> SEQ ID NO 61
<211> LENGTH: 34
<212> TYPE: DNA
<213> ORGANISM: Artificial
<220> FEATURE:
<223> OTHER INFORMATION: PRIMER FOR PREPARING Gi/olf 45

<400> SEQUENCE: 61
accgtcgacg tcacaagagt tcgtactgct tgag        34

<210> SEQ ID NO 62
<211> LENGTH: 35
<212> TYPE: DNA
<213> ORGANISM: Artificial

```
<220> FEATURE:
<223> OTHER INFORMATION: PRIMER FOR PREPARING Gi/olf 94

<400> SEQUENCE: 62
cctgaattct gccaccatgg gctgcacatt gagcg                          35

<210> SEQ ID NO 63
<211> LENGTH: 34
<212> TYPE: DNA
<213> ORGANISM: Artificial
<220> FEATURE:
<223> OTHER INFORMATION: PRIMER FOR PREPARING Gi/olf 94

<400> SEQUENCE: 63
tgccaagact ttttcttcga agaggtcctt cttg                           34

<210> SEQ ID NO 64
<211> LENGTH: 34
<212> TYPE: DNA
<213> ORGANISM: Artificial
<220> FEATURE:
<223> OTHER INFORMATION: PRIMER FOR PREPARING Gi/olf 94

<400> SEQUENCE: 64
gaagaaaaag tcttggcagg gaagtcaaaa atcg                           34

<210> SEQ ID NO 65
<211> LENGTH: 34
<212> TYPE: DNA
<213> ORGANISM: Artificial
<220> FEATURE:
<223> OTHER INFORMATION: PRIMER FOR PREPARING Gi/olf 94

<400> SEQUENCE: 65
accgtcgacg tcacaagagt tcgtactgct tgag                           34

<210> SEQ ID NO 66
<211> LENGTH: 35
<212> TYPE: DNA
<213> ORGANISM: Artificial
<220> FEATURE:
<223> OTHER INFORMATION: PRIMER FOR PREPARING Gi/olf 113

<400> SEQUENCE: 66
cctgaattct gccaccatgg gctgcacatt gagcg                          35

<210> SEQ ID NO 67
<211> LENGTH: 36
<212> TYPE: DNA
<213> ORGANISM: Artificial
<220> FEATURE:
<223> OTHER INFORMATION: PRIMER FOR PREPARING Gi/olf 113

<400> SEQUENCE: 67
atggttcgca accacttgtt gttacagatg ctatcg                         36

<210> SEQ ID NO 68
<211> LENGTH: 33
<212> TYPE: DNA
<213> ORGANISM: Artificial
<220> FEATURE:
<223> OTHER INFORMATION: PRIMER FOR PREPARING Gi/olf 113

<400> SEQUENCE: 68
acaacaagtg gttgcgaacc atttctatca tcc                            33
```

```
<210> SEQ ID NO 69
<211> LENGTH: 34
<212> TYPE: DNA
<213> ORGANISM: Artificial
<220> FEATURE:
<223> OTHER INFORMATION: PRIMER FOR PREPARING Gi/olf 113

<400> SEQUENCE: 69
accgtcgacg tcacaagagt tcgtactgct tgag                      34

<210> SEQ ID NO 70
<211> LENGTH: 35
<212> TYPE: DNA
<213> ORGANISM: Artificial
<220> FEATURE:
<223> OTHER INFORMATION: PRIMER FOR PREPARING Gi/olf 156

<400> SEQUENCE: 70
cctgaattct gccaccatgg gctgcacatt gagcg                     35

<210> SEQ ID NO 71
<211> LENGTH: 32
<212> TYPE: DNA
<213> ORGANISM: Artificial
<220> FEATURE:
<223> OTHER INFORMATION: PRIMER FOR PREPARING Gi/olf 156

<400> SEQUENCE: 71
acatcattaa agcagtggat ccacttcttc cg                        32

<210> SEQ ID NO 72
<211> LENGTH: 33
<212> TYPE: DNA
<213> ORGANISM: Artificial
<220> FEATURE:
<223> OTHER INFORMATION: PRIMER FOR PREPARING Gi/olf 156

<400> SEQUENCE: 72
actgctttaa tgatgtcact gcgatcattt acg                       33

<210> SEQ ID NO 73
<211> LENGTH: 34
<212> TYPE: DNA
<213> ORGANISM: Artificial
<220> FEATURE:
<223> OTHER INFORMATION: PRIMER FOR PREPARING Gi/olf 156

<400> SEQUENCE: 73
accgtcgacg tcacaagagt tcgtactgct tgag                      34

<210> SEQ ID NO 74
<211> LENGTH: 35
<212> TYPE: DNA
<213> ORGANISM: Artificial
<220> FEATURE:
<223> OTHER INFORMATION: PRIMER FOR PREPARING Gi/olf 195

<400> SEQUENCE: 74
cctgaattct gccaccatgg gctgcacatt gagcg                     35

<210> SEQ ID NO 75
<211> LENGTH: 31
<212> TYPE: DNA
<213> ORGANISM: Artificial
<220> FEATURE:
<223> OTHER INFORMATION: PRIMER FOR PREPARING Gi/olf 195

<400> SEQUENCE: 75
```

```
actctgcatc tgaggacatc ctgctgagtt g                              31
```

<210> SEQ ID NO 76
<211> LENGTH: 29
<212> TYPE: DNA
<213> ORGANISM: Artificial
<220> FEATURE:
<223> OTHER INFORMATION: PRIMER FOR PREPARING Gi/olf 195

<400> SEQUENCE: 76

```
gtcctcagat gcagagtgct gacatcagg                                 29
```

<210> SEQ ID NO 77
<211> LENGTH: 34
<212> TYPE: DNA
<213> ORGANISM: Artificial
<220> FEATURE:
<223> OTHER INFORMATION: PRIMER FOR PREPARING Gi/olf 195

<400> SEQUENCE: 77

```
accgtcgacg tcacaagagt tcgtactgct tgag                           34
```

<210> SEQ ID NO 78
<211> LENGTH: 27
<212> TYPE: DNA
<213> ORGANISM: Artificial
<220> FEATURE:
<223> OTHER INFORMATION: PRIMER FOR PREPARING Kir3.1(F137Sj

<400> SEQUENCE: 78

```
gcctcgagct atgtgaaacg gtcagag                                   27
```